US005763174A

United States Patent [19]
Nishikura

[11] Patent Number: 5,763,174
[45] Date of Patent: Jun. 9, 1998

[54] RNA EDITING ENZYME AND METHODS OF USE THEREOF

[75] Inventor: Kazuko Nishikura, Haddonfield, N.J.

[73] Assignee: The Wistar Institute of Anatomy & Biology, Philadelphia, Pa.

[21] Appl. No.: 555,678

[22] Filed: Nov. 13, 1995

Related U.S. Application Data

[63] Continuation-in-part of Ser. No. 457,459, Jun. 1, 1995, which is a continuation-in-part of Ser. No. 280,443, Jul. 25, 1994, Pat. No. 5,643,778, which is a continuation-in-part of Ser. No. 197,794, Feb. 17, 1994, abandoned.

[51] Int. Cl.⁶ .................... C12Q 1/68; G01N 33/567; G01N 33/53

[52] U.S. Cl. .................. 435/6; 435/7.1; 435/7.9; 435/7.91; 435/7.92; 435/7.93; 435/7.94; 435/7.95; 435/7.2; 436/518; 436/523; 436/531; 530/387.1; 530/387.9; 530/388.26; 530/389.1; 530/350; 536/23.2

[58] Field of Search .................. 435/6, 7.1, 7.9–7.95, 435/7.2; 436/578, 523, 531; 530/387.1, 387.9, 388.26, 389.1, 350; 536/23.2

[56] References Cited

U.S. PATENT DOCUMENTS

| | | | |
|---|---|---|---|
| 4,419,446 | 12/1983 | Howley et al. | 435/68.1 |
| 4,822,736 | 4/1989 | Kellems et al. | |
| 5,004,810 | 4/1991 | Draper | 536/27 |

FOREIGN PATENT DOCUMENTS

WO95/22604  8/1995  WIPO.

OTHER PUBLICATIONS

B. Bass et al, "An Unwinding Activity that Covalently Modifies its Double–Stranded RNA Substrate", *Cell*, 55:1089–1098 (Dec. 23, 1988) [Bass I].

B. Bass et al, "A Developmentally Regulated Activity that Unwinds RNA Duplexes", *Cell*, 48:607–613 (Feb. 27, 1987) [Bass II].

B. Bass et al, "Biased Hypermutation of Viral RNA Genomes Could be Due to Unwinding/Modification of Double–Stranded RNA", *Cell*, 56:331 (Feb. 10, 1989) [Bass III].

R. Wagner et al, "A Double–Stranded RNA Unwinding Activity Introduces Structural Alterations by Means of Adenosine to Inosine Conversions in Mammalian Cells and Xenopus Eggs", *Proc. Natl. Acad. Sci. USA*, 86:2647–2651 (Apr. 1989) [Wagner I].

R. Wagner et al, "Cell Cycle Expression of RNA Duplex Unwindase Activity in Mammalian Cells", *Mol. Cell Biol.*, 8(2):770–777 (Feb. 1988) [Wagner II].

R. Wagner et al, "Double–Stranded RNA Unwinding and Modifying Activity is Detected Ubiquitously in Primary Tissues and Cell Lines", *Mol. Cell Biol.*, 10(10):5586–5590 (Oct. 1990) [Wagner III].

R. Wagner et al, "Expression of an RNA Duplex Unwindase Activity in Mammalian Cells", Current Communications in Molecular Biology/Antisense RNA and DNA, D.A. Melton, ed., Cold Spring Harbor Laboratory Press, pp. 103–109 (May, 1988) [Wagner IV].

M. Rebagliati et al, "Antisense RNA Injections in Fertilized Frog Eggs Reveal an RNA Duplex Unwinding Activity", *Cell*, 48:599–605 (Feb. 27, 1987).

Y. Skeiky et al, "Developmental Regulation of Covalent Modification of Double–Stranded RNA During Silkmoth Oogenesis", *J. Mol. Biol.*, 218:517–527 (Apr. 5, 1991).

A. Polson et al, "The Mechanism of Adenosine to Inosine Conversion by the Double–Stranded RNA Unwinding/Modifying Activity: A High–Performance Liquid Chromatography–Mass Spectrometry Analysis", *Biochem.*, 30:11507–11514 (Dec. 10, 1991) [Polson I].

K. Nishikura et al, "Substrate Specificity of the dsRNA Unwinding/Modifying Activity", *EMBO J.*, 10(11):3523–3532 (Oct. 11, 1991) [Nishikura I].

K. Nishikura et al, "Modulation of Double–Stranded RNAs in vivo by RNA Duplex Unwindase", *Annals of the New York Acad. of Sci.*, 660:240–250 (Oct. 28, 1992) [Nishikura II].

K. Nishikura, "A Cellular Activity that Modifies and Alters the Structure of Double–Stranded RNA", *Gene Regulation: Biology of Antisense RNA and DNA*, R.P. Erickson et al, eds., Raven Press Ltd., NY. pp. 21–34 (Dec. 11, 1991) [Nishikura III].

D. Kimelman et al, "An Antisense mRNA Directs the Covalent Modification of the Transcript Encoding Fibroblast Growth Factor in Xenopus Ooctyes", *Cell*, 59:687–696 (Nov. 17, 1989).

R. Cattaneo et al, "Biased Hypermutation and Other Genetic Changes in Defective Measles Viruses in Human Brian Infections", *Cell*, 55:255–265 (Oct. 21, 1988).

L. Sharmeen et al, "Tat–dependent Adenosine–to–Inosine Modification of Wild–type Transactivation Response RNA", *Proc. Natl. Acad. Sci. USA*, 88:8096–8100 (Sep. 1991).

U. Kim et al, "Double–stranded RNA Adenosine Deaminase: A Potential Agent for RNA Editing?", in RNA Editing, R. Benne, Ed. (Simon and Schuster International, Chichester, England, pp. 179–192 (Jul. 1993) [Kim I].

U. Kim et al, "Double–stranded RNA Adenosine Deaminase as a Potential Mammalian RNA Editing Factor", *Seminars in Cell Biology*, 4:285–293 (Aug. 19, 1993) [Kim II].

U. Kim et al, "Purification and Characterization of Double–Stranded RNA Adenosine Deaminase from Bovine Nuclear Extracts", *J. Biol. Chem.*, 269(18):13480–13489 (May 6, 1994) [Kim III].

(List continued on next page.)

*Primary Examiner*—Sheela Huff
*Attorney, Agent, or Firm*—Howson and Howson

[57] ABSTRACT

The present invention provides novel human polynucleotide sequences and the recombinant human DRADA proteins encoded thereby and methods of use thereof.

9 Claims, 18 Drawing Sheets

OTHER PUBLICATIONS

B. Sommer et al, "RNA Editing in Brain Controls a Determinant of Ion Flow in Glutamate–Gated Channels", *Cell*, 67:11–19 (Oct. 4, 1991).

T. Verdoorn et al, "Structural Determinants of Ion Flow Through Recombinant Glutamate Receptor Channels", *Science*, 252:1715–1718 (Jun. 21, 1991).

M. Kohler et al, "Determinants of Ca2+ Permeability in Both TM1 and TM2 of High Affinity Kainate Receptor Channels: Diversity by RNA Editing", *Neuron*, 10:491–500 (Mar. 1993).

M. Higuchi et al, "RNA Editing of AMPA Receptor Subunit GluR–B: A Base–Paired Intron Exon Structure Determines Position and Efficiency", *Cell*, 75(7):1361–1370 (Dec. 31, 1993).

S. Rataul et al, "Irreversible Modification of Measles Virus RNA in Vitro by Nuclear RNA–Unwinding Activity in Human Neuroblastoma Cells", *J. Virol.*, 66(3):1769–1773 (Mar. 1992).

J. Thakkar et al, "Isolation and Characterization of AMP Deaminase from Mammalian (Rabbit) Myocardium", *Biochem. J.*, 290:335–341 (Mar. 1, 1993).

C. Yang et al, "Cloning and Nucleotide Sequence of the *Escherichia coli* Cytidine Deaminase (ccd) Gene", *Biochemistry*, 31:4168–4174 (May 5, 1992).

D. Wilson et al, "Atomic Structure of Adenosine Deaminase Complexed with a Transition–State Analog: Understanding Catalysis and Immunodeficiency Mutations", *Science*, 252:1278–1284 (May 31, 1991).

G. Cesareni, "Peptide Display on Filamentous Phage Capsids—A New Powerful Tool to Study Protein–Ligand Interaction", *FEBS Letters*, 307(1):66–70 (Jul. 1992).

H. Gram et al, "Phage Display as a Rapid Gene Expression System: Production of Bioactive Cytokine–Phage and Generation of Neutralizing Monoclonal Antibodies", *J. Immunol. Methods*, 161:169–176 (May 27, 1993).

J. Grinspan et al, "Bovine Endothelial Cells Transformed in Vitro by Benzo(a)pyrene", *J. Cell Physiol.*, 114:328–338 (1983).

A. Gatignol et al, "Relatedness of a RNA–Binding Motif in Human Immunodeficiency Virus Type 1 TAR RNA–Binding Protein TRBP to Human P1/dsI Kinase and Drosophila Staufen", *Mol. Cell. Biol*, 13(4):2193–2202 (Apr. 1993).

D. St. Johnston et al, "A Conserved Double–Stranded RNA–Binding Domain", *Proc. Natl. Acad. Sci. USA*, 89:10979–10983 (Nov. 1992).

D. Miller et al, "An Insect Baculovirus Host–Vector System for High–Level Expression of Foreign Genes", *Genetic Engineering*, 8:277–298 (Plenum Press 1986).

M. Gething et al, "Cell–Surface Expression of Influenza Haemagglutinin from a Cloned DNA Copy of the RNA Gene", *Nature*, 293:620–625 (Oct. 1981).

R. Kaufman et al, "Coamplification and Coexpression of Human Tissue–Type Plasminogen Activator and Murine Dihydrofolate Reductase Sequences in Chinese Hamster Ovary Cells", *Mol. Cell Biol*, 5(7):1750–1759 (Jul. 1985).

C. Swimmer et al, "Phage Display of Ricin B Chain and its Single Binding Domains: System for Screening Galactose–Binding Mutants", *Proc. Natl. Acad. Sci. USA*, 89:3756–3760 (May 1992).

J. Dignam et al, "Accurate Transcription Initiation by RNA Polymerase II in a Soluble Extract from Isolated Mammalian Nuclei", *Nucleic Acids Res.*, 11(5):1475–1489 (1983).

M. SilberKlang et a, "Use of in Vitro 32P Labeling in the Sequence Analysis of Nonradioactive tRNAs", *Methods Enzymol.*59:58–109 (1979).

C. Lee et al, "cDNA Cloning Using Degenerate Primers", in *PCR Protocols: A Guide to Methods and Application*, M. A. Innis et al, eds., Academic Press, Inc., San Diego, CA, pp. 46–53 (1990).

M. Kozak, "The Scanning Model for Translation: An Update", *J. Cell. Biol.*, 108:229–241 (1989).

J. Devereux et al, "A Comprehensive Set of Sequence Analysis Programs for the VAX", *Nucleic Acids Res.*, 12(1):387–395 (1984).

S. Haynes, "Research Review: The RNP Motif Protein Family", *New Biol.*, 4(5):421–429 (May 1992).

Z. Chang et al, "Deduced Amino Acid Sequence of *Escherichia coli* Adenosine Deaminase Reveals Evolutionarily Conserved Amino Acid Residues: Implications for Catalytic Function", *Biochem.*, 30:2273–2280 (1991).

B. Teng et al, "Molecular Cloning of an Apolipoprotein B Messenger RNA Editing Protein", *Science*, 260:1816–1819 (Jun., 1993).

R. Wilson et al, "2.2 Mb of Contiguous Nucleotide Sequence from Chromosome III of *C. elegans*", *Nature (London)*, 368:32–38 (Mar. 1994).

Adams et al, "3,400 New Expressed Sequence Tags Identify Diversity of Transcripts from Human Brain", *Nature Genet.*, 4:256–267 (Jul., 1993).

Miki et al, "Description of the APC Gene by a Retrotransposal Insertion of L1 Sequence in Colon Cancer", *Cancer Res.*, 52:643–645 (Feb., 1992).

Sambrook et al, *Molecular Cloning*, 2d ed., p. 163 (Nov., 1989).

Hyunh et al, "Constructing and Screening cDNA Libraries in lambdagt10 and lambdagt11", *DNA Cloning*, ed. Glover, IRL Press, pp. 49–78 (Aug., 1985).

Lathe et al, "Synthetic Oligonucleotide Probes Deduced from Amino Acid Sequence Data", *J. Mol. Biol.*, 183(1):1–12 (May, 1985).

G–S. Feng et al, "Identification of Double–Stranded RNA–Binding Domains in the Interferon–induced Double–stranded RNA–activated p68 Kinase", *Proc. Natl. Acad. Sci. USA*, 89:5447–5451 (Jun., 1992).

E. Meurs et al, "Molecular Cloning and Characterization of the Human Double–Stranded RNa–Activated Protein Kinase Induced by Interferon", *Cell*, 62:379–390 (Jul. 27, 1990).

G. Dabiri et al, "Editing of the GluR–B Ion Channel RNA in vitro by Recombinant Double–Stranded RNA Adenosine Deaminase", *EMBO J.*, 15(1);34–45 (Jan., 1996).

Y. Wang et al, "Genomic Organization and Chromosomal Location of the Human dsRNA Adenosine Deaminase Gene: The Enzyme for Glutamate–Activated Ion Channel RNA Editing", *J. Mol. Biol.*, 254:184–195 (Nov. 24, 1995).

R. Hough et al, "The Double–Stranded RNA Adenosine Deaminase", *J. Cell. Biochem.*, Suppl. 18C:130 (Abstract No. MZ 025) (Feb. 19, 1994) [Hough I].

R. Hough et al, "Purification of the *Xenopus laevis* Double–Stranded RNA Adenosine Deaminase", *J. Biol. Chem.*, 269(13):9933–9939 (Apr., 1994) [Hough II].

L. Chan et al, "RNA Editing", *Scientific American Science & Medicine*, pp. 68–77 (Mar./Apr., 1995).

S. Green et al, "Two RNA–binding Motifs in the Double–stranded RNA–activated Protein Kinase, DAI", *Genes and Development*, 6:2478–2490 (1992).

S. Nakanishi, "Molecular Diversity of Glutamate Receptors and Implications for Brain Function", *Science*, 258:597–603 (Oct. 23, 1992).

J. Greeve et al, "Characterization of the Apoliprotein B mRNA Editing Enzyme: No Similarity to the Proposed Mechanism of RNA Editing in Kinetoplastid Protozoa", *Nucl. Acids Res.*, 19(13):3569–3576 (Jul. 11, 1991).

S. McCormack et al, "Mechanism of Interferon Action: Identification of a RNA Binding Domain within the N-terminal Region of the Human RNA-Dependent p1/eIF-2a Protein Kinase", *Virology*, 188:47–56 (1992).

I. Mattaj, "RNA Recognition: A Family Matter?", *Cell*, 73:837–840 (Jun. 4, 1993).

A. Polson et al, "Preferential Selection of Adenosines for Modification by Double-Stranded RNA Adenosine Deaminase", *EMBO J.*, 13(23):5701–5711 (Dec., 1994) [Polson II].

U. Kim et al, "Molecular Cloning of cDNA for Double-Stranded RNA Adenosine Deaminase, a Candidate Enzyme for Nuclear RNA Editing", *Proc. Natl. Acad. Sci. USA*, 91:11457–11461 (Nov., 1994).

FIGURE 1A

| | | | | |
|---|---|---|---|---|
| CGCAGACCCG | CGGAGTTTCC | CGTGCCGACG | CCCCGGGGCC | ACTTCCAGTG | 50 |
| CGGAGTAGCG | GAGGCGTGGG | GGCCTCGAGG | GGCTGGCGCG | GTCCAGCGGT | 100 |
| CGGGCCAGGG | TCGTGCCGCC | GGCGGGTCGG | GCCGGACAAT | GCCTCGCGGG | 150 |

```
CGCA ATG AAT CCG CGG CAG GGG TAT TCC CTC AGC GGA TAC TAC       193
     Met Asn Pro Arg Gln Gly Tyr Ser Leu Ser Gly Tyr Tyr
      1               5                  10

ACC CAT CCA TTT CAA GGC TAT GAG CAC AGA CAG CTC AGA TAC        235
Thr His Pro Phe Gln Gly Tyr Glu His Arg Gln Leu Arg Tyr
        15              20              25

CAG CAG CCT GGG CCA GGA TCT TCC CCC AGT AGT TTC CTG CTT        277
Gln Gln Pro Gly Pro Gly Ser Ser Pro Ser Ser Phe Leu Leu
            30              35              40

AAG CAA ATA GAA TTT CTC AAG GGG CAG CTC CCA GAA GCA CCG        319
Lys Gln Ile Glu Phe Leu Lys Gly Gln Leu Pro Glu Ala Pro
                45              50              55

GTG ATT GGA AAG CAG ACA CCG TCA CTG CCA CCT TCC CTC CCA        361
Val Ile Gly Lys Gln Thr Pro Ser Leu Pro Pro Ser Leu Pro
                    60              65

GGA CTC CGG CCA AGG TTT CCA GTA CTA CTT GCC TCC AGT ACC        403
Gly Leu Arg Pro Arg Phe Pro Val Leu Leu Ala Ser Ser Thr
70                      75              80

AGA GGC AGG CAA GTG GAC ATC AGG GGT GTC CCC AGG GGC GTG        445
Arg Gly Arg Gln Val Asp Ile Arg Gly Val Pro Arg Gly Val
        85              90              95

CAT CTC GGA AGT CAG GGG CTC CAG AGA GGG TTC CAG CAT CCT        487
His Leu Gly Ser Gln Gly Leu Gln Arg Gly Phe Gln His Pro
            100             105             110

TCA CCA CGT GGC AGG AGT CTG CCA CAG AGA GGT GTT GAT TGC        529
Ser Pro Arg Gly Arg Ser Leu Pro Gln Arg Gly Val Asp Cys
                115             120             125

CTT TCC TCA CAT TTC CAG GAA CTG AGT ATC TAC CAA GAT CAG        571
Leu Ser Ser His Phe Gln Glu Leu Ser Ile Tyr Gln Asp Gln
                    130             135

GAA CAA AGG ATC TTA AAG TTC CTG GAA GAG CTT GGG GAA GGG        613
Glu Gln Arg Ile Leu Lys Phe Leu Glu Glu Leu Gly Glu Gly
140                     145             150
```

FIGURE 1B

```
AAG GCC ACC ACA GCA CAT GAT CTG TCT GGG AAA CTT GGG ACT    655
Lys Ala Thr Thr Ala His Asp Leu Ser Gly Lys Leu Gly Thr
    155             160                 165

CCG AAG AAA GAA ATC AAT CGA GTT TTA TAC TCC CTG GCA AAG    697
Pro Lys Lys Glu Ile Asn Arg Val Leu Tyr Ser Leu Ala Lys
    170                 175                 180

AAG GGC AAG CTA CAG AAA GAG GCA GGA ACA CCC CCT TTG TGG    739
Lys Gly Lys Leu Gln Lys Glu Ala Gly Thr Pro Pro Leu Trp
            185                 190                 195

AAA ATC GCG GTC TCC ACT CAG GCT TGG AAC CAG CAC AGC GGA    781
Lys Ile Ala Val Ser Thr Gln Ala Trp Asn Gln His Ser Gly
                200                 205

GTG GTA AGA CCA GAC GGT CAT AGC CAA GGA GCC CCA AAC TCA    823
Val Val Arg Pro Asp Gly His Ser Gln Gly Ala Pro Asn Ser
210                 215                 220

GAC CCG AGT TTG GAA CCG GAA GAC AGA AAC TCC ACA TCT GTC    865
Asp Pro Ser Leu Glu Pro Glu Asp Arg Asn Ser Thr Ser Val
    225                 230                 235

TCA GAA GAT CTT CTT GAG CCT TTT ATT GCA GTC TCA GCT CAG    907
Ser Glu Asp Leu Leu Glu Pro Phe Ile Ala Val Ser Ala Gln
        240                 245                 250

GCT TGG AAC CAG CAC AGC GGA GTG GTA AGA CCA GAC AGT CAT    949
Ala Trp Asn Gln His Ser Gly Val Val Arg Pro Asp Ser His
                255                 260                 265

AGC CAA GGA TCC CCA AAC TCA GAC CCA GGT TTG GAA CCT GAA    991
Ser Gln Gly Ser Pro Asn Ser Asp Pro Gly Leu Glu Pro Glu
                270                 275

GAC AGC AAC TCC ACA TCT GCC TTG GAA GAT CCT CTT GAG TTT    1033
Asp Ser Asn Ser Thr Ser Ala Leu Glu Asp Pro Leu Glu Phe
280                 285                 290

TTA GAC ATG GCC GAG ATC AAG GAG AAA ATC TGC GAC TAT CTC    1075
Leu Asp Met Ala Glu Ile Lys Glu Lys Ile Cys Asp Tyr Leu
    295                 300                 305

TTC AAT GTG TCT GAC TCC TCT GCC CTG AAT TTG GCT AAA AAT    1117
Phe Asn Val Ser Asp Ser Ser Ala Leu Asn Leu Ala Lys Asn
        310                 315                 320

ATT GGC CTT ACC AAG GCC CGA GAT ATA AAT GCT GTG CTA ATT    1159
Ile Gly Leu Thr Lys Ala Arg Asp Ile Asn Ala Val Leu Ile
            325                 330                 335
```

FIGURE 1C

```
GAC ATG GAA AGG CAG GGG GAT GTC TAT AGA CAA GGG ACA ACC   1201
Asp Met Glu Arg Gln Gly Asp Val Tyr Arg Gln Gly Thr Thr
            340             345

CCT CCC ATA TGG CAT TTG ACA GAC AAG AAG CGA GAG AGG ATG   1243
Pro Pro Ile Trp His Leu Thr Asp Lys Lys Arg Glu Arg Met
350             355             360

CAA ATC AAG AGA AAT ACG AAC AGT GTT CCT GAA ACC GCT CCA   1285
Gln Ile Lys Arg Asn Thr Asn Ser Val Pro Glu Thr Ala Pro
        365             370             375

GCT GCA ATC CCT GAG ACC AAA AGA AAC GCA GAG TTC CTC ACC   1327
Ala Ala Ile Pro Glu Thr Lys Arg Asn Ala Glu Phe Leu Thr
            380             385             390

┌--->93 kd
TGT AAT ATA CCC ACA TCA AAT GCC TCA AAT AAC ATG GTA ACC   1369
Cys Asn Ile Pro Thr Ser Asn Ala Ser Asn Asn Met Val Thr
                395             400             405

ACA GAA AAA GTG GAG AAT GGG CAG GAA CCT GTC ATA AAG TTA   1411
Thr Glu Lys Val Glu Asn Gly Gln Glu Pro Val Ile Lys Leu
            410             415

GAA AAC AGG CAA GAG GCC AGA CCA GAA CCA GCA AGA CTG AAA   1453
Glu Asn Arg Gln Glu Ala Arg Pro Glu Pro Ala Arg Leu Lys
420             425             430

┌--->88 kd
CCA CCT GTT CAT TAC AAT GGC CCC TCA AAA GCA GGG TAT GTT   1495
Pro Pro Val His Tyr Asn Gly Pro Ser Lys Ala Gly Tyr Val
    435             440             445

GAC TTT GAA AAT GGC CAG TGG GCC ACA GAT GAC ATC CCA GAT   1537
Asp Phe Glu Asn Gly Gln Trp Ala Thr Asp Asp Ile Pro Asp
        450             455             460

GAC TTG AAT AGT ATC CGC GCA GCA CCA GGT GAG TTT CGA GCC   1579
Asp Leu Asn Ser Ile Arg Ala Ala Pro Gly Glu Phe Arg Ala
            465             470             475

ATC ATG GAG ATG CCC TCC TTC TAC AGT CAT GGC TTG CCA CGG   1621
Ile Met Glu Met Pro Ser Phe Tyr Ser His Gly Leu Pro Arg
                480             485

TGT TCA CCC TAC AAG AAA CTG ACA GAG TGC CAG CTG AAG AAC   1663
Cys Ser Pro Tyr Lys Lys Leu Thr Glu Cys Gln Leu Lys Asn
490             495             500
```

FIGURE 1D

| | | | | | | | | | | | | | |
|---|---|---|---|---|---|---|---|---|---|---|---|---|---|
| CCC | ATC | AGC | GGG | CTG | TTA | GAA | TAT | GCC | CAG | TTC | GCT | AGT | CAA | 1705
| Pro | Ile | Ser | Gly | Leu | Leu | Glu | Tyr | Ala | Gln | Phe | Ala | Ser | Gln |
| | 505 | | | | | 510 | | | | | 515 | | |

| ACC | TGT | GAG | TTC | AAC | ATG | ATA | GAG | CAG | AGT | GGA | CCA | CCC | CAT | 1747
|---|---|---|---|---|---|---|---|---|---|---|---|---|---|
| Thr | Cys | Glu | Phe | Asn | Met | Ile | Glu | Gln | Ser | Gly | Pro | Pro | His |
| | | 520 | | | | | 525 | | | | | 530 | |

DRBM1

| GAA | CCT | CGA | TTT | AAA | TTC | CAG | GTT | GTC | ATC | AAT | GGC | CGA | GAG | 1789
|---|---|---|---|---|---|---|---|---|---|---|---|---|---|
| Glu | Pro | Arg | Phe | Lys | Phe | Gln | Val | Val | Ile | Asn | Gly | Arg | Glu |
| | | | 535 | | | | | 540 | | | | | 545 |

| TTT | CCC | CCA | GCT | GAA | GCT | GGA | AGC | AAG | AAA | GTG | GCC | AAG | CAG | 1831
|---|---|---|---|---|---|---|---|---|---|---|---|---|---|
| Phe | Pro | Pro | Ala | Glu | Ala | Gly | Ser | Lys | Lys | Val | Ala | Lys | Gln |
| | | | | | 550 | | | | | 555 | | | |

| GAT | GCA | GCT | ATG | AAA | GCC | ATG | ACA | ATT | CTG | CTA | GAG | GAA | GCC | 1873
|---|---|---|---|---|---|---|---|---|---|---|---|---|---|
| Asp | Ala | Ala | Met | Lys | Ala | Met | Thr | Ile | Leu | Leu | Glu | Glu | Ala |
| 560 | | | | | 565 | | | | | 570 | | | |

| AAA | GCC | AAG | GAC | AGT | GGA | AAA | TCA | GAA | GAA | TCA | TCC | CAC | TAT | 1915
|---|---|---|---|---|---|---|---|---|---|---|---|---|---|
| Lys | Ala | Lys | Asp | Ser | Gly | Lys | Ser | Glu | Glu | Ser | Ser | His | Tyr |
| | 575 | | | | | 580 | | | | | 585 | | |

| TCC | ACA | GAG | AAA | GAA | TCA | GAG | AAG | ACT | GCA | GAG | TCC | CAG | ACC | 1957
|---|---|---|---|---|---|---|---|---|---|---|---|---|---|
| Ser | Thr | Glu | Lys | Glu | Ser | Glu | Lys | Thr | Ala | Glu | Ser | Gln | Thr |
| | | 590 | | | | | 595 | | | | | 600 | |

| CCC | ACC | CCT | TCA | GCC | ACA | TCC | TTC | TTT | TCT | GGG | AAG | AGC | CCC | 1999
|---|---|---|---|---|---|---|---|---|---|---|---|---|---|
| Pro | Thr | Pro | Ser | Ala | Thr | Ser | Phe | Phe | Ser | Gly | Lys | Ser | Pro |
| | | | 605 | | | | | 610 | | | | | 615 |

| GTC | ACC | ACA | CTG | CTT | GAG | TGT | ATG | CAC | AAA | TTG | GGG | AAC | TCC | 2041
|---|---|---|---|---|---|---|---|---|---|---|---|---|---|
| Val | Thr | Thr | Leu | Leu | Glu | Cys | Met | His | Lys | Leu | Gly | Asn | Ser |
| | | | | 620 | | | | | 625 | | | | |

| TGC | GAA | TTC | CGT | CTC | CTG | TCC | AAA | GAA | GGC | CCT | GCC | CAT | GAA | 2083
|---|---|---|---|---|---|---|---|---|---|---|---|---|---|
| Cys | Glu | Phe | Arg | Leu | Leu | Ser | Lys | Glu | Gly | Pro | Ala | His | Glu |
| 630 | | | | | 635 | | | | | 640 | | | |

DRBM2

| CCC | AAG | TTC | CAA | TAC | TGT | GTT | GCA | GTG | GGA | GCC | CAA | ACT | TTC | 2125
|---|---|---|---|---|---|---|---|---|---|---|---|---|---|
| Pro | Lys | Phe | Gln | Tyr | Cys | Val | Ala | Val | Gly | Ala | Gln | Thr | Phe |
| | 645 | | | | | 650 | | | | | 655 | | |

| CCC | AGT | GTG | AGT | GCT | CCC | AGC | AAG | AAA | GTG | GCA | AAG | CAG | ATG | 2167
|---|---|---|---|---|---|---|---|---|---|---|---|---|---|
| Pro | Ser | Val | Ser | Ala | Pro | Ser | Lys | Lys | Val | Ala | Lys | Gln | Met |
| | | 660 | | | | | 665 | | | | | 670 | |

FIGURE 1E

| | | | | | | | | | | | | | |
|---|---|---|---|---|---|---|---|---|---|---|---|---|---|
| GCC | GCA | GAG | GAA | GCC | ATG | AAG | GCC | CTG | CAT | GGG | GAG | GCG | ACC | 2209
| Ala | Ala | Glu | Glu | Ala | Met | Lys | Ala | Leu | His | Gly | Glu | Ala | Thr |
|  |  | 675 |  |  |  |  | 680 |  |  |  |  |  | 685 |

```
GCC GCA GAG GAA GCC ATG AAG GCC CTG CAT GGG GAG GCG ACC     2209
Ala Ala Glu Glu Ala Met Lys Ala Leu His Gly Glu Ala Thr
        675                 680                         685

AAC TCC ATG GCT TCT GAT AAC CAG CCT GAA GGT ATG ATC TCA     2251
Asn Ser Met Ala Ser Asp Asn Gln Pro Glu Gly Met Ile Ser
            690                 695

GAG TCA CTT GAT AAC TTG GAA TCC ATG ATG CCC AAC AAG GTC     2293
Glu Ser Leu Asp Asn Leu Glu Ser Met Met Pro Asn Lys Val
700             705                 710

AGG AAG ATT GGC GAG CTC GTG AGA TAC CTG AAC ACC AAC CCT     2335
Arg Lys Ile Gly Glu Leu Val Arg Tyr Leu Asn Thr Asn Pro
        715                 720                 725

GTG GGT GGC CTT TTG GAG TAC GCC CGC TCC CAT GGC TTT GCT     2377
Val Gly Gly Leu Leu Glu Tyr Ala Arg Ser His Gly Phe Ala
            730                 735             740

GCT GAA TTC AAG TTG GTC GAC CAG TCC GGA CCT CCT CAC GAG     2419
Ala Glu Phe Lys Leu Val Asp Gln Ser Gly Pro Pro His Glu
            745                 750                 755

DRBM3
CCC AAG TTC GTT TAC CAA GCA AAA GTT GGG GGT CGC TGG TTC     2461
Pro Lys Phe Val Tyr Gln Ala Lys Val Gly Gly Arg Trp Phe
                760                 765

CCA GCC GTC TGC GCA CAC AGC AAG AAG CAA GGC AAG CAG GAA     2503
Pro Ala Val Cys Ala His Ser Lys Lys Gln Gly Lys Gln Glu
770             775                 780

GCA GCA GAT GCG GCT CTC CGT GTC TTG ATT GGG GAG AAC GAG     2545
Ala Ala Asp Ala Ala Leu Arg Val Leu Ile Gly Glu Asn Glu
785                     790             795

AAG GCA GAA CGC ATG GGT TTC ACA GAG GTA ACC CCA GTG ACA     2587
Lys Ala Glu Arg Met Gly Phe Thr Glu Val Thr Pro Val Thr
        800                 805                 810

GGG GCC AGT CTC AGA AGA ACT ATG CTC CTC CTC TCA AGG TCC     2629
Gly Ala Ser Leu Arg Arg Thr Met Leu Leu Leu Ser Arg Ser
            815                 820                 825

CCA GAA GCA CAG CCA AAG ACA CTC CCT CTC ACT GGC AGC ACC     2671
Pro Glu Ala Gln Pro Lys Thr Leu Pro Leu Thr Gly Ser Thr
                830                 835
```

FIGURE 1F

| | | | | | | | | | | | | |
|---|---|---|---|---|---|---|---|---|---|---|---|---|
| TTC | CAT | GAC | CAG | ATA | GCC | ATG | CTG | AGC | CAC | CGG | TGC | TTC AAC | 2713
| Phe | His | Asp | Gln | Ile | Ala | Met | Leu | Ser | His | Arg | Cys | Phe Asn |
| 840 | | | | | 845 | | | | 850 | | | |

```
TTC CAT GAC CAG ATA GCC ATG CTG AGC CAC CGG TGC TTC AAC    2713
Phe His Asp Gln Ile Ala Met Leu Ser His Arg Cys Phe Asn
840               845              850

ACT CTG ACT AAC AGC TTC CAG CCC TCC TTG CTC GGC CGC AAG    2755
Thr Leu Thr Asn Ser Phe Gln Pro Ser Leu Leu Gly Arg Lys
    855              860              865

ATT CTG GCC GCC ATC ATT ATG AAA AAA GAC TCT GAG GAC ATG    2797
Ile Leu Ala Ala Ile Ile Met Lys Lys Asp Ser Glu Asp Met
        870              875              880

GGT GTC GTC GTC AGC TTG GGA ACA GGG AAT CGC TGT GTG AAA    2839
Gly Val Val Val Ser Leu Gly Thr Gly Asn Arg Cys Val Lys
            885              890              895

GGA GAT TCT CTC AGC CTA AAA GGA GAA ACT GTC AAT GAC TGC    2881
Gly Asp Ser Leu Ser Leu Lys Gly Glu Thr Val Asn Asp Cys
                900              905

CAT GCA GAA ATA ATC TCC CGG AGA GGC TTC ATC AGG TTT CTC    2923
His Ala Glu Ile Ile Ser Arg Arg Gly Phe Ile Arg Phe Leu
910                  915              920

TAC AGT GAG TTA ATG AAA TAC AAC TCC CAG ACT GCG AAG GAT    2965
Tyr Ser Glu Leu Met Lys Tyr Asn Ser Gln Thr Ala Lys Asp
    925              930              935

AGT ATA TTT GAA CCT GCT AAG GGA GGA GAA AAG CTC CAA ATA    3007
Ser Ile Phe Glu Pro Ala Lys Gly Gly Glu Lys Leu Gln Ile
        940              945              950

AAA AAG ACT GTG TCA TTC CAT CTG TAT ATC AGC ACT GCT CCG    3049
Lys Lys Thr Val Ser Phe His Leu Tyr Ile Ser Thr Ala Pro
            955              960              965

TGT GGA GAT GGC GCC CTC TTT GAC AAG TCC TGC AGC GAC CGT    3091
Cys Gly Asp Gly Ala Leu Phe Asp Lys Ser Cys Ser Asp Arg
                970              975

GCT ATG GAA AGC ACA GAA TCC CGC CAC TAC CCT GTC TTC GAG    3133
Ala Met Glu Ser Thr Glu Ser Arg His Tyr Pro Val Phe Glu
980                  985              990

AAT CCC AAA CAA GGA AAG CTC CGC ACC AAG GTG GAG AAC GGA    3175
Asn Pro Lys Gln Gly Lys Leu Arg Thr Lys Val Glu Asn Gly
    995              1000             1005

GAA GGC ACA ATC CCT GTG GAA TCC AGT GAC ATT GTG CCT ACG    3217
Glu Gly Thr Ile Pro Val Glu Ser Ser Asp Ile Val Pro Thr
        1010             1015             1020
```

FIGURE 1G

```
TGG GAT GGC ATT CGG CTC GGG GAG AGA CTC CGT ACC ATG TCC   3259
Trp Asp Gly Ile Arg Leu Gly Glu Arg Leu Arg Thr Met Ser
            1025                1030            1035

TGT AGT GAC AAA ATC CTA CGC TGG AAC GTG CTG GGC CTG CAA   3301
Cys Ser Asp Lys Ile Leu Arg Trp Asn Val Leu Gly Leu Gln
            1040                1045

GGG GCA CTG TTG ACC CAC TTC CTG CAG CCC ATT TAT CTC AAA   3343
Gly Ala Leu Leu Thr His Phe Leu Gln Pro Ile Tyr Leu Lys
1050            1055                1060

TCT GTC ACA TTG GGT TAC CTT TTC AGC CAA GGG CAT CTG ACC   3385
Ser Val Thr Leu Gly Tyr Leu Phe Ser Gln Gly His Leu Thr
            1065                1070            1075

CGT GCT ATT TGC TGT CGT GTG ACA AGA GAT GGG AGT GCA TTT   3427
Arg Ala Ile Cys Cys Arg Val Thr Arg Asp Gly Ser Ala Phe
            1080                1085            1090

GAG GAT GGA CTA CGA CAT CCC TTT ATT GTC AAC CAC CCC AAG   3469
Glu Asp Gly Leu Arg His Pro Phe Ile Val Asn His Pro Lys
            1095                1100            1105

GTT GGC AGA GTC AGC ATA TAT GAT TCC AAA AGG CAA TCC GGG   3511
Val Gly Arg Val Ser Ile Tyr Asp Ser Lys Arg Gln Ser Gly
                1110                1115

AAG ACT AAG GAG ACA AGC GTC AAC TGG TGT CTG GCT GAT GGC   3553
Lys Thr Lys Glu Thr Ser Val Asn Trp Cys Leu Ala Asp Gly
1120            1125                1130

TAT GAC CTG GAG ATC CTG GAC GGT ACC AGA GGC ACT GTG GAT   3595
Tyr Asp Leu Glu Ile Leu Asp Gly Thr Arg Gly Thr Val Asp
            1135                1140            1145

GGG CCA CGG AAT GAA TTG TCC CGG GTC TCC AAA AAG AAC ATT   3637
Gly Pro Arg Asn Glu Leu Ser Arg Val Ser Lys Lys Asn Ile
            1150                1155            1160

TTT CTT CTA TTT AAG AAG CTC TGC TCC TTC CGT TAC CGC AGG   3679
Phe Leu Leu Phe Lys Lys Leu Cys Ser Phe Arg Tyr Arg Arg
                1165            1170            1175

GAT CTA CTG AGA CTC TCC TAT GGT GAG GCC AAG AAA GCT GCC   3721
Asp Leu Leu Arg Leu Ser Tyr Gly Glu Ala Lys Lys Ala Ala
                1180            1185

CGT GAC TAC GAG ACG GCC AAG AAC TAC TTC AAA AAA GGC CTG   3763
Arg Asp Tyr Glu Thr Ala Lys Asn Tyr Phe Lys Lys Gly Leu
1190            1195                1200
```

FIGURE 1H

| | | | | | | | | | | | | |
|---|---|---|---|---|---|---|---|---|---|---|---|---|
| AAG | GAT | ATG | GGC | TAT | GGG | AAC | TGG | ATT | AGC | AAA | CCC | CAG GAG | 3805
| Lys | Asp | Met | Gly | Tyr | Gly | Asn | Trp | Ile | Ser | Lys | Pro | Gln Glu |
| | | 1205 | | | | 1210 | | | | 1215 | | |

```
AAG GAT ATG GGC TAT GGG AAC TGG ATT AGC AAA CCC CAG GAG    3805
Lys Asp Met Gly Tyr Gly Asn Trp Ile Ser Lys Pro Gln Glu
        1205            1210            1215

GAA AAG AAC TTT TAT CTC TGC CCA GTA TAGTATGCTC             3842
Phe Tyr Glu Lys Asn Leu Cys Pro Val
        1220            1225

CAGTGACAGA TGGATTAGGG TGTGTCATAC TAGGGTGTGA GAGAGGTAGG     3892

TCGTAGCATT CCTCATCACA TGGTCAGGGG ATTTTTTTTT CTCCTTTTTT     3942

TTTTCTTTTT AAGCCATAAT TGGTGATACT GAAAACTTTG GGTTCCCATT     3992

TATCCTGCTT TCTTTGGGAT TGCTAGGCAA GGTCTGGCCA GGCCCCCTT      4042

TTTTCCCCCA AGTGAAGAGG CAGAAACCTA GAAGTTATC TTTTCTTTCT      4092

ACCCAAAGCA TACATAGTCA CTGAGCACCT GCGGTCCATT TCCTCTTAAA     4142

AGTTTTGTTT TGATTTGTTT CCATTTCCTT TCCCTTTGTG TTTGCTACAC     4192

TGACCTCTTG CGGTCTTGAT TAGGTTTCAG TCAACTCTGG ATCATGTCAG     4242

GGACTGATAA TTTCATTTGT GGATTACGCA GACCCTCTA CTTCCCCTCT      4292

TTCCCTTCTG AGATTCTTTC CTTGTGATCT GAATGTCTCC TTTTCCCCCT     4342

CAGAGGGCAA AGAGGTGAAC ATAAAGGATT TGGTGAAACA TTTGTAAGGG     4392

TAGGAGTTGA AAACTGCAGT TCCCAGTGCC ACGGAAGTGT GATTGGAGCC     4442

TGCAGATAAT GCCCAGCCAT CCTCCCATCC TGCACTTTAG CCAGCTGCAG     4492

GGCGGGCAAG GCAAGGAAAG CTGCTTCCCT GGAAGTGTAT CACTTTCTCC     4542

GGCAGCTGGG AAGTCTAGAA CCAGCCAGAC TGGGTTAAGG GAGCTGCTCA     4592

AGCAATAGCA GAGGTTTCAC CCGGCAGGAT GACACAGACC ACTTCCCAGG     4642

GAGCACGGGC ATGCCTTGGA ATATTGCCAA GCTTCCAGCT GCCTCTTCTC     4692

CTAAAGCATT CCTAGGAATA TTTTCCCCGC CAATGCTGGG CGTACACCCT     4742

AGCCAACGGG ACAAATCCTA GAGGGTATAA AATCATCTCT GCTCAGATAA     4792

TCATGACTTA GCAAGAATAA GGGCAAAAAA TCCTGTTGGC TTAACGTCAC     4842

TGTTCCACCC GGTGTAATAT CTCTCATGAC AGTGACACCA AGGGAAGTTG     4892

ACTAAGTCAC ATGTAAATTA GGAGTGTTTT AAAGAATGCC ATAGATGTTG     4942
```

FIGURE 1I

```
ATTCTTAACT GCTACAGATA ACCTGTAATT GAGCAGATTT AAAATTCAGG    4992
CATACTTTTC CATTTATCCA AGTGCTTTCA TTTTTCCAGA TGGCTTCAGA    5042
AGTAGGCTCG TGGGCAGGGC GCAGACCTGA TCTTTATAGG GTTGACATAG    5092
AAAGCAGTAG TTGTGGGTGA AAGGGCAGGT TGTCTTCAAA CTCTGTGAGG    5142
TAGAATCCTT TGTCTATACC TCCATGAACA TTGACTCGTG TGTTCAGAGC    5192
CTTTGGCCTC TCTGTGGAGT CTGGCTCTCT GGCTCCTGTG CATTCTTTGA    5242
ATAGTCACTC GTAAAACTG TCAGTGCTTG AAACTGTTTC CTTTACTCAT     5292
GTTGAAGGGA CTTTGTTGGC TTTTAGAGTG TTGGTCATGA CTCCAAGAGC    5342
AGAGCAGGGA AGAGCCCAAG CATAGACTTG GTGCCGTGGT GATGGCTGCA    5392
GTCCAGTTTT GTGATGCTGC TTTTACGTGT CCCTCGATAA CAGTCAGCTA    5442
GACACACTCA GGAGGACTAC TGAGGCTCTG CGACCTTCAG GAGCTGAGCC    5492
TGCCTCTCTC CTTTAGATGA CAGACCTTCA TCTGGGAACG TGCTGAGCCA    5542
GCACCCTCAG ATGATTTCCC TCCAAACTGC TGACTAGGTC ATCCTCTGTC    5592
TGGTAGAGAC ATTCACATCT TTGCTTTTAT TCTATGCTCT CTGTACTTTT    5642
GACCAAAAAT TGACCAAAGT AAGAAAATGC AAGTTCTAAA AATAGACTAA    5692
GGATGCCTTT GCAGAACACC AAAGCATCCC AAGGAACTGG TAGGGAAGTG    5742
GCGCCTGTCT CCTGGAGTGG AAGAGGCCTG CTCCCTGCTC TGGGTCTGCT    5792
GGGGGCACAG TAAATCAGTC TTGGCACCCA CATCCAGGGC AGAGAGGTCT    5842
GTGGTTCTCA GCATCAGAAG GCAGCGCAGC CCCTCTCCTC TTCAGGCTAC    5892
AGGGTTGTCA CCTGCTGAGT CCTCAGGTTG TTTGGCCTCT CTGGTCCATC    5942
TTGGGCATTA GGTTCTCCAG CAGAGCTCTG GCCAGCTGCC TCTTCTTTAA    5992
CTGGGAACAC AGGCTCTCAC AAGATCAGAA CCCCCACTCA CCCCCAAGAT    6042
CTTATCTAGC AAGCCTGTAG TATTCAGTTT CTGTTGTAGG AAGAGAGCGA    6092
GGCATCCCTG AATTCCACGC ATCTGCTGGA AACGAGCCGT GTCAGATCGC    6142
```

FIGURE 1J

```
ACATCCCTGC GCCCCCATGC CCCTCTGAGT CACACAGGAC AGAGGAGGCA      6192

GAGCTTCTGC CCACTGTTAT CTTCACTTTC TTTGTCCAGT CTTTTGTTTT      6242

TAATAAGCAG TGACCCTCCC TACTCTTCTT TTTAATGATT TTTGTAGTTG      6292

ATTTGTCTGA ACTGTGGCTA CTGTGCATTC CTTGAATAAT CACTTGTAAA      6342

AATTGTCAGT GCTTGAAGCT GTTTCCTTTA CTCACATTGA AGGGACTTCG      6392

TTGGTTTTTT GGAGTCTTGG TTGTGACTCC AAGAGCAGAG TGAGGAAGAC      6442

CCCCAAGCAT AGACTCGGGT ACTGTGATGA TGGCTGCAGT CCAGTTTTAT      6492

GATTCTGCTT TTATGTGTCC CTTGATAACA GTGACTTAAC AATATACATT      6542

CCTCATAAAT AAAAAAAAAA CAAGAATCTG AAAAAAAAAA AAAAAAAAAA      6592

AAAAAAAAAA AAAAAAAAAA AAAAAAAAAA AAAAAAAAAA AAAAAAAAAA      6642

AAAAAAAAAA AAAAAAAAAA AAAAAAAA                              6671
```

FIGURE 5

```
                                                                                                        SEQ ID NO
DRADA-1       KNPISGLL EYA QFASQTCEFNMIEQSGPPHEPRFKFQVVIN GREFPPAEAGSKKVAKQDAAMKAMTILLEEA                    3
DRADA-2       KSPVTTLL ECM HKLGNSCEFRLLSKEGPAHEPKFQYCVAV GAQTFPSVSAPSKKVAKQMAEEAMKALHGEA                    4
DRADA-3       TNPVGGLL EYA RSHGFAAEFKLVDQSGPPHEPKFVYQAKV GGRWFPAVCAHSKKQGKQEAADAALRVLIGEN                    5
P68kinase-1   AGFFMEELNTY RQKQGVVLKYQELPNSGPPHDRRFTFQVIID GREFPEGEGRSKKEAKNAAAKLAVEILNKEK                    6
P68kinase-2   GNYI GLINRIA QKKRLTVNYE QCASGVHGPEGFEYKCKM GQKEYSIGTGSTKQEAKQLAAKLAYLQILSEE                    7
TIKkinase-1   GFYMDK LNKY RQMHGVAITYKELSTSGPPHDRRFTFQVLID EKEFGEAKGRSKTEARNAAAKLAVDILDNEN                    8
TIKkinase-2   VGNYIGLVNSFA QKKKLSVLIE QCEPNSELPQRFICKCKI GQTMYGTGSGVTKQEAKQLAAKEAYQKLLKSP                    9
HuTRBP-1      KTPIS LLQEYG TRIGKTPVYDLLKAEGQAHQPNFTFRVTV GDTSCTGQGPSKKAAHKAEVALKELKGGS                      10
HuTRBP-2      CNPV GALQELVVQKGWRLPEYTVTQESGPAHRKEFTMTCRV ERFIEIGSGTSKKLAKRNAAAKMLLRVHTVP                    11
HuTRBP-3      GPACCRVLSELS EEQAFHVSYLDIEELSLSGLCQCLVELSTQ PATVCHGSATTREAARGEAARRALQYLKIMA                   12
X1TRBP-1      ETPIQ LLHEFG TKTGNHPVYTLEKAEGQAHNPSFTFRLVI GDITSLGEPSKKTPKQKAEFALNILRGDT                      13
X1TRBP-2      ENPV GSLQELAVQKGWRLPEYTVAQESGPPHKREFTITCRV ETFVETGSGTSKQVAKRVAAEKLLTKFKTIS                    14
X1TRBP-3      TDYV KMLKDVA EELDFNLTYLDIDELSVNGQYQCLAELSTN PITVCHGTGISCGNAHNDAAHNALQVLKIMC                   15
Staufen-1     KTPM CLVNELARYNKITHQ YRLTEERGPAHCKTFTVTLML GDEEYSADGFKIKKAQHLAASKAIEETMYKH                   16
Staufen-2     KFPSRFALPPPLGAHVHHGPNGPFP  SVPTPPSKIT LFV GKQKFVGIGRTLQQAKHDAAARALQVLKTQA                    17
Staufen-3     KSPIS QVHEIG IKRNMTVHFKVLREEGPAHMKNFITACIV GSIVTEGEGNGKKVSKKRAAEKMLVELQKLP                    18
Staufen-4     DNPITKLIQ LQQTRKEKEPIFELIAKNGNETARRREFVMEVSASGSTARGTGNSKKLAKRNAAQ ALFELLEAV                   19
Staufen-5     HMKE QLL YLS KLLDFEVNFSDY PKGNHNEFLTIVTLSTH PPQICHGVGKSSEESQNDAASNALKILSKLG                   20
Huson-a       KHPVSALM EICNKRRWQPPEFLLVHDSGPDHRKHFLFRVLINGSAYQPSFASPNKKEAKATAATVVLQAMGLVP                    21
E3L           ANPVT VINEYC QITRRDWSFRI ESVGPSNSPTFYACVDID GRVFDKADGKSKRDAKNNAAKLAVDKLLGYV                   22
Ns34          PDPLI RLNDCKTKYGIDIICRF   YIVLDNDGSIIHMCYMRTGSAEAVAKGRSKKEAKRIAAKDILDQIGL*                    23
Pac1          DKLAKSKLFHKY STLGHIEYRWVDGAG GSAEGYVIACIFN GKEVARAWGANQKDAGSRAAMQALEVLAKDY                    24
RNase III     KDPKT RLQEYLQGRHLPLPTYLVVQVRGEAHDQEFTIHCQVSGLSEPVVGTGSSRRKAEQAAAEQALKKLELE*                    25
Consensus     KNPV GLLNEYA QK G  PEY LL ESGPAHDPKFT V V GGREF  GSG SKKEAKQ AAE AL IL    E                    26
              I AMIQDFG   R A      F VV D  G EKRIY L I    AK Y    ATA TRRD RN   D V VI D
              M VV  L          II                      R L MM              K M M
              L  M  I                M                    V C L                R I V
                 V
                                                                          α-helix
```

| EXONS | | | INTRONS | |
|---|---|---|---|---|
| GGGCCCGGGCG...EXON1 | (179 bp) | TCCGCGGGCAG/gtaagccggg....INTRON1 | (5.4 Kb) | ...tattctgtcag/ |
| GGGTATTCCC...EXON2 | (1586 bp) | ATGAACCTCG/gtaagagacc....INTRON2 | (2.5 Kb) | ...ttccgtcaag/ |
| ATTTAAATTC...EXON3 | (184 bp) | ATCAGAGAAG/gtaggtgtcc....INTRON3 | (0.4 Kb) | ...ttttctctag/ |
| ACTGCAGAGT...EXON4 | (149 bp) | ATGAACCCAA/gtatgtccta....INTRON4 | (571 bp) | ...ctcctgtcag/ |
| GTTCCAATAC...EXON5 | (145 bp) | TGATAACCAG/gtagggcgtt....INTRON5 | (127 bp) | ...tctcctttag/ |
| CCTGAAGGTA...EXON6 | (191 bp) | ACGAGCCCAA/gtgagtgtcc....INTRON6 | (6.5 Kb) | ...catcccaaag/ |
| GTTCGTTTAC...EXON7 | (226 bp) | GCCAAAGACA/gttaagacgt....INTRON7 | (255 bp) | ...ttccccacag/ |
| CTCCCTCTCA...EXON8 | (172 bp) | TTGGGAACAG/gtgagtgagg....INTRON8 | (235 bp) | ...acctccctag/ |
| GGAATCGCTG...EXON9 | (94 bp) | GCTTCATCAG/gtgagcgagg....INTRON9 | (0.6 Kb) | ...cttttgtgtag/ |
| GGTTTCTCTA...EXON10 | (123 bp) | TGTATATCAG/gtctgtacag....INTRON10 | (292 bp) | ...tgttttcag/ |
| CACTGCTCCG...EXON11 | (134 bp) | GTGGAGAACG/gtgagtgata....INTRON11 | (1.6 Kb) | ...tctcacacag/ |
| GAGAGGCAC...EXON12 | (183 bp) | GTCACATTGG/gtaaggggcc....INTRON12 | (315 bp) | ...ttgtactcag/ |
| GTTACCTTTT...EXON13 | (113 bp) | CCACCCCAAG/gtgctataac....INTRON13 | (408 bp) | ...ggattcctag/ |
| GTTGGCAGAG...EXON14 | (128 bp) | CTGTGGATGG/gtaaggaaac....INTRON14 | (173 bp) | ...gtttctctag/ |
| GCCACGGGAAT...EXON15 | (2975 bp) | CAAGAATCTG/ | | |

FIG. 6B

```
                    CREB                                   SP1
 -630  GGGGGC TGACGC CTGTAATCCCAACACTTTGGGAGGCCGAGGT GGGCGG ATCTCTTGAAA

-570  CCGGGAGTTCGAGACCACCCTGGCTAAGGTGGTGAAACCCTGTTCTTACTAAAAAACCCA

-510  AAAAAAAAAAAAAAAAAAAAAAAAGCCAGGAGTGATGGCGCTCGCCTGTAATCCCAGCTA
                                    SP1
 -450  CTCCGTAGGCTGAGGCAGGAGAATCGCTTGAACCC GGCGGG CAGAGGTTGCAGTGAACCG

-390  AGATTGCGCCATTGCACTCCAGCCTGGGCAAAAAGAGCGAGACTCCGCCTCAAAAAAAAA

-330  AAAAAAAGTACCTTCCGTAGTTCTCATGCAGCGGAGGGGTTCGACTTGTAACCGGCCTGA

-270  AACCAAGCGTGGCGCAAGATTTGCTCAAGCCCCTCCTGTTGGCCAAACTTTCCGGAGGGG
             Pu Box
 -210  AAGGCTTTCC GAGGAAA CGAAAGCGAAATTGAACCGGAGCCATCTTGGGCCCGGCGCGCA

-150  GACCCGCGGAGTTTCCCGTGCCGACGCCCCGGGGCCACTTCCAGTGCGGAGTAGCGGAGG

-90  CGTGGGGGCCTCGAGGGGCTGGCGCGGTCCAGCGGTCGGGGCAGGGTCGTGCCGCCGGCG

-30  GGTCGGGCCGGACAATGCCTCGCGGGCGCA ATG AATCCGCGGCAGGTAAGCCGGGCCGGC
                                    +1
                                       EXON 1 ——— INTRON 1
```

FIG. 7

```
Genomic  AGTTTTATGATTCTGCTTTTATGTGTCCCTTGATAACAGTGACTTAACAA  +6380
         ||||||||||||||||||||||||||||||||||||||||||||||||||
   cDNA  AGTTTTATGATTCTGCTTTTATGTGTCCCTTGATAACAGTGACTTAACAA Genomic  TATACATTCCTCATA AATAAA AAAAAAAACAAGAATCTG A TTCTTAGAAA  +6430
         |||||||||||||||||||||||||||||||||||||||
   cDNA  TATACATTCCTCATAAATAAAAAAAAAAACAAGAATCTGAn Genomic  GTTTTAAGTCCCTGGTTTTCTTGGGGGGAGGGTGGAAAATTGGGAAACAA  +6480
```

FIG. 8

SEQUENCE LISTING ( 1 ) GENERAL INFORMATION:

( i i i ) NUMBER OF SEQUENCES: 67

( 2 ) INFORMATION FOR SEQ ID NO:1:

( i ) SEQUENCE CHARACTERISTICS:
      ( A ) LENGTH: 6671 base pairs
      ( B ) TYPE: nucleic acid
      ( C ) STRANDEDNESS: double
      ( D ) TOPOLOGY: unknown ( i i ) MOLECULE TYPE: cDNA ( i x ) FEATURE:
      ( A ) NAME/KEY: CDS
      ( B ) LOCATION: 155..3832

( x i ) SEQUENCE DESCRIPTION: SEQ ID NO:1:

-continued

| | | | | | | | | | | | | | | | |
|---|---|---|---|---|---|---|---|---|---|---|---|---|---|---|---|
| CGCAGACCCG | CGGAGTTTCC | CGTGCCGACG | CCCCGGGGCC | ACTTCCAGTG | CGGAGTAGCG | | | | | | | | | | 60 |
| GAGGCGTGGG | GGCCTCGAGG | GGCTGGCGCG | GTCCAGCGGT | CGGGCCAGGG | TCGTGCCGCC | | | | | | | | | | 120 |
| GGCGGGTCGG | GCCGGACAAT | GCCTCGCGGG | CGCA ATG | AAT CCG | CGG CAG | GGG | | | | | | | | | 172 |

```
                                               Met Asn Pro Arg Gln Gly
                                                1                   5

TAT  TCC  CTC  AGC  GGA  TAC  TAC  ACC  CAT  CCA  TTT  CAA  GGC  TAT  GAG  CAC    220
Tyr  Ser  Leu  Ser  Gly  Tyr  Tyr  Thr  His  Pro  Phe  Gln  Gly  Tyr  Glu  His
               10                    15                       20

AGA  CAG  CTC  AGA  TAC  CAG  CAG  CCT  GGG  CCA  GGA  TCT  TCC  CCC  AGT  AGT    268
Arg  Gln  Leu  Arg  Tyr  Gln  Gln  Pro  Gly  Pro  Gly  Ser  Ser  Pro  Ser  Ser
               25                    30                       35

TTC  CTG  CTT  AAG  CAA  ATA  GAA  TTT  CTC  AAG  GGG  CAG  CTC  CCA  GAA  GCA    316
Phe  Leu  Leu  Lys  Gln  Ile  Glu  Phe  Leu  Lys  Gly  Gln  Leu  Pro  Glu  Ala
               40                    45                       50

CCG  GTG  ATT  GGA  AAG  CAG  ACA  CCG  TCA  CTG  CCA  CCT  TCC  CTC  CCA  GGA    364
Pro  Val  Ile  Gly  Lys  Gln  Thr  Pro  Ser  Leu  Pro  Pro  Ser  Leu  Pro  Gly
55                    60                    65                       70

CTC  CGG  CCA  AGG  TTT  CCA  GTA  CTA  CTT  GCC  TCC  AGT  ACC  AGA  GGC  AGG    412
Leu  Arg  Pro  Arg  Phe  Pro  Val  Leu  Leu  Ala  Ser  Ser  Thr  Arg  Gly  Arg
                    75                    80                       85

CAA  GTG  GAC  ATC  AGG  GGT  GTC  CCC  AGG  GGC  GTG  CAT  CTC  GGA  AGT  CAG    460
Gln  Val  Asp  Ile  Arg  Gly  Val  Pro  Arg  Gly  Val  His  Leu  Gly  Ser  Gln
               90                    95                      100

GGG  CTC  CAG  AGA  GGG  TTC  CAG  CAT  CCT  TCA  CCA  CGT  GGC  AGG  AGT  CTG    508
Gly  Leu  Gln  Arg  Gly  Phe  Gln  His  Pro  Ser  Pro  Arg  Gly  Arg  Ser  Leu
               105                  110                      115

CCA  CAG  AGA  GGT  GTT  GAT  TGC  CTT  TCC  TCA  CAT  TTC  CAG  GAA  CTG  AGT    556
Pro  Gln  Arg  Gly  Val  Asp  Cys  Leu  Ser  Ser  His  Phe  Gln  Glu  Leu  Ser
120                   125                  130

ATC  TAC  CAA  GAT  CAG  GAA  CAA  AGG  ATC  TTA  AAG  TTC  CTG  GAA  GAG  CTT    604
Ile  Tyr  Gln  Asp  Gln  Glu  Gln  Arg  Ile  Leu  Lys  Phe  Leu  Glu  Glu  Leu
135                   140                  145                      150

GGG  GAA  GGG  AAG  GCC  ACC  ACA  GCA  CAT  GAT  CTG  TCT  GGG  AAA  CTT  GGG    652
Gly  Glu  Gly  Lys  Ala  Thr  Thr  Ala  His  Asp  Leu  Ser  Gly  Lys  Leu  Gly
               155                  160                      165

ACT  CCG  AAG  AAA  GAA  ATC  AAT  CGA  GTT  TTA  TAC  TCC  CTG  GCA  AAG  AAG    700
Thr  Pro  Lys  Lys  Glu  Ile  Asn  Arg  Val  Leu  Tyr  Ser  Leu  Ala  Lys  Lys
               170                  175                      180

GGC  AAG  CTA  CAG  AAA  GAG  GCA  GGA  ACA  CCC  CCT  TTG  TGG  AAA  ATC  GCG    748
Gly  Lys  Leu  Gln  Lys  Glu  Ala  Gly  Thr  Pro  Pro  Leu  Trp  Lys  Ile  Ala
               185                  190                      195

GTC  TCC  ACT  CAG  GCT  TGG  AAC  CAG  CAC  AGC  GGA  GTG  GTA  AGA  CCA  GAC    796
Val  Ser  Thr  Gln  Ala  Trp  Asn  Gln  His  Ser  Gly  Val  Val  Arg  Pro  Asp
200                   205                  210

GGT  CAT  AGC  CAA  GGA  GCC  CCA  AAC  TCA  GAC  CCG  AGT  TTG  GAA  CCG  GAA    844
Gly  His  Ser  Gln  Gly  Ala  Pro  Asn  Ser  Asp  Pro  Ser  Leu  Glu  Pro  Glu
215                   220                  225                      230

GAC  AGA  AAC  TCC  ACA  TCT  GTC  TCA  GAA  GAT  CTT  CTT  GAG  CCT  TTT  ATT    892
Asp  Arg  Asn  Ser  Thr  Ser  Val  Ser  Glu  Asp  Leu  Leu  Glu  Pro  Phe  Ile
               235                  240                      245

GCA  GTC  TCA  GCT  CAG  GCT  TGG  AAC  CAG  CAC  AGC  GGA  GTG  GTA  AGA  CCA    940
Ala  Val  Ser  Ala  Gln  Ala  Trp  Asn  Gln  His  Ser  Gly  Val  Val  Arg  Pro
               250                  255                      260

GAC  AGT  CAT  AGC  CAA  GGA  TCC  CCA  AAC  TCA  GAC  CCA  GGT  TTG  GAA  CCT    988
Asp  Ser  His  Ser  Gln  Gly  Ser  Pro  Asn  Ser  Asp  Pro  Gly  Leu  Glu  Pro
               265                  270                      275

GAA  GAC  AGC  AAC  TCC  ACA  TCT  GCC  TTG  GAA  GAT  CCT  CTT  GAG  TTT  TTA    1036
Glu  Asp  Ser  Asn  Ser  Thr  Ser  Ala  Leu  Glu  Asp  Pro  Leu  Glu  Phe  Leu
               280                  285                      290
```

| | | | | | | | | | | | | | | | | |
|---|---|---|---|---|---|---|---|---|---|---|---|---|---|---|---|---|
| GAC | ATG | GCC | GAG | ATC | AAG | GAG | AAA | ATC | TGC | GAC | TAT | CTC | TTC | AAT | GTG | 1084 |
| Asp 295 | Met | Ala | Glu | Ile | Lys 300 | Glu | Lys | Ile | Cys | Asp 305 | Tyr | Leu | Phe | Asn | Val 310 | |
| TCT | GAC | TCC | TCT | GCC | CTG | AAT | TTG | GCT | AAA | AAT | ATT | GGC | CTT | ACC | AAG | 1132 |
| Ser | Asp | Ser | Ser | Ala 315 | Leu | Asn | Leu | Ala | Lys 320 | Asn | Ile | Gly | Leu | Thr 325 | Lys | |
| GCC | CGA | GAT | ATA | AAT | GCT | GTG | CTA | ATT | GAC | ATG | GAA | AGG | CAG | GGG | GAT | 1180 |
| Ala | Arg | Asp | Ile 330 | Asn | Ala | Val | Leu | Ile 335 | Asp | Met | Glu | Arg | Gln 340 | Gly | Asp | |
| GTC | TAT | AGA | CAA | GGG | ACA | ACC | CCT | CCC | ATA | TGG | CAT | TTG | ACA | GAC | AAG | 1228 |
| Val | Tyr | Arg 345 | Gln | Gly | Thr | Thr | Pro 350 | Pro | Ile | Trp | His | Leu 355 | Thr | Asp | Lys | |
| AAG | CGA | GAG | AGG | ATG | CAA | ATC | AAG | AGA | AAT | ACG | AAC | AGT | GTT | CCT | GAA | 1276 |
| Lys 360 | Arg | Glu | Arg | Met | Gln 365 | Ile | Lys | Arg | Asn | Thr 370 | Asn | Ser | Val | Pro | Glu | |
| ACC | GCT | CCA | GCT | GCA | ATC | CCT | GAG | ACC | AAA | AGA | AAC | GCA | GAG | TTC | CTC | 1324 |
| Thr 375 | Ala | Pro | Ala | Ala | Ile 380 | Pro | Glu | Thr | Lys | Arg 385 | Asn | Ala | Glu | Phe | Leu 390 | |
| ACC | TGT | AAT | ATA | CCC | ACA | TCA | AAT | GCC | TCA | AAT | AAC | ATG | GTA | ACC | ACA | 1372 |
| Thr | Cys | Asn | Ile | Pro 395 | Thr | Ser | Asn | Ala | Ser 400 | Asn | Asn | Met | Val | Thr 405 | Thr | |
| GAA | AAA | GTG | GAG | AAT | GGG | CAG | GAA | CCT | GTC | ATA | AAG | TTA | GAA | AAC | AGG | 1420 |
| Glu | Lys | Val | Glu | Asn 410 | Gly | Gln | Glu | Pro | Val 415 | Ile | Lys | Leu | Glu | Asn 420 | Arg | |
| CAA | GAG | GCC | AGA | CCA | GAA | CCA | GCA | AGA | CTG | AAA | CCA | CCT | GTT | CAT | TAC | 1468 |
| Gln | Glu | Ala | Arg 425 | Pro | Glu | Pro | Ala | Arg 430 | Leu | Lys | Pro | Pro | Val 435 | His | Tyr | |
| AAT | GGC | CCC | TCA | AAA | GCA | GGG | TAT | GTT | GAC | TTT | GAA | AAT | GGC | CAG | TGG | 1516 |
| Asn | Gly | Pro | Ser | Lys 440 | Ala | Gly | Tyr | Val | Asp 445 | Phe | Glu | Asn | Gly | Gln 450 | Trp | |
| GCC | ACA | GAT | GAC | ATC | CCA | GAT | GAC | TTG | AAT | AGT | ATC | CGC | GCA | GCA | CCA | 1564 |
| Ala 455 | Thr | Asp | Asp | Ile | Pro 460 | Asp | Asp | Leu | Asn | Ser 465 | Ile | Arg | Ala | Ala | Pro 470 | |
| GGT | GAG | TTT | CGA | GCC | ATC | ATG | GAG | ATG | CCC | TCC | TTC | TAC | AGT | CAT | GGC | 1612 |
| Gly | Glu | Phe | Arg | Ala 475 | Ile | Met | Glu | Met | Pro 480 | Ser | Phe | Tyr | Ser | His 485 | Gly | |
| TTG | CCA | CGG | TGT | TCA | CCC | TAC | AAG | AAA | CTG | ACA | GAG | TGC | CAG | CTG | AAG | 1660 |
| Leu | Pro | Arg | Cys 490 | Ser | Pro | Tyr | Lys | Lys 495 | Leu | Thr | Glu | Cys | Gln 500 | Leu | Lys | |
| AAC | CCC | ATC | AGC | GGG | CTG | TTA | GAA | TAT | GCC | CAG | TTC | GCT | AGT | CAA | ACC | 1708 |
| Asn | Pro | Ile | Ser 505 | Gly | Leu | Leu | Glu | Tyr 510 | Ala | Gln | Phe | Ala | Ser 515 | Gln | Thr | |
| TGT | GAG | TTC | AAC | ATG | ATA | GAG | CAG | AGT | GGA | CCA | CCC | CAT | GAA | CCT | CGA | 1756 |
| Cys | Glu 520 | Phe | Asn | Met | Ile | Glu 525 | Gln | Ser | Gly | Pro | Pro 530 | His | Glu | Pro | Arg | |
| TTT | AAA | TTC | CAG | GTT | GTC | ATC | AAT | GGC | CGA | GAG | TTT | CCC | CCA | GCT | GAA | 1804 |
| Phe | Lys | Phe | Gln | Val 540 | Val | Ile | Asn | Gly | Arg 545 | Glu | Phe | Pro | Pro | Ala 550 | Glu | |
| 535 | | | | | | | | | | | | | | | | |
| GCT | GGA | AGC | AAG | AAA | GTG | GCC | AAG | CAG | GAT | GCA | GCT | ATG | AAA | GCC | ATG | 1852 |
| Ala | Gly | Ser | Lys | Lys 555 | Val | Ala | Lys | Gln | Asp 560 | Ala | Ala | Met | Lys | Ala 565 | Met | |
| ACA | ATT | CTG | CTA | GAG | GAA | GCC | AAA | GCC | AAG | GAC | AGT | GGA | AAA | TCA | GAA | 1900 |
| Thr | Ile | Leu | Leu 570 | Glu | Glu | Ala | Lys | Ala 575 | Lys | Asp | Ser | Gly | Lys 580 | Ser | Glu | |
| GAA | TCA | TCC | CAC | TAT | TCC | ACA | GAG | AAA | GAA | TCA | GAG | AAG | ACT | GCA | GAG | 1948 |
| Glu | Ser | Ser 585 | His | Tyr | Ser | Thr | Glu 590 | Lys | Glu | Ser | Glu | Lys 595 | Thr | Ala | Glu | |
| TCC | CAG | ACC | CCC | ACC | CCT | TCA | GCC | ACA | TCC | TTC | TTT | TCT | GGG | AAG | AGC | 1996 |
| Ser | Gln | Thr 600 | Pro | Thr | Pro | Ser | Ala 605 | Thr | Ser | Phe | Phe | Ser 610 | Gly | Lys | Ser | |

```
CCC GTC ACC ACA CTG CTT GAG TGT ATG CAC AAA TTG GGG AAC TCC TGC    2044
Pro Val Thr Thr Leu Leu Glu Cys Met His Lys Leu Gly Asn Ser Cys
615                 620                 625                 630

GAA TTC CGT CTC CTG TCC AAA GAA GGC CCT GCC CAT GAA CCC AAG TTC    2092
Glu Phe Arg Leu Leu Ser Lys Glu Gly Pro Ala His Glu Pro Lys Phe
                    635                 640                 645

CAA TAC TGT GTT GCA GTG GGA GCC CAA ACT TTC CCC AGT GTG AGT GCT    2140
Gln Tyr Cys Val Ala Val Gly Ala Gln Thr Phe Pro Ser Val Ser Ala
                650                 655                 660

CCC AGC AAG AAA GTG GCA AAG CAG ATG GCC GCA GAG GAA GCC ATG AAG    2188
Pro Ser Lys Lys Val Ala Lys Gln Met Ala Ala Glu Glu Ala Met Lys
            665                 670                 675

GCC CTG CAT GGG GAG GCG ACC AAC TCC ATG GCT TCT GAT AAC CAG CCT    2236
Ala Leu His Gly Glu Ala Thr Asn Ser Met Ala Ser Asp Asn Gln Pro
        680                 685                 690

GAA GGT ATG ATC TCA GAG TCA CTT GAT AAC TTG GAA TCC ATG ATG CCC    2284
Glu Gly Met Ile Ser Glu Ser Leu Asp Asn Leu Glu Ser Met Met Pro
695                 700                 705                 710

AAC AAG GTC AGG AAG ATT GGC GAG CTC GTG AGA TAC CTG AAC ACC AAC    2332
Asn Lys Val Arg Lys Ile Gly Glu Leu Val Arg Tyr Leu Asn Thr Asn
                715                 720                 725

CCT GTG GGT GGC CTT TTG GAG TAC GCC CGC TCC CAT GGC TTT GCT GCT    2380
Pro Val Gly Gly Leu Leu Glu Tyr Ala Arg Ser His Gly Phe Ala Ala
                730                 735                 740

GAA TTC AAG TTG GTC GAC CAG TCC GGA CCT CCT CAC GAG CCC AAG TTC    2428
Glu Phe Lys Leu Val Asp Gln Ser Gly Pro Pro His Glu Pro Lys Phe
        745                 750                 755

GTT TAC CAA GCA AAA GTT GGG GGT CGC TGG TTC CCA GCC GTC TGC GCA    2476
Val Tyr Gln Ala Lys Val Gly Gly Arg Trp Phe Pro Ala Val Cys Ala
760                 765                 770

CAC AGC AAG AAG CAA GGC AAG CAG GAA GCA GCA GAT GCG GCT CTC CGT    2524
His Ser Lys Lys Gln Gly Lys Gln Glu Ala Ala Asp Ala Ala Leu Arg
775                 780                 785                 790

GTC TTG ATT GGG GAG AAC GAG AAG GCA GAA CGC ATG GGT TTC ACA GAG    2572
Val Leu Ile Gly Glu Asn Glu Lys Ala Glu Arg Met Gly Phe Thr Glu
                795                 800                 805

GTA ACC CCA GTG ACA GGG GCC AGT CTC AGA AGA ACT ATG CTC CTC CTC    2620
Val Thr Pro Val Thr Gly Ala Ser Leu Arg Arg Thr Met Leu Leu Leu
            810                 815                 820

TCA AGG TCC CCA GAA GCA CAG CCA AAG ACA CTC CCT CTC ACT GGC AGC    2668
Ser Arg Ser Pro Glu Ala Gln Pro Lys Thr Leu Pro Leu Thr Gly Ser
        825                 830                 835

ACC TTC CAT GAC CAG ATA GCC ATG CTG AGC CAC CGG TGC TTC AAC ACT    2716
Thr Phe His Asp Gln Ile Ala Met Leu Ser His Arg Cys Phe Asn Thr
840                 845                 850

CTG ACT AAC AGC TTC CAG CCC TCC TTG CTC GGC CGC AAG ATT CTG GCC    2764
Leu Thr Asn Ser Phe Gln Pro Ser Leu Leu Gly Arg Lys Ile Leu Ala
855                 860                 865                 870

GCC ATC ATT ATG AAA AAA GAC TCT GAG GAC ATG GGT GTC GTC GTC AGC    2812
Ala Ile Ile Met Lys Lys Asp Ser Glu Asp Met Gly Val Val Val Ser
                875                 880                 885

TTG GGA ACA GGG AAT CGC TGT GTG AAA GGA GAT TCT CTC AGC CTA AAA    2860
Leu Gly Thr Gly Asn Arg Cys Val Lys Gly Asp Ser Leu Ser Leu Lys
                890                 895                 900

GGA GAA ACT GTC AAT GAC TGC CAT GCA GAA ATA ATC TCC CGG AGA GGC    2908
Gly Glu Thr Val Asn Asp Cys His Ala Glu Ile Ile Ser Arg Arg Gly
            905                 910                 915

TTC ATC AGG TTT CTC TAC AGT GAG TTA ATG AAA TAC AAC TCC CAG ACT    2956
Phe Ile Arg Phe Leu Tyr Ser Glu Leu Met Lys Tyr Asn Ser Gln Thr
        920                 925                 930
```

-continued

| | |
|---|---|
| GCG AAG GAT AGT ATA TTT GAA CCT GCT AAG GGA GGA GAA AAG CTC CAA<br>Ala Lys Asp Ser Ile Phe Glu Pro Ala Lys Gly Gly Glu Lys Leu Gln<br>935                       940                     945                     950 | 3004 |
| ATA AAA AAG ACT GTG TCA TTC CAT CTG TAT ATC AGC ACT GCT CCG TGT<br>Ile Lys Lys Thr Val Ser Phe His Leu Tyr Ile Ser Thr Ala Pro Cys<br>                955                     960                     965 | 3052 |
| GGA GAT GGC GCC CTC TTT GAC AAG TCC TGC AGC GAC CGT GCT ATG GAA<br>Gly Asp Gly Ala Leu Phe Asp Lys Ser Cys Ser Asp Arg Ala Met Glu<br>970                         975                     980 | 3100 |
| AGC ACA GAA TCC CGC CAC TAC CCT GTC TTC GAG AAT CCC AAA CAA GGA<br>Ser Thr Glu Ser Arg His Tyr Pro Val Phe Glu Asn Pro Lys Gln Gly<br>985                       990                     995 | 3148 |
| AAG CTC CGC ACC AAG GTG GAG AAC GGA GAA GGC ACA ATC CCT GTG GAA<br>Lys Leu Arg Thr Lys Val Glu Asn Gly Glu Gly Thr Ile Pro Val Glu<br>1000                       1005                   1010 | 3196 |
| TCC AGT GAC ATT GTG CCT ACG TGG GAT GGC ATT CGG CTC GGG GAG AGA<br>Ser Ser Asp Ile Val Pro Thr Trp Asp Gly Ile Arg Leu Gly Glu Arg<br>1015                     1020                   1025                   1030 | 3244 |
| CTC CGT ACC ATG TCC TGT AGT GAC AAA ATC CTA CGC TGG AAC GTG CTG<br>Leu Arg Thr Met Ser Cys Ser Asp Lys Ile Leu Arg Trp Asn Val Leu<br>                1035                   1040                   1045 | 3292 |
| GGC CTG CAA GGG GCA CTG TTG ACC CAC TTC CTG CAG CCC ATT TAT CTC<br>Gly Leu Gln Gly Ala Leu Leu Thr His Phe Leu Gln Pro Ile Tyr Leu<br>         1050                   1055                   1060 | 3340 |
| AAA TCT GTC ACA TTG GGT TAC CTT TTC AGC CAA GGG CAT CTG ACC CGT<br>Lys Ser Val Thr Leu Gly Tyr Leu Phe Ser Gln Gly His Leu Thr Arg<br>        1065                   1070                   1075 | 3388 |
| GCT ATT TGC TGT CGT GTG ACA AGA GAT GGG AGT GCA TTT GAG GAT GGA<br>Ala Ile Cys Cys Arg Val Thr Arg Asp Gly Ser Ala Phe Glu Asp Gly<br>1080                     1085                   1090 | 3436 |
| CTA CGA CAT CCC TTT ATT GTC AAC CAC CCC AAG GTT GGC AGA GTC AGC<br>Leu Arg His Pro Phe Ile Val Asn His Pro Lys Val Gly Arg Val Ser<br>1095                     1100                   1105                   1110 | 3484 |
| ATA TAT GAT TCC AAA AGG CAA TCC GGG AAG ACT AAG GAG ACA AGC GTC<br>Ile Tyr Asp Ser Lys Arg Gln Ser Gly Lys Thr Lys Glu Thr Ser Val<br>                1115                   1120                   1125 | 3532 |
| AAC TGG TGT CTG GCT GAT GGC TAT GAC CTG GAG ATC CTG GAC GGT ACC<br>Asn Trp Cys Leu Ala Asp Gly Tyr Asp Leu Glu Ile Leu Asp Gly Thr<br>1130                     1135                   1140 | 3580 |
| AGA GGC ACT GTG GAT GGG CCA CGG AAT GAA TTG TCC CGG GTC TCC AAA<br>Arg Gly Thr Val Asp Gly Pro Arg Asn Glu Leu Ser Arg Val Ser Lys<br>1145                     1150                   1155 | 3628 |
| AAG AAC ATT TTT CTT CTA TTT AAG AAG CTC TGC TCC TTC CGT TAC CGC<br>Lys Asn Ile Phe Leu Leu Phe Lys Lys Leu Cys Ser Phe Arg Tyr Arg<br>1160                     1165                   1170 | 3676 |
| AGG GAT CTA CTG AGA CTC TCC TAT GGT GAG GCC AAG AAA GCT GCC CGT<br>Arg Asp Leu Leu Arg Leu Ser Tyr Gly Glu Ala Lys Lys Ala Ala Arg<br>1175                     1180                   1185                   1190 | 3724 |
| GAC TAC GAG ACG GCC AAG AAC TAC TTC AAA AAA GGC CTG AAG GAT ATG<br>Asp Tyr Glu Thr Ala Lys Asn Tyr Phe Lys Lys Gly Leu Lys Asp Met<br>                1195                   1200                   1205 | 3772 |
| GGC TAT GGG AAC TGG ATT AGC AAA CCC CAG GAG GAA AAG AAC TTT TAT<br>Gly Tyr Gly Asn Trp Ile Ser Lys Pro Gln Glu Glu Lys Asn Phe Tyr<br>                1210                   1215                   1220 | 3820 |
| CTC TGC CCA GTA TAGTATGCTC CAGTGACAGA TGGATTAGGG TGTGTCATAC<br>Leu Cys Pro Val<br>               1225 | 3872 |
| TAGGGTGTGA GAGAGGTAGG TCGTAGCATT CCTCATCACA TGGTCAGGGG ATTTTTTTTT | 3932 |
| CTCCTTTTTT TTTTCTTTTT AAGCCATAAT TGGTGATACT GAAAACTTTG GGTTCCCATT | 3992 |

-continued

| | | | | | |
|---|---|---|---|---|---|
| TATCCTGCTT | TCTTTGGGAT | TGCTAGGCAA | GGTCTGGCCA | GGCCCCCCTT | TTTTCCCCCA | 4052 |
| AGTGAAGAGG | CAGAAACCTA | AGAAGTTATC | TTTTCTTTCT | ACCCAAAGCA | TACATAGTCA | 4112 |
| CTGAGCACCT | GCGGTCCATT | TCCTCTTAAA | AGTTTTGTTT | TGATTTGTTT | CCATTTCCTT | 4172 |
| TCCCTTTGTG | TTTGCTACAC | TGACCTCTTG | CGGTCTTGAT | TAGGTTTCAG | TCAACTCTGG | 4232 |
| ATCATGTCAG | GGACTGATAA | TTTCATTTGT | GGATTACGCA | GACCCCTCTA | CTTCCCTCT | 4292 |
| TTCCCTTCTG | AGATTCTTTC | CTTGTGATCT | GAATGTCTCC | TTTTCCCCT | CAGAGGGCAA | 4352 |
| AGAGGTGAAC | ATAAAGGATT | TGGTGAAACA | TTTGTAAGGG | TAGGAGTTGA | AAACTGCAGT | 4412 |
| TCCCAGTGCC | ACGGAAGTGT | GATTGGAGCC | TGCAGATAAT | GCCCAGCCAT | CCTCCCATCC | 4472 |
| TGCACTTTAG | CCAGCTGCAG | GGCGGGCAAG | GCAAGGAAAG | CTGCTTCCCT | GGAAGTGTAT | 4532 |
| CACTTTCTCC | GGCAGCTGGG | AAGTCTAGAA | CCAGCCAGAC | TGGGTTAAGG | GAGCTGCTCA | 4592 |
| AGCAATAGCA | GAGGTTTCAC | CCGGCAGGAT | GACACAGACC | ACTTCCCAGG | GAGCACGGGC | 4652 |
| ATGCCTTGGA | ATATTGCCAA | GCTTCCAGCT | GCCTCTTCTC | CTAAAGCATT | CCTAGGAATA | 4712 |
| TTTTCCCCGC | CAATGCTGGG | CGTACACCCT | AGCCAACGGG | ACAAATCCTA | GAGGGTATAA | 4772 |
| AATCATCTCT | GCTCAGATAA | TCATGACTTA | GCAAGAATAA | GGGCAAAAAA | TCCTGTTGGC | 4832 |
| TTAACGTCAC | TGTTCCACCC | GGTGTAATAT | CTCTCATGAC | AGTGACACCA | AGGGAAGTTG | 4892 |
| ACTAAGTCAC | ATGTAAATTA | GGAGTGTTTT | AAAGAATGCC | ATAGATGTTG | ATTCTTAACT | 4952 |
| GCTACAGATA | ACCTGTAATT | GAGCAGATTT | AAAATTCAGG | CATACTTTTC | CATTTATCCA | 5012 |
| AGTGCTTTCA | TTTTCCAGA | TGGCTTCAGA | AGTAGGCTCG | TGGGCAGGGC | GCAGACCTGA | 5072 |
| TCTTTATAGG | GTTGACATAG | AAAGCAGTAG | TTGTGGGTGA | AAGGGCAGGT | TGTCTTCAAA | 5132 |
| CTCTGTGAGG | TAGAATCCTT | TGTCTATACC | TCCATGAACA | TTGACTCGTG | TGTTCAGAGC | 5192 |
| CTTTGGCCTC | TCTGTGGAGT | CTGGCTCTCT | GGCTCCTGTG | CATTCTTTGA | ATAGTCACTC | 5252 |
| GTAAAAACTG | TCAGTGCTTG | AAACTGTTTC | CTTTACTCAT | GTTGAAGGGA | CTTTGTTGGC | 5312 |
| TTTTAGAGTG | TTGGTCATGA | CTCCAAGAGC | AGAGCAGGGA | AGAGCCCAAG | CATAGACTTG | 5372 |
| GTGCCGTGGT | GATGGCTGCA | GTCCAGTTTT | GTGATGCTGC | TTTTACGTGT | CCCTCGATAA | 5432 |
| CAGTCAGCTA | GACACACTCA | GGAGGACTAC | TGAGGCTCTG | CGACCTTCAG | GAGCTGAGCC | 5492 |
| TGCCTCTCTC | CTTTAGATGA | CAGACCTTCA | TCTGGGAACG | TGCTGAGCCA | GCACCCTCAG | 5552 |
| ATGATTTCCC | TCCAAACTGC | TGACTAGGTC | ATCCTCTGTC | TGGTAGAGAC | ATTCACATCT | 5612 |
| TTGCTTTTAT | TCTATGCTCT | CTGTACTTTT | GACCAAAAAT | TGACCAAAGT | AAGAAAATGC | 5672 |
| AAGTTCTAAA | AATAGACTAA | GGATGCCTTT | GCAGAACACC | AAAGCATCCC | AAGGAACTGG | 5732 |
| TAGGGAAGTG | GCGCCTGTCT | CCTGGAGTGG | AAGAGGCCTG | CTCCCTGCTC | TGGGTCTGCT | 5792 |
| GGGGGCACAG | TAAATCAGTC | TTGGCACCCA | CATCCAGGGC | AGAGAGGTCT | GTGGTTCTCA | 5852 |
| GCATCAGAAG | GCAGCGCAGC | CCCTCTCCTC | TTCAGGCTAC | AGGGTTGTCA | CCTGCTGAGT | 5912 |
| CCTCAGGTTG | TTTGGCCTCT | CTGGTCCATC | TTGGGCATTA | GGTTCTCCAG | CAGAGCTCTG | 5972 |
| GCCAGCTGCC | TCTTCTTTAA | CTGGGAACAC | AGGCTCTCAC | AAGATCAGAA | CCCCCACTCA | 6032 |
| CCCCCAAGAT | CTTATCTAGC | AAGCCTGTAG | TATTCAGTTT | CTGTTGTAGG | AAGAGAGCGA | 6092 |
| GGCATCCCTG | AATTCCACGC | ATCGCTGGA | AACGAGCCGT | GTCAGATCGC | ACATCCCTGC | 6152 |
| GCCCCCATGC | CCCTCTGAGT | CACACAGGAC | AGAGGAGGCA | GAGCTTCTGC | CCACTGTTAT | 6212 |
| CTTCACTTTC | TTTGTCCAGT | CTTTTGTTTT | TAATAAGCAG | TGACCCTCCC | TACTCTTCTT | 6272 |
| TTTAATGATT | TTTGTAGTTG | ATTTGTCTGA | ACTGTGGCTA | CTGTGCATTC | CTTGAATAAT | 6332 |
| CACTTGTAAA | AATTGTCAGT | GCTTGAAGCT | GTTTCCTTTA | CTCACATTGA | AGGGACTTCG | 6392 |

| | | | | | |
|---|---|---|---|---|---|
|TTGGTTTTTT|GGAGTCTTGG|TTGTGACTCC|AAGAGCAGAG|TGAGGAAGAC|CCCCAAGCAT 6452|
|AGACTCGGGT|ACTGTGATGA|TGGCTGCAGT|CCAGTTTTAT|GATTCTGCTT|TTATGTGTCC 6512|
|CTTGATAACA|GTGACTTAAC|AATATACATT|CCTCATAAAT|AAAAAAAAAA|CAAGAATCTG 6572|
|AAAAAAAAAA|AAAAAAAAAA|AAAAAAAAAA|AAAAAAAAAA|AAAAAAAAAA|AAAAAAAAAA 6632|
|AAAAAAAAAA|AAAAAAAAAA|AAAAAAAAAA|AAAAAAAA|  | 6671|

( 2 ) INFORMATION FOR SEQ ID NO:2:

( i ) SEQUENCE CHARACTERISTICS:
        ( A ) LENGTH: 1226 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Asn Pro Arg Gln Gly Tyr Ser Leu Ser Gly Tyr Tyr Thr His Pro
 1               5                  10                  15
Phe Gln Gly Tyr Glu His Arg Gln Leu Arg Tyr Gln Gln Pro Gly Pro
            20                  25                  30
Gly Ser Ser Pro Ser Ser Phe Leu Leu Lys Gln Ile Glu Phe Leu Lys
        35                  40                  45
Gly Gln Leu Pro Glu Ala Pro Val Ile Gly Lys Gln Thr Pro Ser Leu
    50                  55                  60
Pro Pro Ser Leu Pro Gly Leu Arg Pro Arg Phe Pro Val Leu Leu Ala
65                  70                  75                  80
Ser Ser Thr Arg Gly Arg Gln Val Asp Ile Arg Gly Val Pro Arg Gly
                85                  90                  95
Val His Leu Gly Ser Gln Gly Leu Gln Arg Gly Phe Gln His Pro Ser
            100                 105                 110
Pro Arg Gly Arg Ser Leu Pro Gln Arg Gly Val Asp Cys Leu Ser Ser
        115                 120                 125
His Phe Gln Glu Leu Ser Ile Tyr Gln Asp Gln Glu Gln Arg Ile Leu
    130                 135                 140
Lys Phe Leu Glu Glu Leu Gly Glu Gly Lys Ala Thr Thr Ala His Asp
145                 150                 155                 160
Leu Ser Gly Lys Leu Gly Thr Pro Lys Lys Glu Ile Asn Arg Val Leu
                165                 170                 175
Tyr Ser Leu Ala Lys Lys Gly Lys Leu Gln Lys Glu Ala Gly Thr Pro
            180                 185                 190
Pro Leu Trp Lys Ile Ala Val Ser Thr Gln Ala Trp Asn Gln His Ser
        195                 200                 205
Gly Val Val Arg Pro Asp Gly His Ser Gln Gly Ala Pro Asn Ser Asp
    210                 215                 220
Pro Ser Leu Glu Pro Glu Asp Arg Asn Ser Thr Ser Val Ser Glu Asp
225                 230                 235                 240
Leu Leu Glu Pro Phe Ile Ala Val Ser Ala Gln Ala Trp Asn Gln His
                245                 250                 255
Ser Gly Val Val Arg Pro Asp Ser His Ser Gln Gly Ser Pro Asn Ser
            260                 265                 270
Asp Pro Gly Leu Glu Pro Glu Asp Ser Asn Ser Thr Ser Ala Leu Glu
        275                 280                 285
Asp Pro Leu Glu Phe Leu Asp Met Ala Glu Ile Lys Glu Lys Ile Cys
    290                 295                 300
Asp Tyr Leu Phe Asn Val Ser Asp Ser Ser Ala Leu Asn Leu Ala Lys
```

-continued

```
305                         310                         315                         320
Asn  Ile  Gly  Leu  Thr  Lys  Ala  Arg  Asp  Ile  Asn  Ala  Val  Leu  Ile  Asp
                    325                         330                         335
Met  Glu  Arg  Gln  Gly  Asp  Val  Tyr  Arg  Gln  Gly  Thr  Thr  Pro  Pro  Ile
               340                         345                         350
Trp  His  Leu  Thr  Asp  Lys  Lys  Arg  Glu  Arg  Met  Gln  Ile  Lys  Arg  Asn
          355                         360                         365
Thr  Asn  Ser  Val  Pro  Glu  Thr  Ala  Pro  Ala  Ala  Ile  Pro  Glu  Thr  Lys
     370                         375                         380
Arg  Asn  Ala  Glu  Phe  Leu  Thr  Cys  Asn  Ile  Pro  Thr  Ser  Asn  Ala  Ser
385                         390                         395                         400
Asn  Asn  Met  Val  Thr  Thr  Glu  Lys  Val  Glu  Asn  Gly  Gln  Glu  Pro  Val
                    405                         410                         415
Ile  Lys  Leu  Glu  Asn  Arg  Gln  Glu  Ala  Arg  Pro  Glu  Pro  Ala  Arg  Leu
               420                         425                         430
Lys  Pro  Pro  Val  His  Tyr  Asn  Gly  Pro  Ser  Lys  Ala  Gly  Tyr  Val  Asp
          435                         440                         445
Phe  Glu  Asn  Gly  Gln  Trp  Ala  Thr  Asp  Asp  Ile  Pro  Asp  Asp  Leu  Asn
     450                         455                         460
Ser  Ile  Arg  Ala  Ala  Pro  Gly  Glu  Phe  Arg  Ala  Ile  Met  Glu  Met  Pro
465                         470                         475                         480
Ser  Phe  Tyr  Ser  His  Gly  Leu  Pro  Arg  Cys  Ser  Pro  Tyr  Lys  Lys  Leu
                    485                         490                         495
Thr  Glu  Cys  Gln  Leu  Lys  Asn  Pro  Ile  Ser  Gly  Leu  Leu  Glu  Tyr  Ala
               500                         505                         510
Gln  Phe  Ala  Ser  Gln  Thr  Cys  Glu  Phe  Asn  Met  Ile  Glu  Gln  Ser  Gly
          515                         520                         525
Pro  Pro  His  Glu  Pro  Arg  Phe  Lys  Phe  Gln  Val  Val  Ile  Asn  Gly  Arg
     530                         535                         540
Glu  Phe  Pro  Pro  Ala  Glu  Ala  Gly  Ser  Lys  Lys  Val  Ala  Lys  Gln  Asp
545                         550                         555                         560
Ala  Ala  Met  Lys  Ala  Met  Thr  Ile  Leu  Leu  Glu  Glu  Ala  Lys  Ala  Lys
                    565                         570                         575
Asp  Ser  Gly  Lys  Ser  Glu  Glu  Ser  Ser  His  Tyr  Ser  Thr  Glu  Lys  Glu
               580                         585                         590
Ser  Glu  Lys  Thr  Ala  Glu  Ser  Gln  Thr  Pro  Thr  Pro  Ser  Ala  Thr  Ser
          595                         600                         605
Phe  Phe  Ser  Gly  Lys  Ser  Pro  Val  Thr  Thr  Leu  Leu  Glu  Cys  Met  His
     610                         615                         620
Lys  Leu  Gly  Asn  Ser  Cys  Glu  Phe  Arg  Leu  Leu  Ser  Lys  Glu  Gly  Pro
625                         630                         635                         640
Ala  His  Glu  Pro  Lys  Phe  Gln  Tyr  Cys  Val  Ala  Val  Gly  Ala  Gln  Thr
                    645                         650                         655
Phe  Pro  Ser  Val  Ser  Ala  Pro  Ser  Lys  Lys  Val  Ala  Lys  Gln  Met  Ala
               660                         665                         670
Ala  Glu  Glu  Ala  Met  Lys  Ala  Leu  His  Gly  Glu  Ala  Thr  Asn  Ser  Met
          675                         680                         685
Ala  Ser  Asp  Asn  Gln  Pro  Glu  Gly  Met  Ile  Ser  Glu  Ser  Leu  Asp  Asn
     690                         695                         700
Leu  Glu  Ser  Met  Met  Pro  Asn  Lys  Val  Arg  Lys  Ile  Gly  Glu  Leu  Val
705                         710                         715                         720
Arg  Tyr  Leu  Asn  Thr  Asn  Pro  Val  Gly  Gly  Leu  Leu  Glu  Tyr  Ala  Arg
                    725                         730                         735
```

-continued

```
Ser  His  Gly  Phe  Ala  Ala  Glu  Phe  Lys  Leu  Val  Asp  Gln  Ser  Gly  Pro
               740                 745                      750

Pro  His  Glu  Pro  Lys  Phe  Val  Tyr  Gln  Ala  Lys  Val  Gly  Gly  Arg  Trp
               755                 760                      765

Phe  Pro  Ala  Val  Cys  Ala  His  Ser  Lys  Lys  Gln  Gly  Lys  Gln  Glu  Ala
               770                 775                      780

Ala  Asp  Ala  Ala  Leu  Arg  Val  Leu  Ile  Gly  Glu  Asn  Glu  Lys  Ala  Glu
785                      790                 795                           800

Arg  Met  Gly  Phe  Thr  Glu  Val  Thr  Pro  Val  Thr  Gly  Ala  Ser  Leu  Arg
                    805                 810                      815

Arg  Thr  Met  Leu  Leu  Leu  Ser  Arg  Ser  Pro  Glu  Ala  Gln  Pro  Lys  Thr
               820                 825                      830

Leu  Pro  Leu  Thr  Gly  Ser  Thr  Phe  His  Asp  Gln  Ile  Ala  Met  Leu  Ser
               835                 840                      845

His  Arg  Cys  Phe  Asn  Thr  Leu  Thr  Asn  Ser  Phe  Gln  Pro  Ser  Leu  Leu
     850                      855                 860

Gly  Arg  Lys  Ile  Leu  Ala  Ala  Ile  Ile  Met  Lys  Lys  Asp  Ser  Glu  Asp
865                      870                 875                           880

Met  Gly  Val  Val  Val  Ser  Leu  Gly  Thr  Gly  Asn  Arg  Cys  Val  Lys  Gly
                    885                 890                      895

Asp  Ser  Leu  Ser  Leu  Lys  Gly  Glu  Thr  Val  Asn  Asp  Cys  His  Ala  Glu
               900                 905                      910

Ile  Ile  Ser  Arg  Arg  Gly  Phe  Ile  Arg  Phe  Leu  Tyr  Ser  Glu  Leu  Met
               915                 920                      925

Lys  Tyr  Asn  Ser  Gln  Thr  Ala  Lys  Asp  Ser  Ile  Phe  Glu  Pro  Ala  Lys
     930                      935                 940

Gly  Gly  Glu  Lys  Leu  Gln  Ile  Lys  Lys  Thr  Val  Ser  Phe  His  Leu  Tyr
945                      950                 955                           960

Ile  Ser  Thr  Ala  Pro  Cys  Gly  Asp  Gly  Ala  Leu  Phe  Asp  Lys  Ser  Cys
                    965                 970                      975

Ser  Asp  Arg  Ala  Met  Glu  Ser  Thr  Glu  Ser  Arg  His  Tyr  Pro  Val  Phe
               980                 985                      990

Glu  Asn  Pro  Lys  Gln  Gly  Lys  Leu  Arg  Thr  Lys  Val  Glu  Asn  Gly  Glu
     995                      1000                1005

Gly  Thr  Ile  Pro  Val  Glu  Ser  Ser  Asp  Ile  Val  Pro  Thr  Trp  Asp  Gly
     1010                     1015                1020

Ile  Arg  Leu  Gly  Glu  Arg  Leu  Arg  Thr  Met  Ser  Cys  Ser  Asp  Lys  Ile
1025                     1030                1035                          1040

Leu  Arg  Trp  Asn  Val  Leu  Gly  Leu  Gln  Gly  Ala  Leu  Leu  Thr  His  Phe
                    1045                1050                     1055

Leu  Gln  Pro  Ile  Tyr  Leu  Lys  Ser  Val  Thr  Leu  Gly  Tyr  Leu  Phe  Ser
               1060                1065                     1070

Gln  Gly  His  Leu  Thr  Arg  Ala  Ile  Cys  Cys  Arg  Val  Thr  Arg  Asp  Gly
               1075                1080                     1085

Ser  Ala  Phe  Glu  Asp  Gly  Leu  Arg  His  Pro  Phe  Ile  Val  Asn  His  Pro
     1090                     1095                1100

Lys  Val  Gly  Arg  Val  Ser  Ile  Tyr  Asp  Ser  Lys  Arg  Gln  Ser  Gly  Lys
1105                     1110                1115                          1120

Thr  Lys  Glu  Thr  Ser  Val  Asn  Trp  Cys  Leu  Ala  Asp  Gly  Tyr  Asp  Leu
                    1125                1130                     1135

Glu  Ile  Leu  Asp  Gly  Thr  Arg  Gly  Thr  Val  Asp  Gly  Pro  Arg  Asn  Glu
               1140                1145                     1150

Leu  Ser  Arg  Val  Ser  Lys  Lys  Asn  Ile  Phe  Leu  Leu  Phe  Lys  Lys  Leu
               1155                1160                     1165
```

-continued

```
Cys Ser Phe Arg Tyr Arg Arg Asp Leu Leu Arg Leu Ser Tyr Gly Glu
    1170            1175                1180

Ala Lys Lys Ala Ala Arg Asp Tyr Glu Thr Ala Lys Asn Tyr Phe Lys
1185            1190                1195                1200

Lys Gly Leu Lys Asp Met Gly Tyr Gly Asn Trp Ile Ser Lys Pro Gln
            1205                1210                1215

Glu Glu Lys Asn Phe Tyr Leu Cys Pro Val
        1220                1225
```

(2) INFORMATION FOR SEQ ID NO:3:

(i) SEQUENCE CHARACTERISTICS:
(A) LENGTH: 72 amino acids
(B) TYPE: amino acid
(C) STRANDEDNESS:
(D) TOPOLOGY: unknown (ii) MOLECULE TYPE: protein (xi) SEQUENCE DESCRIPTION: SEQ ID NO:3:

```
Lys Asn Pro Ile Ser Gly Leu Leu Glu Tyr Ala Gln Phe Ala Ser Gln
1               5                   10                  15

Thr Cys Glu Phe Asn Met Ile Glu Gln Ser Gly Pro Pro His Glu Pro
            20                  25                  30

Arg Phe Lys Phe Gln Val Val Ile Asn Gly Arg Glu Phe Pro Pro Ala
        35                  40                  45

Glu Ala Gly Ser Lys Lys Val Ala Lys Gln Asp Ala Ala Met Lys Ala
    50                  55                  60

Met Thr Ile Leu Leu Glu Glu Ala
65                  70
```

(2) INFORMATION FOR SEQ ID NO:4:

(i) SEQUENCE CHARACTERISTICS:
(A) LENGTH: 72 amino acids
(B) TYPE: amino acid
(C) STRANDEDNESS:
(D) TOPOLOGY: unknown (ii) MOLECULE TYPE: protein (xi) SEQUENCE DESCRIPTION: SEQ ID NO:4:

```
Lys Ser Pro Val Thr Thr Leu Leu Glu Cys Met His Lys Leu Gly Asn
1               5                   10                  15

Ser Cys Glu Phe Arg Leu Leu Ser Lys Glu Gly Pro Ala His Glu Pro
            20                  25                  30

Lys Phe Gln Tyr Cys Val Ala Val Gly Ala Gln Thr Phe Pro Ser Val
        35                  40                  45

Ser Ala Pro Ser Lys Lys Val Ala Lys Gln Met Ala Ala Glu Glu Ala
    50                  55                  60

Met Lys Ala Leu His Gly Glu Ala
65                  70
```

(2) INFORMATION FOR SEQ ID NO:5:

(i) SEQUENCE CHARACTERISTICS:
(A) LENGTH: 72 amino acids
(B) TYPE: amino acid
(C) STRANDEDNESS:
(D) TOPOLOGY: unknown (ii) MOLECULE TYPE: protein ( x i ) SEQUENCE DESCRIPTION: SEQ ID NO:5:

| Thr | Asn | Pro | Val | Gly | Gly | Leu | Leu | Glu | Tyr | Ala | Arg | Ser | His | Gly | Phe |
| 1 | | | | 5 | | | | | 10 | | | | | 15 | |

| Ala | Ala | Glu | Phe | Lys | Leu | Val | Asp | Gln | Ser | Gly | Pro | Pro | His | Glu | Pro |
| | | | | 20 | | | | | 25 | | | | | 30 | |

| Lys | Phe | Val | Tyr | Gln | Ala | Lys | Val | Gly | Gly | Arg | Trp | Phe | Pro | Ala | Val |
| | | | 35 | | | | | 40 | | | | | 45 | | |

| Cys | Ala | His | Ser | Lys | Lys | Gln | Gly | Lys | Gln | Glu | Ala | Ala | Asp | Ala | Ala |
| | | | | 50 | | | | | 55 | | | | | 60 | |

| Leu | Arg | Val | Leu | Ile | Gly | Glu | Asn |
| 65 | | | | | 70 | | |

( 2 ) INFORMATION FOR SEQ ID NO:6:

( i ) SEQUENCE CHARACTERISTICS:
( A ) LENGTH: 73 amino acids
( B ) TYPE: amino acid
( C ) STRANDEDNESS:
( D ) TOPOLOGY: unknown ( i i ) MOLECULE TYPE: protein ( x i ) SEQUENCE DESCRIPTION: SEQ ID NO:6:

| Ala | Gly | Phe | Phe | Met | Glu | Glu | Leu | Asn | Thr | Tyr | Arg | Gln | Lys | Gln | Gly |
| 1 | | | | 5 | | | | | 10 | | | | | 15 | |

| Val | Val | Leu | Lys | Tyr | Gln | Glu | Leu | Pro | Asn | Ser | Gly | Pro | Pro | His | Asp |
| | | | 20 | | | | | 25 | | | | | 30 | | |

| Arg | Arg | Phe | Thr | Phe | Gln | Val | Ile | Ile | Asp | Gly | Arg | Glu | Phe | Pro | Glu |
| | | | 35 | | | | | 40 | | | | | 45 | | |

| Gly | Glu | Gly | Arg | Ser | Lys | Lys | Glu | Ala | Lys | Asn | Ala | Ala | Ala | Lys | Leu |
| | | | | 50 | | | | | 55 | | | | | 60 | |

| Ala | Val | Glu | Ile | Leu | Asn | Lys | Glu | Lys |
| 65 | | | | | 70 | | | |

( 2 ) INFORMATION FOR SEQ ID NO:7:

( i ) SEQUENCE CHARACTERISTICS:
( A ) LENGTH: 71 amino acids
( B ) TYPE: amino acid
( C ) STRANDEDNESS:
( D ) TOPOLOGY: unknown ( i i ) MOLECULE TYPE: protein ( x i ) SEQUENCE DESCRIPTION: SEQ ID NO:7:

| Gly | Asn | Tyr | Ile | Gly | Leu | Ile | Asn | Arg | Ile | Ala | Gln | Lys | Lys | Arg | Leu |
| 1 | | | | 5 | | | | | 10 | | | | | 15 | |

| Thr | Val | Asn | Tyr | Glu | Gln | Cys | Ala | Ser | Gly | Val | His | Gly | Pro | Glu | Gly |
| | | | 20 | | | | | 25 | | | | | 30 | | |

| Phe | Glu | Tyr | Lys | Cys | Lys | Met | Gly | Gln | Lys | Glu | Tyr | Ser | Ile | Gly | Thr |
| | | | 35 | | | | | 40 | | | | | 45 | | |

| Gly | Ser | Thr | Lys | Gln | Glu | Ala | Lys | Gln | Leu | Ala | Ala | Lys | Leu | Ala | Tyr |
| | | | | 50 | | | | | 55 | | | | | 60 | |

| Leu | Gln | Ile | Leu | Ser | Glu | Glu |
| 65 | | | | | 70 | |

( 2 ) INFORMATION FOR SEQ ID NO:8:

( i ) SEQUENCE CHARACTERISTICS:
( A ) LENGTH: 72 amino acids
( B ) TYPE: amino acid
( C ) STRANDEDNESS:

( D ) TOPOLOGY: unknown ( i i ) MOLECULE TYPE: protein ( x i ) SEQUENCE DESCRIPTION: SEQ ID NO:8:

| Gly | Phe | Tyr | Met | Asp | Lys | Leu | Asn | Lys | Tyr | Arg | Gln | Met | His | Gly | Val |
|---|---|---|---|---|---|---|---|---|---|---|---|---|---|---|---|
| 1 | | | | 5 | | | | | 10 | | | | | 15 | |
| Ala | Ile | Thr | Tyr | Lys | Glu | Leu | Ser | Thr | Ser | Gly | Pro | Pro | His | Asp | Arg |
| | | | 20 | | | | | 25 | | | | | 30 | | |
| Arg | Phe | Thr | Phe | Gln | Val | Leu | Ile | Asp | Glu | Lys | Glu | Phe | Gly | Glu | Ala |
| | | 35 | | | | | 40 | | | | | 45 | | | |
| Lys | Gly | Arg | Ser | Lys | Thr | Glu | Ala | Arg | Asn | Ala | Ala | Ala | Lys | Leu | Ala |
| | 50 | | | | | 55 | | | | | 60 | | | | |
| Val | Asp | Ile | Leu | Asp | Asn | Glu | Asn | | | | | | | | |
| 65 | | | | | 70 | | | | | | | | | | |

( 2 ) INFORMATION FOR SEQ ID NO:9:

( i ) SEQUENCE CHARACTERISTICS:
( A ) LENGTH: 72 amino acids
( B ) TYPE: amino acid
( C ) STRANDEDNESS:
( D ) TOPOLOGY: unknown ( i i ) MOLECULE TYPE: protein ( x i ) SEQUENCE DESCRIPTION: SEQ ID NO:9:

| Val | Gly | Asn | Tyr | Ile | Gly | Leu | Val | Asn | Ser | Phe | Ala | Gln | Lys | Lys | Lys |
|---|---|---|---|---|---|---|---|---|---|---|---|---|---|---|---|
| 1 | | | | 5 | | | | | 10 | | | | | 15 | |
| Leu | Ser | Val | Leu | Ile | Glu | Gln | Cys | Glu | Pro | Asn | Ser | Glu | Leu | Pro | Gln |
| | | | 20 | | | | | 25 | | | | | 30 | | |
| Arg | Phe | Ile | Cys | Lys | Cys | Lys | Ile | Gly | Gln | Thr | Met | Tyr | Gly | Thr | Gly |
| | | 35 | | | | | 40 | | | | | 45 | | | |
| Ser | Gly | Val | Thr | Lys | Gln | Glu | Ala | Lys | Gln | Leu | Ala | Ala | Lys | Glu | Ala |
| | 50 | | | | | 55 | | | | | 60 | | | | |
| Tyr | Gln | Lys | Leu | Leu | Lys | Ser | Pro | | | | | | | | |
| 65 | | | | | 70 | | | | | | | | | | |

( 2 ) INFORMATION FOR SEQ ID NO:10:

( i ) SEQUENCE CHARACTERISTICS:
( A ) LENGTH: 71 amino acids
( B ) TYPE: amino acid
( C ) STRANDEDNESS:
( D ) TOPOLOGY: unknown ( i i ) MOLECULE TYPE: protein ( x i ) SEQUENCE DESCRIPTION: SEQ ID NO:10:

| Lys | Thr | Pro | Ile | Ser | Leu | Leu | Gln | Glu | Tyr | Gly | Thr | Arg | Ile | Gly | Lys |
|---|---|---|---|---|---|---|---|---|---|---|---|---|---|---|---|
| 1 | | | | 5 | | | | | 10 | | | | | 15 | |
| Thr | Pro | Val | Tyr | Asp | Leu | Leu | Lys | Ala | Glu | Gly | Gln | Ala | His | Gln | Pro |
| | | | 20 | | | | | 25 | | | | | 30 | | |
| Asn | Phe | Thr | Phe | Arg | Val | Thr | Val | Gly | Asp | Thr | Ser | Cys | Thr | Gly | Gln |
| | | 35 | | | | | 40 | | | | | 45 | | | |
| Gly | Pro | Ser | Lys | Lys | Ala | Ala | Lys | His | Lys | Ala | Ala | Glu | Val | Ala | Leu |
| | 50 | | | | | 55 | | | | | 60 | | | | |
| Lys | Glu | Leu | Lys | Gly | Gly | Ser | | | | | | | | | |
| 65 | | | | | 70 | | | | | | | | | | |

( 2 ) INFORMATION FOR SEQ ID NO:11:

( i ) SEQUENCE CHARACTERISTICS:
  ( A ) LENGTH: 72 amino acids
  ( B ) TYPE: amino acid
  ( C ) STRANDEDNESS:
  ( D ) TOPOLOGY: unknown ( i i ) MOLECULE TYPE: protein ( x i ) SEQUENCE DESCRIPTION: SEQ ID NO:11:

Cys Asn Pro Val Gly Ala Leu Gln Glu Leu Val Val Gln Lys Gly Trp
1               5                   10                  15

Arg Leu Pro Glu Tyr Thr Val Thr Gln Glu Ser Gly Pro Ala His Arg
            20                  25                  30

Lys Glu Phe Thr Met Thr Cys Arg Val Glu Arg Phe Ile Glu Ile Gly
            35                  40                  45

Ser Gly Thr Ser Lys Lys Leu Ala Lys Arg Asn Ala Ala Ala Lys Met
        50                  55                  60

Leu Leu Arg Val His Thr Val Pro
65                  70

( 2 ) INFORMATION FOR SEQ ID NO:12:

( i ) SEQUENCE CHARACTERISTICS:
  ( A ) LENGTH: 73 amino acids
  ( B ) TYPE: amino acid
  ( C ) STRANDEDNESS:
  ( D ) TOPOLOGY: unknown ( i i ) MOLECULE TYPE: protein ( x i ) SEQUENCE DESCRIPTION: SEQ ID NO:12:

Gly Pro Ala Cys Cys Arg Val Leu Ser Glu Leu Ser Glu Glu Gln Ala
1               5                   10                  15

Phe His Val Ser Tyr Leu Asp Ile Glu Glu Leu Ser Leu Ser Gly Leu
            20                  25                  30

Cys Gln Cys Leu Val Glu Leu Ser Thr Gln Pro Ala Thr Val Cys His
            35                  40                  45

Gly Ser Ala Thr Thr Arg Glu Ala Ala Arg Gly Glu Ala Ala Arg Arg
        50                  55                  60

Ala Leu Gln Tyr Leu Lys Ile Met Ala
65                  70

( 2 ) INFORMATION FOR SEQ ID NO:13:

( i ) SEQUENCE CHARACTERISTICS:
  ( A ) LENGTH: 71 amino acids
  ( B ) TYPE: amino acid
  ( C ) STRANDEDNESS:
  ( D ) TOPOLOGY: unknown ( i i ) MOLECULE TYPE: protein ( x i ) SEQUENCE DESCRIPTION: SEQ ID NO:13:

Glu Thr Pro Ile Gln Leu Leu His Glu Phe Gly Thr Lys Thr Gly Asn
1               5                   10                  15

His Pro Val Tyr Thr Leu Glu Lys Ala Glu Gly Gln Ala His Asn Pro
            20                  25                  30

Ser Phe Thr Phe Arg Leu Val Ile Gly Asp Ile Thr Ser Leu Gly Glu
            35                  40                  45

Gly Pro Ser Lys Lys Thr Pro Lys Gln Lys Ala Ala Glu Phe Ala Leu
        50                  55                  60

Asn Ile Leu Arg Gly Asp Thr
65                  70

( 2 ) INFORMATION FOR SEQ ID NO:14:

( i ) SEQUENCE CHARACTERISTICS:
        ( A ) LENGTH: 72 amino acids
        ( B ) TYPE: amino acid
        ( C ) STRANDEDNESS:
        ( D ) TOPOLOGY: unknown ( i i ) MOLECULE TYPE: protein ( x i ) SEQUENCE DESCRIPTION: SEQ ID NO:14:

```
Glu Asn Pro Val Gly Ser Leu Gln Glu Leu Ala Val Gln Lys Gly Trp
 1               5                  10                  15
Arg Leu Pro Glu Tyr Thr Val Ala Gln Glu Ser Gly Pro Pro His Lys
            20                  25                  30
Arg Glu Phe Thr Ile Thr Cys Arg Val Glu Thr Phe Val Glu Thr Gly
        35                  40                  45
Ser Gly Thr Ser Lys Gln Val Ala Lys Arg Val Ala Ala Glu Lys Leu
    50                  55                  60
Leu Thr Lys Phe Lys Thr Ile Ser
65                  70
```

( 2 ) INFORMATION FOR SEQ ID NO:15:

( i ) SEQUENCE CHARACTERISTICS:
        ( A ) LENGTH: 72 amino acids
        ( B ) TYPE: amino acid
        ( C ) STRANDEDNESS:
        ( D ) TOPOLOGY: unknown ( i i ) MOLECULE TYPE: protein ( x i ) SEQUENCE DESCRIPTION: SEQ ID NO:15:

```
Thr Asp Tyr Val Lys Met Leu Lys Asp Val Ala Glu Glu Leu Asp Phe
 1               5                  10                  15
Asn Leu Thr Tyr Leu Asp Ile Asp Glu Leu Ser Val Asn Gly Gln Tyr
            20                  25                  30
Gln Cys Leu Ala Glu Leu Ser Thr Asn Pro Ile Thr Val Cys His Gly
        35                  40                  45
Thr Gly Ile Ser Cys Gly Asn Ala His Asn Asp Ala Ala His Asn Ala
    50                  55                  60
Leu Gln Tyr Leu Lys Ile Met Cys
65                  70
```

( 2 ) INFORMATION FOR SEQ ID NO:16:

( i ) SEQUENCE CHARACTERISTICS:
        ( A ) LENGTH: 71 amino acids
        ( B ) TYPE: amino acid
        ( C ) STRANDEDNESS:
        ( D ) TOPOLOGY: unknown ( i i ) MOLECULE TYPE: protein ( x i ) SEQUENCE DESCRIPTION: SEQ ID NO:16:

```
Lys Thr Pro Met Cys Leu Val Asn Glu Leu Ala Arg Tyr Asn Lys Ile
 1               5                  10                  15
Thr His Gln Tyr Arg Leu Thr Glu Glu Arg Gly Pro Ala His Cys Lys
            20                  25                  30
Thr Phe Thr Val Thr Leu Met Leu Gly Asp Glu Glu Tyr Ser Ala Asp
        35                  40                  45
Gly Phe Lys Ile Lys Lys Ala Gln His Leu Ala Ala Ser Lys Ala Ile
```

Glu Glu Thr Met Tyr Lys His
65                  70

( 2 ) INFORMATION FOR SEQ ID NO:17:

( i ) SEQUENCE CHARACTERISTICS:
        ( A ) LENGTH: 69 amino acids
        ( B ) TYPE: amino acid
        ( C ) STRANDEDNESS:
        ( D ) TOPOLOGY: unknown ( i i ) MOLECULE TYPE: protein ( x i ) SEQUENCE DESCRIPTION: SEQ ID NO:17:

Lys Phe Pro Ser Arg Phe Ala Leu Pro Pro Pro Leu Gly Ala His Val
1               5                   10                  15

His His Gly Pro Asn Gly Pro Phe Pro Ser Val Pro Thr Pro Pro Ser
            20                  25                  30

Lys Ile Thr Leu Phe Val Gly Lys Gln Lys Phe Val Gly Ile Gly Arg
            35                  40                  45

Thr Leu Gln Gln Ala Lys His Asp Ala Ala Ala Arg Ala Leu Gln Val
        50                  55                  60

Leu Lys Thr Gln Ala
65

( 2 ) INFORMATION FOR SEQ ID NO:18:

( i ) SEQUENCE CHARACTERISTICS:
        ( A ) LENGTH: 71 amino acids
        ( B ) TYPE: amino acid
        ( C ) STRANDEDNESS:
        ( D ) TOPOLOGY: unknown ( i i ) MOLECULE TYPE: protein ( x i ) SEQUENCE DESCRIPTION: SEQ ID NO:18:

Lys Ser Pro Ile Ser Gln Val His Glu Ile Gly Ile Lys Arg Asn Met
1               5                   10                  15

Thr Val His Phe Lys Val Leu Arg Glu Glu Gly Pro Ala His Met Lys
            20                  25                  30

Asn Phe Ile Thr Ala Cys Ile Val Gly Ser Ile Val Thr Glu Gly Glu
            35                  40                  45

Gly Asn Gly Lys Lys Val Ser Lys Lys Arg Ala Ala Glu Lys Met Leu
        50                  55                  60

Val Glu Leu Gln Lys Leu Pro
65                  70

( 2 ) INFORMATION FOR SEQ ID NO:19:

( i ) SEQUENCE CHARACTERISTICS:
        ( A ) LENGTH: 73 amino acids
        ( B ) TYPE: amino acid
        ( C ) STRANDEDNESS:
        ( D ) TOPOLOGY: unknown ( i i ) MOLECULE TYPE: protein ( x i ) SEQUENCE DESCRIPTION: SEQ ID NO:19:

Asp Asn Pro Ile Thr Lys Leu Ile Gln Leu Gln Gln Thr Arg Lys Glu
1               5                   10                  15

Lys Glu Pro Ile Phe Glu Leu Ile Ala Lys Asn Gly Asn Glu Thr Ala
            20                  25                  30

Arg Arg Arg Glu Phe Val Met Glu Val Ser Ala Ser Gly Ser Thr Ala
        35                  40                  45

Arg Gly Thr Gly Asn Ser Lys Lys Leu Ala Lys Arg Asn Ala Ala Gln
    50                  55                  60

Ala Leu Phe Glu Leu Leu Glu Ala Val
65              70

( 2 ) INFORMATION FOR SEQ ID NO:20:

( i ) SEQUENCE CHARACTERISTICS:
        ( A ) LENGTH: 70 amino acids
        ( B ) TYPE: amino acid
        ( C ) STRANDEDNESS:
        ( D ) TOPOLOGY: unknown ( i i ) MOLECULE TYPE: protein ( x i ) SEQUENCE DESCRIPTION: SEQ ID NO:20:

His Met Lys Glu Gln Leu Leu Tyr Leu Ser Lys Leu Leu Asp Phe Glu
1               5                   10                  15

Val Asn Phe Ser Asp Tyr Pro Lys Gly Asn His Asn Glu Phe Leu Thr
            20                  25                  30

Ile Val Thr Leu Ser Thr His Pro Pro Gln Ile Cys His Gly Val Gly
        35                  40                  45

Lys Ser Ser Glu Glu Ser Gln Asn Asp Ala Ala Ser Asn Ala Leu Lys
    50                  55                  60

Ile Leu Ser Lys Leu Gly
65              70

( 2 ) INFORMATION FOR SEQ ID NO:21:

( i ) SEQUENCE CHARACTERISTICS:
        ( A ) LENGTH: 74 amino acids
        ( B ) TYPE: amino acid
        ( C ) STRANDEDNESS:
        ( D ) TOPOLOGY: unknown ( i i ) MOLECULE TYPE: protein ( x i ) SEQUENCE DESCRIPTION: SEQ ID NO:21:

Lys His Pro Val Ser Ala Leu Met Glu Ile Cys Asn Lys Arg Arg Trp
1               5                   10                  15

Gln Pro Pro Glu Phe Leu Leu Val His Asp Ser Gly Pro Asp His Arg
            20                  25                  30

Lys His Phe Leu Phe Arg Val Leu Ile Asn Gly Ser Ala Tyr Gln Pro
        35                  40                  45

Ser Phe Ala Ser Pro Asn Lys Lys Glu Ala Lys Ala Thr Ala Ala Thr
    50                  55                  60

Val Val Leu Gln Ala Met Gly Leu Val Pro
65              70

( 2 ) INFORMATION FOR SEQ ID NO:22:

( i ) SEQUENCE CHARACTERISTICS:
        ( A ) LENGTH: 71 amino acids
        ( B ) TYPE: amino acid
        ( C ) STRANDEDNESS:
        ( D ) TOPOLOGY: unknown ( i i ) MOLECULE TYPE: protein ( x i ) SEQUENCE DESCRIPTION: SEQ ID NO:22:

Ala Asn Pro Val Thr Val Ile Asn Glu Tyr Cys Gln Ile Thr Arg Arg
1               5                   10                  15

-continued

```
Asp  Trp  Ser  Phe  Arg  Ile  Glu  Ser  Val  Gly  Pro  Ser  Asn  Ser  Pro  Thr
               20                  25                       30

Phe  Tyr  Ala  Cys  Val  Asp  Ile  Asp  Gly  Arg  Val  Phe  Asp  Lys  Ala  Asp
          35                  40                       45

Gly  Lys  Ser  Lys  Arg  Asp  Ala  Lys  Asn  Asn  Ala  Ala  Lys  Leu  Ala  Val
     50                       55                       60

Asp  Lys  Leu  Leu  Gly  Tyr  Val
65                       70
```

(2) INFORMATION FOR SEQ ID NO:23:

(i) SEQUENCE CHARACTERISTICS:
        (A) LENGTH: 69 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:23:

```
Pro  Asp  Pro  Leu  Ile  Arg  Leu  Asn  Asp  Cys  Lys  Thr  Lys  Tyr  Gly  Ile
1                    5                  10                       15

Asp  Ile  Ile  Cys  Arg  Phe  Tyr  Ile  Val  Leu  Asp  Asn  Asp  Gly  Ser  Ile
               20                  25                       30

Ile  His  Met  Cys  Tyr  Met  Arg  Thr  Gly  Ser  Ala  Glu  Ala  Val  Ala  Lys
          35                  40                       45

Gly  Arg  Ser  Lys  Lys  Glu  Ala  Lys  Arg  Ile  Ala  Ala  Lys  Asp  Ile  Leu
     50                       55                       60

Asp  Gln  Ile  Gly  Leu
65
```

(2) INFORMATION FOR SEQ ID NO:24:

(i) SEQUENCE CHARACTERISTICS:
        (A) LENGTH: 71 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:24:

```
Asp  Lys  Leu  Ala  Lys  Ser  Lys  Leu  Phe  His  Lys  Tyr  Ser  Thr  Leu  Gly
1                    5                  10                       15

His  Ile  Glu  Tyr  Arg  Trp  Val  Asp  Gly  Ala  Gly  Gly  Ser  Ala  Glu  Gly
               20                  25                       30

Tyr  Val  Ile  Ala  Cys  Ile  Phe  Asn  Gly  Lys  Glu  Val  Ala  Arg  Ala  Trp
          35                  40                       45

Gly  Ala  Asn  Gln  Lys  Asp  Ala  Gly  Ser  Arg  Ala  Ala  Met  Gln  Ala  Leu
     50                       55                       60

Glu  Val  Leu  Ala  Lys  Asp  Tyr
65                       70
```

(2) INFORMATION FOR SEQ ID NO:25:

(i) SEQUENCE CHARACTERISTICS:
        (A) LENGTH: 73 amino acids
        (B) TYPE: amino acid
        (C) STRANDEDNESS:
        (D) TOPOLOGY: unknown (ii) MOLECULE TYPE: protein ( x i ) SEQUENCE DESCRIPTION: SEQ ID NO:25:

| Lys | Asp | Pro | Lys | Thr | Arg | Leu | Gln | Glu | Tyr | Leu | Gln | Gly | Arg | His | Leu |
| 1 | | | | 5 | | | | | 10 | | | | | 15 | |

| Pro | Leu | Pro | Thr | Tyr | Leu | Val | Val | Gln | Val | Arg | Gly | Glu | Ala | His | Asp |
| | | | 20 | | | | | 25 | | | | | 30 | | |

| Gln | Glu | Phe | Thr | Ile | His | Cys | Gln | Val | Ser | Gly | Leu | Ser | Glu | Pro | Val |
| | | | 35 | | | | 40 | | | | | 45 | | | |

| Val | Gly | Thr | Gly | Ser | Ser | Arg | Arg | Lys | Ala | Glu | Gln | Ala | Ala | Ala | Glu |
| | | 50 | | | | 55 | | | | | 60 | | | | |

| Gln | Ala | Leu | Lys | Lys | Leu | Glu | Leu | Glu |
| 65 | | | | | 70 | | | |

( 2 ) INFORMATION FOR SEQ ID NO:26:

( i ) SEQUENCE CHARACTERISTICS:
        ( A ) LENGTH: 56 amino acids
        ( B ) TYPE: amino acid
        ( C ) STRANDEDNESS:
        ( D ) TOPOLOGY: unknown ( i i ) MOLECULE TYPE: protein ( x i ) SEQUENCE DESCRIPTION: SEQ ID NO:26:

| Lys | Asn | Pro | Xaa | Xaa | Xaa | Xaa | Xaa | Xaa | Xaa | Xaa | Gln | Xaa | Xaa | Pro | Glu |
| 1 | | | | 5 | | | | | 10 | | | | | 15 | |

| Xaa | Xaa | Xaa | Xaa | Ser | Gly | Pro | Xaa | His | Xaa | Xaa | Xaa | Xaa | Xaa | Xaa | Xaa |
| | | | 20 | | | | | 25 | | | | | 30 | | |

| Xaa | Gly | Xaa | Xaa | Glu | Xaa | Xaa | Xaa | Xaa | Xaa | Xaa | Xaa | Xaa | Ala | Xaa | Xaa |
| | | | 35 | | | | 40 | | | | | 45 | | | |

| Ala | Ala | Xaa | Ala | Xaa | Xaa | Xaa | Xaa |
| | | 50 | | | | 55 | |

( 2 ) INFORMATION FOR SEQ ID NO:27:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:27:

CCGGAATTCN GGNAAAGGTN GA          22

( 2 ) INFORMATION FOR SEQ ID NO:28:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: unknown ( i i ) MOLECULE TYPE: protein ( x i ) SEQUENCE DESCRIPTION: SEQ ID NO:28:

| Pro | Gly | Lys | Val | Glu |
| 1 | | | | 5 |

( 2 ) INFORMATION FOR SEQ ID NO:29:

( i ) SEQUENCE CHARACTERISTICS:
        ( A ) LENGTH: 28 base pairs
        ( B ) TYPE: nucleic acid
        ( C ) STRANDEDNESS: double ( D ) TOPOLOGY: unknown ( i i ) MOLECULE TYPE: cDNA ( x i ) SEQUENCE DESCRIPTION: SEQ ID NO:29:

CGGGATCCNG CTCTCCTTCT GGTCTTNA                                                      2 8

( 2 ) INFORMATION FOR SEQ ID NO:30:

( i ) SEQUENCE CHARACTERISTICS:
          ( A ) LENGTH: 5 amino acids
          ( B ) TYPE: amino acid
          ( C ) STRANDEDNESS:
          ( D ) TOPOLOGY: unknown ( i i ) MOLECULE TYPE: protein ( x i ) SEQUENCE DESCRIPTION: SEQ ID NO:30:

Ala  Glu  Gln  Lys  Leu
     1                   5

( 2 ) INFORMATION FOR SEQ ID NO:31:

( i ) SEQUENCE CHARACTERISTICS:
          ( A ) LENGTH: 27 base pairs
          ( B ) TYPE: nucleic acid
          ( C ) STRANDEDNESS: double
          ( D ) TOPOLOGY: unknown ( i i ) MOLECULE TYPE: cDNA ( x i ) SEQUENCE DESCRIPTION: SEQ ID NO:31:

CGGAATTCAA AGACNGGNTA CTGTNGA                                                       2 7

( 2 ) INFORMATION FOR SEQ ID NO:32:

( i ) SEQUENCE CHARACTERISTICS:
          ( A ) LENGTH: 6 amino acids
          ( B ) TYPE: amino acid
          ( C ) STRANDEDNESS:
          ( D ) TOPOLOGY: unknown ( i i ) MOLECULE TYPE: protein ( x i ) SEQUENCE DESCRIPTION: SEQ ID NO:32:

Lys  Thr  Gly  Tyr  Val  Asp
     1                   5

( 2 ) INFORMATION FOR SEQ ID NO:33:

( i ) SEQUENCE CHARACTERISTICS:
          ( A ) LENGTH: 32 base pairs
          ( B ) TYPE: nucleic acid
          ( C ) STRANDEDNESS: double
          ( D ) TOPOLOGY: unknown ( i i ) MOLECULE TYPE: cDNA ( x i ) SEQUENCE DESCRIPTION: SEQ ID NO:33:

CGGGATCCGA TCGATCNGGG TAATGATCGA TC                                                 3 2

( 2 ) INFORMATION FOR SEQ ID NO:34:

( i ) SEQUENCE CHARACTERISTICS:
          ( A ) LENGTH: 6 amino acids
          ( B ) TYPE: amino acid
          ( C ) STRANDEDNESS:
          ( D ) TOPOLOGY: unknown ( i i ) MOLECULE TYPE: protein -continued ( x i ) SEQUENCE DESCRIPTION: SEQ ID NO:34:

Asp Asp Pro Ile Asp Asp
1               5

( 2 ) INFORMATION FOR SEQ ID NO:35:

( i ) SEQUENCE CHARACTERISTICS:
      ( A ) LENGTH: 23 base pairs
      ( B ) TYPE: nucleic acid
      ( C ) STRANDEDNESS: double
      ( D ) TOPOLOGY: unknown ( i i ) MOLECULE TYPE: cDNA ( x i ) SEQUENCE DESCRIPTION: SEQ ID NO:35:

CTTTGCACGC ACGTAGGCTC CTG                    23

( 2 ) INFORMATION FOR SEQ ID NO:36:

( i ) SEQUENCE CHARACTERISTICS:
      ( A ) LENGTH: 28 base pairs
      ( B ) TYPE: nucleic acid
      ( C ) STRANDEDNESS: double
      ( D ) TOPOLOGY: unknown ( i i ) MOLECULE TYPE: cDNA ( x i ) SEQUENCE DESCRIPTION: SEQ ID NO:36:

CGGGATCCAT CTGNCCAGTT CTTCTGTT               28

( 2 ) INFORMATION FOR SEQ ID NO:37:

( i ) SEQUENCE CHARACTERISTICS:
      ( A ) LENGTH: 13 amino acids
      ( B ) TYPE: amino acid
      ( C ) STRANDEDNESS:
      ( D ) TOPOLOGY: unknown ( i i ) MOLECULE TYPE: protein ( x i ) SEQUENCE DESCRIPTION: SEQ ID NO:37:

Lys Ile Leu Ala Ala Ile Ile Met Lys Lys Asp Ser Glu
1               5                   10

( 2 ) INFORMATION FOR SEQ ID NO:38:

( i ) SEQUENCE CHARACTERISTICS:
      ( A ) LENGTH: 13 amino acids
      ( B ) TYPE: amino acid
      ( C ) STRANDEDNESS:
      ( D ) TOPOLOGY: unknown ( i i ) MOLECULE TYPE: protein ( x i ) SEQUENCE DESCRIPTION: SEQ ID NO:38:

Pro Gln Asp Ser Gly His His His Tyr Glu Lys Arg Leu
1               5                   10

( 2 ) INFORMATION FOR SEQ ID NO:39:

( i ) SEQUENCE CHARACTERISTICS:
      ( A ) LENGTH: 4 amino acids
      ( B ) TYPE: amino acid
      ( C ) STRANDEDNESS:
      ( D ) TOPOLOGY: unknown ( i i ) MOLECULE TYPE: protein ( x i ) SEQUENCE DESCRIPTION: SEQ ID NO:39:

Arg Glu Pro Arg
1

( 2 ) INFORMATION FOR SEQ ID NO:40:

( i ) SEQUENCE CHARACTERISTICS:
        ( A ) LENGTH: 609 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: exon
        ( B ) LOCATION: 11
        ( D ) OTHER INFORMATION: /note= "N in position 11 is an
            EXON1 (179 bp) sequence."

( i x ) FEATURE:
        ( A ) NAME/KEY: intron
        ( B ) LOCATION: 32
        ( D ) OTHER INFORMATION: /note= "N in position 32 is an
            INTRON1 (5.4 Kb) sequence."

( i x ) FEATURE:
        ( A ) NAME/KEY: exon
        ( B ) LOCATION: 53
        ( D ) OTHER INFORMATION: /note= "N in position 53 is an
            EXON2 (1586 bp) sequence."

( i x ) FEATURE:
        ( A ) NAME/KEY: intron
        ( B ) LOCATION: 74
        ( D ) OTHER INFORMATION: /note= "N in position 74 is an
            INTRON2 (2.5 Kb) sequence."

( i x ) FEATURE:
        ( A ) NAME/KEY: exon
        ( B ) LOCATION: 95
        ( D ) OTHER INFORMATION: /note= "N in position 95 is an
            EXON3 (184 bp) sequence."

( i x ) FEATURE:
        ( A ) NAME/KEY: intron
        ( B ) LOCATION: 116
        ( D ) OTHER INFORMATION: /note= "N in position 116 is an
            INTRON3 (0.4 Kb) sequence."

( i x ) FEATURE:
        ( A ) NAME/KEY: exon
        ( B ) LOCATION: 137
        ( D ) OTHER INFORMATION: /note= "N in position 137 is an
            EXON4 (149 bp) sequence."

( i x ) FEATURE:
        ( A ) NAME/KEY: intron
        ( B ) LOCATION: 158
        ( D ) OTHER INFORMATION: /note= "N in position 158 is an
            INTRON4 (571 bp) sequence."

( i x ) FEATURE:
        ( A ) NAME/KEY: exon
        ( B ) LOCATION: 179
        ( D ) OTHER INFORMATION: /note= "N in position 179 is an
            EXON5 (145 bp) sequence."

( i x ) FEATURE:
        ( A ) NAME/KEY: intron
        ( B ) LOCATION: 200
        ( D ) OTHER INFORMATION: /note= "N in position 200 is an
            INTRON5 (127 bp) sequence."

( i x ) FEATURE:
        ( A ) NAME/KEY: exon
        ( B ) LOCATION: 221
        ( D ) OTHER INFORMATION: /note= "N in position 221 is an
            EXON6 (191 bp) sequence."

( i x ) FEATURE:
        ( A ) NAME/KEY: intron
        ( B ) LOCATION: 242
        ( D ) OTHER INFORMATION: /note= "N in position 242 is an
              INTRON6 (6.5 Kb) sequence."

( i x ) FEATURE:
        ( A ) NAME/KEY: exon
        ( B ) LOCATION: 263
        ( D ) OTHER INFORMATION: /note= "N in position 263 is an
              EXON7 (226 bp) sequence."

( i x ) FEATURE:
        ( A ) NAME/KEY: intron
        ( B ) LOCATION: 284
        ( D ) OTHER INFORMATION: /note= "N in position 284 is an
              INTRON7 (255 bp) sequence."

( i x ) FEATURE:
        ( A ) NAME/KEY: exon
        ( B ) LOCATION: 305
        ( D ) OTHER INFORMATION: /note= "N in position 305 is an
              EXON8 (172 bp) sequence."

( i x ) FEATURE:
        ( A ) NAME/KEY: intron
        ( B ) LOCATION: 326
        ( D ) OTHER INFORMATION: /note= "N in position 326 is an
              INTRON8 (235 bp) sequence."

( i x ) FEATURE:
        ( A ) NAME/KEY: exon
        ( B ) LOCATION: 347
        ( D ) OTHER INFORMATION: /note= "N in position 347 is an
              EXON9 (94 bp) sequence."

( i x ) FEATURE:
        ( A ) NAME/KEY: intron
        ( B ) LOCATION: 368
        ( D ) OTHER INFORMATION: /note= "N in position 368 is an
              INTRON9 (0.6 Kb) sequence."

( i x ) FEATURE:
        ( A ) NAME/KEY: exon
        ( B ) LOCATION: 389
        ( D ) OTHER INFORMATION: /note= "N in position 389 is an
              EXON10 (123 bp) sequence."

( i x ) FEATURE:
        ( A ) NAME/KEY: intron
        ( B ) LOCATION: 410
        ( D ) OTHER INFORMATION: /note= "N in position 410 is an
              INTRON10 (292 bp) sequence."

( i x ) FEATURE:
        ( A ) NAME/KEY: exon
        ( B ) LOCATION: 431
        ( D ) OTHER INFORMATION: /note= "N in position 431 is an
              EXON11 (134 bp) sequence."

( i x ) FEATURE:
        ( A ) NAME/KEY: intron
        ( B ) LOCATION: 452
        ( D ) OTHER INFORMATION: /note= "N in position 452 is an
              INTRON11 (1.6 Kb) sequence."

( i x ) FEATURE:
        ( A ) NAME/KEY: exon
        ( B ) LOCATION: 473
        ( D ) OTHER INFORMATION: /note= "N in position 473 is an
              EXON12 (183 bp) sequence."

( i x ) FEATURE:
        ( A ) NAME/KEY: intron
        ( B ) LOCATION: 494
        ( D ) OTHER INFORMATION: /note= "N in position 494 is an
              INTRON12 (315 bp) sequence."

( i x ) FEATURE:

(A) NAME/KEY: exon
(B) LOCATION: 515
(D) OTHER INFORMATION: /note= "N in position 515 is an EXON13 (113 bp) sequence."

(ix) FEATURE:
(A) NAME/KEY: intron
(B) LOCATION: 536
(D) OTHER INFORMATION: /note= "N in position 536 is an INTRON13 (408 bp) sequence."

(ix) FEATURE:
(A) NAME/KEY: exon
(B) LOCATION: 557
(D) OTHER INFORMATION: /note= "N in position 557 is an EXON14 (128 bp) sequence."

(ix) FEATURE:
(A) NAME/KEY: intron
(B) LOCATION: 578
(D) OTHER INFORMATION: /note= "N in position 578 is an INTRON14 (173 bp) sequence."

(ix) FEATURE:
(A) NAME/KEY: exon
(B) LOCATION: 599
(D) OTHER INFORMATION: /note= "N in position 599 is an EXON15 (2975 bp) sequence."

(xi) SEQUENCE DESCRIPTION: SEQ ID NO:40:

| | | | | | |
|---|---|---|---|---|---|
| GGGCCCGGCG | NTCCGCGGCA | GGTAAGCCGG | GNTATTCTGC | AGGGGTATTC | CCNATGAACC | 60
| TCGGTAAGAG | ACCNTTCCGT | CAAGATTTAA | ATTCNATCAG | AGAAGGTAGG | TGTCCNTTTT | 120
| CTCTAGACTG | CAGAGTNATG | AACCCAAGTA | TGTCCTANCT | CCTGTCAGGT | TCCAATACNT | 180
| GATAACCAGG | TAGGGCGTTN | TCTCCTTTAG | CCTGAAGGTA | NACGAGCCCA | AGTGAGTGTC | 240
| CNCATCCCAA | AGGTTCGTTT | ACNGCCAAAG | ACAGTTAAGA | CGTNTTCCCC | ACAGCTCCCT | 300
| CTCANTTGGG | AACAGGTGAG | TGAGGNACCT | CCCTAGGGAA | TCGCTGNGCT | TCATCAGGTG | 360
| AGCGAGGNCT | TTTTGTAGGG | TTTCTCTANT | GTATATCAGG | TCTGTACAGN | TGTTTTTCAG | 420
| CACTGCTCCG | NGTGGAGAAC | GGTGAGTGAT | ANTCTCACAC | AGGAGAAGGC | ACNGTCACAT | 480
| TGGGTAAGGG | GCCNTTGTAC | TCAGGTTACC | TTTTNCCACC | CCAAGGTGCT | ATAACNGGAT | 540
| TCCTAGGTTG | GCAGAGNCTG | TGGATGGGTA | AGGAAACNGT | TTCTCTAGGC | CACGGAATNC | 600
| AAGAATCTG | | | | | | 609

(2) INFORMATION FOR SEQ ID NO:41:

(i) SEQUENCE CHARACTERISTICS:
(A) LENGTH: 660 base pairs
(B) TYPE: nucleic acid
(C) STRANDEDNESS: double
(D) TOPOLOGY: unknown (ii) MOLECULE TYPE: DNA (genomic)

(xi) SEQUENCE DESCRIPTION: SEQ ID NO:41:

| | | | | | |
|---|---|---|---|---|---|
| GGGGGCTGAC | GCCTGTAATC | CCAACACTTT | GGGAGGCCGA | GGTGGGCGGA | TCTCTTGAAA | 60
| CCGGGAGTTC | GAGACCACCC | TGGCTAACGT | GGTGAAACCC | TGTTCTTACT | AAAAAACCCA | 120
| AAAAAAAAAA | AAAAAAAAAA | AAAGCCAGG | AGTGATGGCG | CTCGCCTGTA | ATCCCAGCTA | 180
| CTCCGTAGGC | TGAGGCAGGA | GAATCGCTTG | AACCCGGCGG | GCAGAGGTTG | CAGTGAACCG | 240
| AGATTGCGCC | ATTGCACTCC | AGCCTGGGCA | AAAGAGCGA | GACTCCGCCT | CAAAAAAAA | 300
| AAAAAAGTA | CCTTCCGTAG | TTCTCATGCA | GCGGAGGGGT | TCGACTTGTA | ACCGGCCTGA | 360
| AACCAAGCGT | GGCGCAAGAT | TTGCTCAAGC | CCCTCCTGTT | GGCCAAACTT | TCCGGAGGGG | 420

| | | | | | |
|---|---|---|---|---|---|
| AAGGCTTTCC | GAGGAAACGA | AAGCGAAATT | GAACCGGAGC | CATCTTGGGC | CCGGCGCGCA | 480
| GACCCGCGGA | GTTTCCCGTG | CCGACGCCCC | GGGGCCACTT | CCAGTGCGGA | GTAGCGGAGG | 540
| CGTGGGGGCC | TCGAGGGGCT | GGCGCGGTCC | AGCGGTCGGG | GCAGGGTCGT | GCCGCCGGCG | 600
| GGTCGGGCCG | GACAATGCCT | CGCGGGCGCA | ATGAATCCGC | GGCAGGTAAG | CCGGGCCGGC | 660

( 2 ) INFORMATION FOR SEQ ID NO:42:

( i ) SEQUENCE CHARACTERISTICS:
        ( A ) LENGTH: 150 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:42:

| | | | | | |
|---|---|---|---|---|---|
| AGTTTTATGA | TTCTGCTTTT | ATGTGTCCCT | TGATAACAGT | GACTTAACAA | TATACATTCC | 60
| TCATAAATAA | AAAAAAACA | AGAATCTGAA | TTCTTAGAAA | GTTTAAGTC | CCTGGTTTTC | 120
| TTGGGGGAG | GGTGGAAAAT | TGGGAAACAA | | | | 150

( 2 ) INFORMATION FOR SEQ ID NO:43:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: other nucleic acid
        ( A ) DESCRIPTION: /desc = "primer"

( x i ) SEQUENCE DESCRIPTION: SEQ ID NO:43:

CCTCAGAACC TCTGTACTCC    20

( 2 ) INFORMATION FOR SEQ ID NO:44:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: other nucleic acid
        ( A ) DESCRIPTION: /desc = "primer"

( x i ) SEQUENCE DESCRIPTION: SEQ ID NO:44:

GTGGCAGTGA CGGTGTCTGC    20

( 2 ) INFORMATION FOR SEQ ID NO:45:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: unknown ( i i ) MOLECULE TYPE: other nucleic acid
        ( A ) DESCRIPTION: /desc = "primer"

( x i ) SEQUENCE DESCRIPTION: SEQ ID NO:45:

GTCACTGTTA TCAAGGGACA C    21

( 2 ) INFORMATION FOR SEQ ID NO:46:

( i ) SEQUENCE CHARACTERISTICS:
        ( A ) LENGTH: 24 base pairs ( B ) TYPE: nucleic acid
            ( C ) STRANDEDNESS: single
            ( D ) TOPOLOGY: unknown ( i i ) MOLECULE TYPE: other nucleic acid
            ( A ) DESCRIPTION: /desc = "primer"

( x i ) SEQUENCE DESCRIPTION: SEQ ID NO:46:

CCTGCCGCGG ATTCATTGCG CCCG 24

( 2 ) INFORMATION FOR SEQ ID NO:47:

( i ) SEQUENCE CHARACTERISTICS:
            ( A ) LENGTH: 25 base pairs
            ( B ) TYPE: nucleic acid
            ( C ) STRANDEDNESS: single
            ( D ) TOPOLOGY: unknown ( i i ) MOLECULE TYPE: other nucleic acid
            ( A ) DESCRIPTION: /desc = "primer"

( x i ) SEQUENCE DESCRIPTION: SEQ ID NO:47:

CGGCTACTCC GCACTGGAAG TGGCC 25

( 2 ) INFORMATION FOR SEQ ID NO:48:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: unknown ( i i ) MOLECULE TYPE: other nucleic acid
            ( A ) DESCRIPTION: /desc = "primer"

( x i ) SEQUENCE DESCRIPTION: SEQ ID NO:48:

CTCGTTGGAA TAGTGGGATG 20

( 2 ) INFORMATION FOR SEQ ID NO:49:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: unknown ( i i ) MOLECULE TYPE: other nucleic acid
            ( A ) DESCRIPTION: /desc = "primer"

( x i ) SEQUENCE DESCRIPTION: SEQ ID NO:49:

AAGAAGGATG TGGCTGAAGG 20

( 2 ) INFORMATION FOR SEQ ID NO:50:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: unknown ( i i ) MOLECULE TYPE: other nucleic acid
            ( A ) DESCRIPTION: /desc = "primer"

( x i ) SEQUENCE DESCRIPTION: SEQ ID NO:50:

CAGAAGCCAT GGAGTTGG 18

( 2 ) INFORMATION FOR SEQ ID NO:51:

( i ) SEQUENCE CHARACTERISTICS:
            ( A ) LENGTH: 22 base pairs ( B ) TYPE: nucleic acid
            ( C ) STRANDEDNESS: single
            ( D ) TOPOLOGY: unknown ( i i ) MOLECULE TYPE: other nucleic acid
            ( A ) DESCRIPTION: /desc = "primer"

( x i ) SEQUENCE DESCRIPTION: SEQ ID NO:51:

GACCTTGAGA GGAGGAGCAT AG                22

( 2 ) INFORMATION FOR SEQ ID NO:52:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: unknown ( i i ) MOLECULE TYPE: other nucleic acid
            ( A ) DESCRIPTION: /desc = "primer"

( x i ) SEQUENCE DESCRIPTION: SEQ ID NO:52:

GAATCTTGCG GCCGAGCAAG G                21

( 2 ) INFORMATION FOR SEQ ID NO:53:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: unknown ( i i ) MOLECULE TYPE: other nucleic acid
            ( A ) DESCRIPTION: /desc = "primer"

( x i ) SEQUENCE DESCRIPTION: SEQ ID NO:53:

TCTCCTCCCT TAGCAGGTTC                20

( 2 ) INFORMATION FOR SEQ ID NO:54:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: unknown ( i i ) MOLECULE TYPE: other nucleic acid
            ( A ) DESCRIPTION: /desc = "primer"

( x i ) SEQUENCE DESCRIPTION: SEQ ID NO:54:

GGACATGGTA CGGAGTCTCT                20

( 2 ) INFORMATION FOR SEQ ID NO:55:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: unknown ( i i ) MOLECULE TYPE: other nucleic acid
            ( A ) DESCRIPTION: /desc = "primer"

( x i ) SEQUENCE DESCRIPTION: SEQ ID NO:55:

CATCTCTTGT CACACGACAG C                21

( 2 ) INFORMATION FOR SEQ ID NO:56:

( i ) SEQUENCE CHARACTERISTICS:
            ( A ) LENGTH: 21 base pairs ( B ) TYPE: nucleic acid
                    ( C ) STRANDEDNESS: single
                    ( D ) TOPOLOGY: unknown ( i i ) MOLECULE TYPE: other nucleic acid
                    ( A ) DESCRIPTION: /desc = "primer"

( x i ) SEQUENCE DESCRIPTION: SEQ ID NO:56:

CACCAGTTGA CGCTTGTCTC C                                                              21

( 2 ) INFORMATION FOR SEQ ID NO:57:

( i ) SEQUENCE CHARACTERISTICS:
                    ( A ) LENGTH: 19 base pairs
                    ( B ) TYPE: nucleic acid
                    ( C ) STRANDEDNESS: single
                    ( D ) TOPOLOGY: unknown ( i i ) MOLECULE TYPE: other nucleic acid
                    ( A ) DESCRIPTION: /desc = "primer"

( x i ) SEQUENCE DESCRIPTION: SEQ ID NO:57:

CTGGTATCTG AGCTGTCTG                                                                 19

( 2 ) INFORMATION FOR SEQ ID NO:58:

( i ) SEQUENCE CHARACTERISTICS:
                    ( A ) LENGTH: 42 base pairs
                    ( B ) TYPE: nucleic acid
                    ( C ) STRANDEDNESS: single
                    ( D ) TOPOLOGY: unknown ( i i ) MOLECULE TYPE: other nucleic acid
                    ( A ) DESCRIPTION: /desc = "primer"

( x i ) SEQUENCE DESCRIPTION: SEQ ID NO:58:

AATTAACCCT CACTAAAGGG GTAAAATGAG AATATGCAGC AA                                        42

( 2 ) INFORMATION FOR SEQ ID NO:59:

( i ) SEQUENCE CHARACTERISTICS:
                    ( A ) LENGTH: 39 base pairs
                    ( B ) TYPE: nucleic acid
                    ( C ) STRANDEDNESS: single
                    ( D ) TOPOLOGY: unknown ( i i ) MOLECULE TYPE: other nucleic acid
                    ( A ) DESCRIPTION: /desc = "primer"

( x i ) SEQUENCE DESCRIPTION: SEQ ID NO:59:

CGCAATTAAC CCTCACTAAA GGATGAACAC ACAGATAAC                                            39

( 2 ) INFORMATION FOR SEQ ID NO:60:

( i ) SEQUENCE CHARACTERISTICS:
                    ( A ) LENGTH: 20 base pairs
                    ( B ) TYPE: nucleic acid
                    ( C ) STRANDEDNESS: single
                    ( D ) TOPOLOGY: unknown ( i i ) MOLECULE TYPE: other nucleic acid
                    ( A ) DESCRIPTION: /desc = "primer"

( x i ) SEQUENCE DESCRIPTION: SEQ ID NO:60:

TGAGATCTGG ATGTGCATTG                                                                20

( 2 ) INFORMATION FOR SEQ ID NO:61:

( i ) SEQUENCE CHARACTERISTICS:
                    ( A ) LENGTH: 20 base pairs ( B ) TYPE: nucleic acid
( C ) STRANDEDNESS: single
( D ) TOPOLOGY: unknown ( i i ) MOLECULE TYPE: other nucleic acid
( A ) DESCRIPTION: /desc = "primer"

( x i ) SEQUENCE DESCRIPTION: SEQ ID NO:61:

AATTAACCCT CACTAAAGGG  20

( 2 ) INFORMATION FOR SEQ ID NO:62:

( i ) SEQUENCE CHARACTERISTICS:
( A ) LENGTH: 27 base pairs
( B ) TYPE: nucleic acid
( C ) STRANDEDNESS: single
( D ) TOPOLOGY: unknown ( i i ) MOLECULE TYPE: other nucleic acid
( A ) DESCRIPTION: /desc = "primer"

( x i ) SEQUENCE DESCRIPTION: SEQ ID NO:62:

CAACCTTGGC GAAATATCGC ATCCTTG  27

( 2 ) INFORMATION FOR SEQ ID NO:63:

( i ) SEQUENCE CHARACTERISTICS:
( A ) LENGTH: 30 base pairs
( B ) TYPE: nucleic acid
( C ) STRANDEDNESS: single
( D ) TOPOLOGY: unknown ( i i ) MOLECULE TYPE: other nucleic acid
( A ) DESCRIPTION: /desc = "primer"

( x i ) SEQUENCE DESCRIPTION: SEQ ID NO:63:

GAATTCATAG ACACCATGAA TATCCACTTG  30

( 2 ) INFORMATION FOR SEQ ID NO:64:

( i ) SEQUENCE CHARACTERISTICS:
( A ) LENGTH: 23 base pairs
( B ) TYPE: nucleic acid
( C ) STRANDEDNESS: single
( D ) TOPOLOGY: unknown ( i i ) MOLECULE TYPE: other nucleic acid
( A ) DESCRIPTION: /desc = "primer"

( x i ) SEQUENCE DESCRIPTION: SEQ ID NO:64:

CGTTACTAGT GAATCCGAGC TCG  23

( 2 ) INFORMATION FOR SEQ ID NO:65:

( i ) SEQUENCE CHARACTERISTICS:
( A ) LENGTH: 25 base pairs
( B ) TYPE: nucleic acid
( C ) STRANDEDNESS: single
( D ) TOPOLOGY: unknown ( i i ) MOLECULE TYPE: other nucleic acid
( A ) DESCRIPTION: /desc = "primer"

( x i ) SEQUENCE DESCRIPTION: SEQ ID NO:65:

GGGTGCCTTT ATCCAGCAAG GATGC  25

( 2 ) INFORMATION FOR SEQ ID NO:66:

( i ) SEQUENCE CHARACTERISTICS:
( A ) LENGTH: 25 base pairs

```
        ( B ) TYPE: nucleic acid
        ( C ) STRANDEDNESS: single
        ( D ) TOPOLOGY: unknown ( i i ) MOLECULE TYPE: other nucleic acid
        ( A ) DESCRIPTION: /desc = "primer"

( x i ) SEQUENCE DESCRIPTION: SEQ ID NO:66:

TGCCTTTATG CACCAAGGAT GCGAT                                      2 5

( 2 ) INFORMATION FOR SEQ ID NO:67:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: unknown ( i i ) MOLECULE TYPE: other nucleic acid
        ( A ) DESCRIPTION: /desc = "primer"

( x i ) SEQUENCE DESCRIPTION: SEQ ID NO:67:

GCAGCTGCTG ACATCT                                                1 6
```

RNA EDITING ENZYME AND METHODS OF USE THEREOF

CROSS-REFERENCE TO RELATED APPLICATIONS

This is a continuation-in-part of U.S. application Ser. No. 08/457,459, filed Jun. 1, 1995, which is a continuation-in-part of U.S. application Ser. No. 08/280,443, filed Jul. 25, 1994, now U.S. Pat. No. 5,643,778, which is a continuation-in-part of U.S. application Ser. No. 08/197,794, filed Feb. 17, 1994, now abandoned.

This invention was funded by Grant No. GM 40536, CA 09171, and CA 10815 from the Department of Health and Human Services. The U.S. Government has certain rights in this invention.

FIELD OF THE INVENTION

This invention relates generally to the production of proteins via genetic engineering techniques, and more specifically relates to the cloning and use of a novel RNA editing enzyme.

BACKGROUND OF THE INVENTION

Double-stranded adenosine deaminase (DRADA) is an adenosine deaminase specific for double-stranded RNA (dsRNA) [Bass and Weintraub, Cell, 55:1089–1098 (1988); Wagner et al, Proc. Natl. Acad. Sci. USA, 86:2647–2651 (1989)]. DRADA deaminates multiple adenosine (A) residues to inosines (I) by a hydrolytic deamination reaction [A. G. Polson et al, Biochem., 30:11507 (1991)] in both inter- and intra-molecular dsRNAs [Nishikura et al, EMBO J., 10:3523 (1991)], creating I-U mismatched base pairs in dsRNAs. The accumulation of extensive mismatched I-U base pairs in the dsRNA causes unwinding of the RNA double helix. DRADA is the first and so far, the only, RNA-unwinding activity that results in an accompanying base modification on the substrate RNA. This dsRNA unwinding/modifying activity further differs from other dsRNA unwinding activities or RNA helicases in that it seems to bind specifically to dsRNA.

Several examples of in vivo interaction of this enzymatic activity with cellular as well as viral gene transcripts have been reported [Kim and Nishikura, Semin. Cell Biol., 4:285–293 (1993)]. For instance, maternal fibroblast growth factor gene and also its antisense transcripts seem to be extensively modified by DRADA in Xenopus oocytes undergoing meiosis [Kimelman and Kirschner, Cell, 59:687 (1989)]. The enzyme is responsible for genesis of defective measles virus with biased hypermutation, which results in lethal human CNS diseases, measles inclusion body encephalitis [Cattaneo et al., Virol., 55:255 (1988); Bass et al., Cell, 56:331 (1989)]. Furthermore, an adenosine located in a short stem structure of HIV TAR was reported to be modified to inosine by DRADA in a tat dependent manner [Sharmeen et al., Proc. Natl. Acad. Sci., USA, 88:8096 (1991)].

Because the enzyme introduces changes in the sequence of its substrate RNA, DRADA is anticipated to be involved in the RNA editing process [see, Kim and Nishikura, in RNA Editing, R. Benne, Ed. (Simon and Schuster International, Chichester, England (1993), pp. 179–192]. Indeed, DRADA now seems to be responsible for at least the RNA editing of glutamate-gated ion channel subunits (glutamate receptor, GluR) which are responsible for the fast excitation of neurons in mammalian brain [M. Higuchi et al, Cell, 75:1361–1370 (1993)].

DRADA is thus implicated in conditions or disorders characterized by the malfunction or deficient functioning of neuronal transmission in mammalian brain, e.g., in disorders such as stroke, Huntingdon's disease, Alzheimers disease and other such neurological conditions, and may also be associated with aging.

There is a need in the art for the isolation and recombinant production of the protein which produces the enzymatic activity described for DRADA, to enable its use in genetic engineering, recombinant production of useful proteins and drug development and screening.

SUMMARY OF THE INVENTION

In one aspect, the invention provides novel, isolated polynucleotide sequences encoding human DRADA proteins. The polynucleotide sequences encoding these proteins are illustrated in FIGS. 1A–1J [SEQ ID NO:1]. Fragments of these sequences are also embodied by this invention. These polynucleotide sequences or fragments thereof may also be optionally associated with conventionally used labels for diagnostic or research use.

In another aspect, the present invention provides human DRADA proteins characterized by having RNA editing activity. These proteins are isolated from other cellular materials with which they are naturally associated, and have biological activities associated with a DRADA-like RNA editing function. The DRADA proteins, schematically illustrated in FIGS. 2A through 2C, are designated herein as a 140 kD protein [amino acid 1–1226 of SEQ ID NO: 2], an approximately 93 kD protein [aa 404–1226 of SEQ ID NO: 2], and an approximately 88 kD protein [aa 440–1226 of SEQ ID NO: 2]. An approximately 83 kD protein has also been identified on polyacrylamide gel and biochemically purified. Advantageously, one or more of these proteins is capable of being produced recombinantly.

In still other aspects, the invention provides an expression vector which contains at least a polynucleotide sequence described above, a host cell transformed with such an expression vector and methods of using these vectors and host cells in the recombinant production of DRADA proteins.

In yet a further aspect, the invention provides a polyclonal or monoclonal antibody generated by use of one of these human DRADA proteins or fragments thereof as an immunogen.

In another aspect, the invention provides a diagnostic reagent, such as a DNA probe, i.e., an oligonucleotide fragment derived from the polynucleotide sequence encoding one of the proteins of the invention or from the complementary strand. The reagents may be optionally associated with a detectable label.

In yet another aspect, the present invention provides a variety of methods for using an above described poly- or oligo-nucleotide sequence, a protein or an antibody, as an agent in a therapeutic composition for treating disorders characterized by deficient or abnormal DRADA.

In yet a further aspect, the invention provides methods for use of these novel above-identified proteins, sequences and antibodies in the development and screening of compounds useful as therapeutics for the treatment of neurological disorders and diseases which can affect the central nervous system, such as Alzheimer's disease, HIV or subacute sclerosing panencephalitis (SSPE).

In a further aspect, the present invention provides for compounds or drugs produced by use of the above methods.

BRIEF DESCRIPTION OF THE DRAWINGS

FIGS. 1A-1J illustrate the continuous cDNA and amino acid sequences [SEQ ID NO: 1 and 2] of human DRADA proteins. A putative bipartite nuclear localization signal is boxed. The N-terminal sequences of the 93 kD and 88 kD proteins are indicated by the arrows. The three repeats of a dsRNA binding motif (DRBM) are underlined.

FIG. 5 illustrates a comparison between the three DRBM of human DRADA, indicated as DRADA-1 [SEQ ID NO: 3], DRADA-2 [SEQ ID NO: 4] and DRADA-3 [SEQ ID NO: 5] and by underlining in FIGS. 1A-1J, and the DRBM of other dsRNA binding proteins obtained from Genbank and EMBL databases, including P68kinase-1 [SEQ ID NO: 6], P68kinase-2 [SEQ ID NO: 7], TIKkinase-1 [SEQ ID NO: 8], TIKkinase-2 [SEQ ID NO: 9], HuTRBP-1 [SEQ ID NO: 10], HuTRBP-2 [SEQ ID NO: 11], HuTRBP-3 [SEQ ID NO: 12], X1TRBP-1 [SEQ ID NO: 13], X1TRBP-2 [SEQ ID NO: 14], X1TRBP-3 [SEQ ID NO: 15], Staufen-1 [SEQ ID NO: 16], Staufen-2 [SEQ ID NO: 17], Staufen-3 [SEQ ID NO: 18], Staufen-4 [SEQ ID NO: 19], Staufen-5 [SEQ ID NO: 20], Huson-a [SEQ ID NO: 21], E3L [SEQ ID NO: 22], Ns34 [SEQ ID NO: 23], Pac1 [SEQ ID NO: 24], RNase III [SEQ ID NO: 25] and a Consensus sequence based on all of these sequences [SEQ ID NO: 26]. The amino acids in bold print indicate the most frequently occurring amino acids in a common position among the sequences listed in this figure. The location of the α-helix is also indicated.

FIG. 6B provides the nucleotide sequences of all intron-exon junctions and sizes of all exons and introns are listed [SEQ ID NO: 40]. The boundaries of the exons and introns are indicated by slashes. Exon sequences are indicated in capital letters, intron sequences in lower case letters. Splice donor (gt) and splice acceptor (ag) sites are underlined.

FIG. 7 provides the nucleotide sequence of the 5' flanking region and the transcription start sites of the human DRADA gene [SEQ ID NO: 41].

FIG. 8 provides the nucleotide sequence of the 3' flanking region and the polyadenylation site of the human DRADA gene [SEQ ID NO: 42]. Sequences of the 3' end of human DRADA cDNA and the genomic human DRADA sequence encompassing the region obtained in this study are aligned. The canonical polyadenylation signal AATAAA is boxed.

DETAILED DESCRIPTION OF THE INVENTION

The present invention provides isolated and characterized human DNA sequences encoding a double stranded RNA adenosine deaminase enzyme (DRADA), and fragments thereof. DRADA and its protein fragments are responsible for mRNA editing of generations of glutamate-gated ion channel subunits. The provision of the polynucleotide sequences of this invention permits DRADA proteins to be produced by expression of the sequence in recombinant host cells. Because they are produced by recombinant techniques, both the nucleotide sequences and resulting expressed proteins are free from contamination with other sequences, cellular materials or protein materials with which the nucleotide and protein sequences occur in nature.

I. The DRADA Proteins

The DRADA protein is characterized by an approximately 1226 amino acid protein sequence and an apparent molecular weight of approximately 140 kD [SEQ ID NO:2] (See, FIGS. 1A-1J). Included in this invention are fragments of the DRADA protein. Preferably, the 140 kD DRADA and these fragments are characterized by sharing the dsRNA deaminase activity. The DRADA fragments of this invention are biologically active and have similar biological activity to full-length human DRADA. Particularly desirable are the following fragments which have been found to be N-terminal truncated versions of DRADA: a DRADA protein spanning amino acids 404 to 1226 of SEQ ID NO: 2 and having an apparent molecular weight of 93 kD; and a DRADA protein spanning amino acids 440 to 1226 of SEQ ID NO: 2 and having an apparent molecular weight of 88 kD. A DRADA protein having an apparent molecular weight of 83 kD on the polyacrylamide gel and which was biochemically purified has also been identified.

Figure 3:
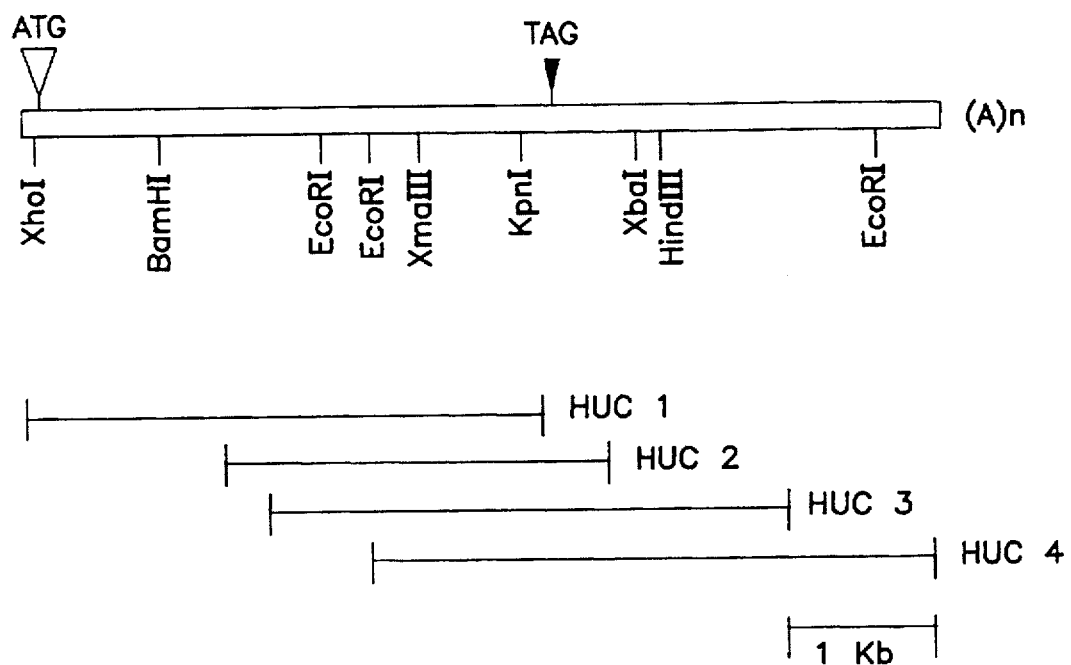
FIG. 3 illustrates the restriction map of the ORF of the human DRADA protein with indicated endonuclease enzyme restriction sites and the start (ATG) and stop (TAG) translation codons, and the overlapping human cDNA clones, HUC 1 through 4.

Three dsRNA binding sites are indicated in FIG. 3 by underlining at amino acids 502–573 of SEQ ID NO:2 (DRBM1), at amino acids 703–684 of SEQ ID NO:2 (DRBM2), and at amino acids 725–796 of SEQ ID NO:2 (DRBM3).

Deletion studies (see example 8) have revealed that the three DRBMs are not functionally equivalent. Rather, the presence of at least two DRMBs, DRBM1 and DRBM3, are essential for DRADA activity. Further, this indicates that DRBM1 and DRBM3 participate in the catalytic mechanism, in addition to RNA binding. The second DRBM can be removed without affecting DRADA enzymatic activity (A to I conversion). This result is surprising in light of the highly conserved amino acid sequences of the three DRBMs and the belief in the art that the DRBMs found in other types of dsRNA binding proteins are equivalent to each other [see, e.g., S. McCormack et al. Virol., 188:47-56 (1992), D. St. Johnson et al. Proc. Natl. Acad. Sci. USA, 89:10979-10983 (1992)]. The amino acid sequence of human and mouse DRADA deduced from cDNA sequences were compared. Although all three DRBM sequences are highly conserved between human and mouse DRADA, DRBM1 [aa 502-573 of SEQ ID NO:2] and DRBM3 [aa 725-796 of SEQ ID NO:2] contain ten and nine amino acid residue extensions of evolutionarily conserved sequence upstream of the N-terminal boundary of the 72 amino acid motif, whereas DRBM2 does not contain this 5' extension. The evolutionarily conserved sequence present upstream of DRBM1 and DRBM3 may add to these two repeats additional function, which distinguishes them from DRBM2.

Also included in the invention are analogs, or modified versions, of the DRADA proteins provided herein. Typically, such analogs differ by only 1, 2, 3 or 4 codon changes and are characterized by DRADA-like biological activity. Examples include polypeptides with minor amino acid variations from the illustrated amino acid sequences of DRADA (FIGS. 1A-1J; SEQ ID NO:2); in particular, conservative amino acid replacements. Conservative replacements are those that take place within a family of amino acids that are related in their side chains and chemical properties.

Additionally, the DRADA proteins [SEQ ID NO:2] of the invention may be modified, for example, to improve production thereof, to enhance protein stability or other characteristics, e.g. binding activity or bioavailability, to enhance its use for screening competitive compounds or to confer some other desired property upon the protein. For example, the catalytic domain of DRADA located in the carboxyl terminus at about amino acid 797 to 1226 of SEQ ID NO: 2 may be separately excised to obtain a DRADA protein more useful for screening compounds. Alternatively, a DRADA protein of the invention may be truncated or modified to remove the putative nuclear localization signal indicated in FIGS. 1A-1J at amino acids 169-170 and 181-185 of SEQ ID NO:2.

Similarly, the DRBMs may be modified by deletion or modification of one or more amino acid residues to provide alternate targets for the screening of compounds capable of binding thereto and inhibiting the function of DRADA. Similarly, the phosphorylation sites on DRADA, which may be identified by their known motifs on a variety of conventional computer programs, may be excised or altered for use in screening for binding or inactivating compounds.

Sequence analysis indicates that DRADA is a new member of the double stranded RNA (dsRNA) binding protein family. The adenosine-to-inosine conversion activity of the DRADA protein encoded by the cloned cDNA was confirmed by recombinant expression in insect cells. Use of the cloned DNA as a molecular probe documented sequence conservation across mammals, and detected a single transcript of 7 kb in RNA of all human tissues analyzed. The deduced primary structure of human DRADA revealed a bipartite nuclear localization signal, three repeats of dsRNA binding motifs (DRBMs), and the presence of sequences conserved in the catalytic center of deaminases, including a cytidine deaminase involved in the RNA editing of apolipoprotein B. Recent site-directed mutagenesis studies (see example 8 below) have identified four amino acids which are indispensable to DRADA's catalytic activity. These four amino acids include three putative zinc-coordinating residues $His^{910}$, $Cys^{966}$, $Cys^{1036}$ and $Glu^{912}$, which is predicted to be involved in the proton transfer functions of the enzyme.

Using the recombinantly expressed DRADA protein of the invention either in Spodoptera frugipedera insect cells or 293 mammalian cells, the inventor has directly demonstrated that DRADA is capable of editing the GluR-B RNAs in vitro.

Recent studies have also shown that although DRADA alone efficiently modifies an intronic "hot spot" adenosine in vitro, "Q/R" site editing requires the presence of a cofactor commonly present in cells and cellular extracts, including, e.g., HeLa nuclear extracts. It is anticipated that DRADA is involved in other gene systems, and that target genes exist, in addition to the glutamate-gated ion-channel subtype GluR-B transcripts, in different tissues. DRADA may be used in an editing capacity for these additional targets.

The DRADA proteins of this invention are useful in therapeutic compositions, as described in more detail in part VI below. These proteins may also be useful in diagnostic applications, as well as for generation of other therapeutic and diagnostic reagents, such as anti-DRADA antibodies. In common with other proteins generally, these newly-identified DRADA proteins may also serve as molecular weight markers or in other aspects in screening assays or as research tools. More desirably, the DRADA proteins are also useful for the screening and development of chemical therapeutic agents useful for reducing or enhancing the action of DRADA, as needed, and thereby correcting the ion channel expression.

II. DRADA Polynucleotide Sequences

Figure 2A:
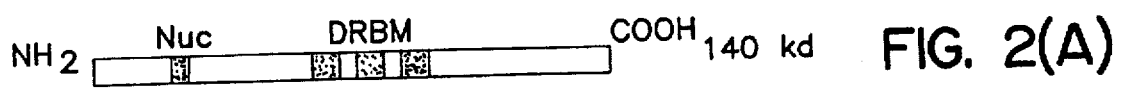
FIG. 2A illustrates a bar graph which represents the open reading frame (ORF) for a 140 kD form of human DRADA, with the putative nuclear localization signal indicated by a black box (NUC), and the dsRNA binding motifs (DRBM) indicated by hatching.

The DRADA gene spans 30 kb pairs and harbor 15 exons. The transcription of the DRADA gene driven by the putative promoter region, which contains no typical TATA or CCAAT box-like sequences, is initiated at multiple sites, 164 to 126 nucleotides upstream of the translation initiation codon. The three dsRNA binding motifs (DRBM), 70 amino acid residues long, are each encoded by two exons plus an intervening sequence that interrupts the motif at the identical amino acid position. This provides further evidence that the DRBMs are composed of two separate functional subdomains. Fluorescent in situ hybridization localized the DRADA gene on the long arm of chromosome 1, region q21. The genomic sequences provided in FIG. 6B and 7 herein have been deposited in the GenBank data base (accession numbers, U32347 and U32571). The approximately 6671 bp polynucleotide sequence of the human DRADA cDNA is provided in FIGS. 1A-1J [SEQ ID NO:1]. These sequences have been deposited in the GenBank data base (Accession No. U10439). It encodes the approximately 1226 amino acid protein sequence for the full-length DRADA protein, and portions of this polynucleotide sequence encode the N-terminal deletion proteins of DRADA having apparent molecular weights of 93, 88 and 83 kD. The nucleotide sequence of DRADA contains a short 5' untranslated region (154 bp), and a long 3' untranslated region (3336 bp), including a polyadenylate tract of 99 bases. It is currently not known whether this DNA contains the 5' end or cap site of DRADA mRNA. As shown in FIG. 2A, DRADA contains a single ORF (thin open box).

In addition to the polynucleotide fragments encoding the truncated DRADA protein sequences mentioned above, other fragments of these sequences may prove useful for a variety of uses. Desirably, these fragments are at least about 15 nucleotides in length and encode a desired amino acid sequence, e.g. an epitope, a therapeutically useful peptide desirably characterized by DRADA-like biological activity, or the like. These nucleotide sequences of the invention may be isolated as by conventional uses of polymerase chain reaction or cloning techniques such as those described in obtaining the bovine and human sequences in Examples 1 and 3, described below. Alternatively, these sequences may be constructed using conventional genetic engineering or chemical synthesis techniques.

According to the invention, the nucleic acid sequence [SEQ ID NO: 1] coding for the encoded DRADA proteins [SEQ ID NO: 2] described above and provided in FIGS. 1A–1J, may be modified. Utilizing the sequence data in these figures, it is within the skill of the art to obtain other polynucleotide sequences encoding the proteins of the invention. Such modifications at the nucleic acid level include, for example, modifications to the nucleotide sequences which are silent or which change the amino acids, e.g. to improve expression or secretion.

In still another alternative, the polynucleotide sequences may be modified by adding readily assayable tags to facilitate quantitation, where desirable. Nucleotides may be substituted, inserted, or deleted by known techniques, including, for example, in vitro mutagenesis and primer repair. Also included are allelic variations, caused by the natural degeneracy of the genetic code.

In addition to isolated cDNA sequences [SEQ ID NO: 1] and genomic sequences encoding the DRADA protein [SEQ ID NO: 2] described herein, this invention also encompasses other nucleic acid sequences, including those complementary to the illustrated DNA sequences, such as antisense sequences. Useful DNA sequences also include those sequences which hybridize under high or moderately high stringency conditions [see, T. Maniatis et al, *Molecular Cloning (A Laboratory Manual)*, Cold Spring Harbor Laboratory (1982), pages 387 to 389] to the DNA sequences illustrated in FIGS. 1A–1J. An example of a highly stringent condition is hybridization at 4×SSC at 65° C., followed by a washing in 0.1×SSC at 65° C. for an hour. Alternatively, an exemplary highly stringent hybridization condition is in 50% formamide, 4×SSC at 42° C. Other, moderately high stringency conditions may also prove useful, e.g. hybridization in 4×SSC at 55° C., followed by washing in 0.1×SSC at 37° C. for an hour. Alternatively, an exemplary moderately high stringency hybridization condition is in 50% formamide, 4×SSC at 30° C.

The nucleic acid sequences encoding these proteins are themselves useful for a variety of diagnostic and therapeutic uses. Advantageously, the nucleic acid sequences are useful in the development of diagnostic probes and antisense probes for use in the detection and diagnosis of various genetic disorders characterized by deficient or aberrant DRADA enzymes and glutamate-gated ion-channel communication. Oligonucleotide probes may be useful in such standard diagnostic techniques as Southern blotting and polymerase chain reaction. See discussion in parts V and VI below.

The nucleic acid sequences of this invention are also useful in the production of human DRADA proteins. Once constructed, or isolated, as described in further detail in Example 1 below, these DNA sequences or suitable fragments are preferably employed to obtain proteins of this invention.

III. Recombinant Expression of DRADA

To produce recombinant DRADA proteins of this invention, the DNA sequences of the invention are inserted into a suitable expression system. Desirably, a recombinant molecule or vector is constructed in which the polynucleotide sequence encoding DRADA is operably linked to a heterologous expression control sequence permitting expression of the human DRADA protein. Numerous types of appropriate expression vectors and host cell systems are known in the art for mammalian (including human) expression, insect, e.g., baculovirus expression, yeast, fungal, and bacterial expression, by standard molecular biology techniques.

The transformation of these vectors into appropriate host cells can result in expression of the selected DRADA proteins. Other appropriate expression vectors, of which numerous types are known in the art, can also be used for this purpose.

Suitable host cells or cell lines for transfection by this method include insect cells, such as *Spodoptera frugipedera* (Sf9) cells. Methods for the construction and transformation of such host cells are well-known. [See, e.g. Miller et al, *Genetic Engineering*, 8:277–298 (Plenum Press 1986) and references cited therein]. See, also, Example 5.

Similarly, mammalian cells, such as Human 293 cells, Chinese hamster ovary cells (CHO), the monkey COS-1 cell line or murine 3T3 cells derived from Swiss, Balb-c or NIH mice may be used. Suitable mammalian host cells and methods for transformation, culture, amplification, screening, and product production and purification are known in the art. [See, e.g., Gething and Sambrook, *Nature*, 293:620–625 (1981), or alternatively, Kaufman et al, *Mol. Cell. Biol.*, 5(7):1750–1759 (1985) or Howley et al, U.S. Pat. No. 4,419,446]. Another suitable mammalian cell line is the CV-1 cell line.

Similarly useful as host cells suitable for the present invention are bacterial cells. For example, the various strains of *E. coli* (e.g., HB101, MC1061, and strains used in the following examples) are well-known as host cells in the field of biotechnology. Various strains of *B. subtilis*, Pseudomonas, other bacilli and the like may also be employed in this method.

Many strains of yeast cells known to those skilled in the art are also available as host cells for expression of the polypeptides of the present invention. Other fungal cells may also be employed as expression systems.

Thus, the present invention provides a method for producing a recombinant human DRADA protein which involves transforming a host cell with at least one expression vector containing a recombinant polynucleotide encoding a human DRADA protein under the control of a transcriptional regulatory sequence, e.g. by conventional means such as transfection or electroporation. The transformed host cell is then cultured under suitable conditions that allow expression of the human DRADA protein. The expressed protein is recovered, isolated, and purified from the culture medium (or from the cell or cell lysate, if expressed intracellularly) by appropriate means known to one of skill in the art.

For example, the proteins may be isolated following cell lysis in soluble form, or extracted in guanidine chloride. If desired, the DRADA proteins of the invention may be produced as a fusion protein. For example, it may be desirable to produce such DRADA fusion proteins, to enhance expression of the protein in a selected host cell, or to improve purification. Suitable fusion partners for the DRADA proteins of the invention are well known to those of skill in the art and include, among others, β-galactosidase and polyhistidine.

IV. Production of Anti-DRADA Antibodies

The DRADA proteins of this invention are also useful as antigens for the development of specific antibodies, both polyclonal and monoclonal, to DRADA or various portions of the DRADA proteins, such as the DRBMs or catalytic regions, particularly those discussed above. Antibodies may also be developed to modified versions or analogs of DRADA. These antibodies may be produced by conventional methods, including the Kohler and Milstein hybridoma technique, recombinant techniques, such as described by Huse et al, Science, 246:1275–1281 (1988), or any other modifications thereof known to the art.

V. Diagnostic Reagents

The proteins, antibodies, and polynucleotide sequences (including anti-sense polynucleotide sequences) of this invention may be useful as diagnostic reagents for diagnosing certain neurological or central nervous system disorders, e.g., Alzheimer's disease, Huntingdon's disease, SSPE, measles inclusion body encephalitis, strokes and other conditions, including aging, which are found to be associated with abnormal, excessive, or deficient expression of DRADA. For example, a protein, antibody, or polynucleotide of the invention may be utilized to diagnose a naturally-occurring mutation in DRADA characteristic of such a condition. These reagents may optionally be labelled using diagnostic labels, such as radioactive labels, colorimetric enzyme label systems and the like conventionally used in diagnostic or therapeutic methods. The reagents may measure abnormal DRADA levels or detect mutant DRADA enzymes in selected mammalian tissue in conventional diagnostic assays, e.g., Southern blotting, Northern and Western blotting, polymerase chain reaction and the like. For example, as diagnostic agents the polynucleotide sequences may be employed to detect or quantitate normal or mutant DRADA mRNA or detect mutations in target gene RNA in a patient sample. The selection of the appropriate assay format and label system is within the skill of the art and may readily be chosen without requiring additional explanation by resort to the wealth of art in the diagnostic area.

Thus the present invention provides methods for the use of these protein, antibody or polynucleotide reagents in the diagnosis of disorders characterized by neurological symptoms, such as the malfunction of glutamate-gated ion-channels, or detection of genetic diseases. The methods involve contacting a selected mammalian tissue, e.g., skin, cerebrospinal fluids, or other cells with the selected reagent, protein, antibody or DNA sequence, and measuring or detecting the amount of DRADA present in the tissue in a selected assay format based on the binding or hybridization or the reagent to the tissue.

VI. Therapeutic Reagents

Alternatively, the DRADA proteins or nucleotide sequences may be useful as therapeutic reagents for delivery of biologically active DRADA to mammalian tissue. As one example, the recombinant protein may itself be administered by appropriate routes in a pharmaceutical composition to correct the malfunctioning of or defects in glutamate-gated ion channels, which can result in neurological disorders such as Alzheimer's disease, seizures and strokes. Alternatively, a desired DRADA nucleic acid sequence of the invention may be incorporated into a suitable vector or other delivery system. Suitable delivery systems are well known to those of skill in the art. Vectors containing such sequences may be administered, thus, treating deficiencies of DRADA via in vivo expression of the proteins of the invention. Such delivery systems enable the desired DRADA gene to be incorporated into the target cell and to be translated by the cell.

Still another method involves the use of the DRADA polynucleotide sequences for gene therapy. In the method, the DRADA sequences are introduced into a suitable vector for delivery to a cell containing a defect in the DRADA gene. By conventional genetic engineering techniques, the DRADA gene sequence may be introduced to mutate the existing gene by recombination or in addition to the inactive gene to replace it.

According to the above methods, a recombinant DRADA protein of the invention can be provided to a cell, particularly a cell in an individual having a condition characterized by an excess or a deficiency in DRADA. Such therapeutic uses are anticipated for disorders characterized by neurological symptoms and caused at least in part by the lack of active DRADA or the presence of abnormal or inactive DRADA enzyme in mammalian tissue. For example, it is anticipated that DRADA activity levels may change during the aging process. In such a circumstance, a therapeutic of the invention may be utilized to regulate DRADA activity to more desirable levels. As defined herein, a therapeutic of the invention may include the DRADA antibodies of the invention, which antibodies may be used to block inappropriate DRADA activity, e.g., by blocking binding of DRADA at a substrate-binding site, particularly DRBM1 or DRBM3, or by blocking a required amino acid residue such as $His^{910}$, $Cys^{966}$, $Cys^{1036}$ or $Glu^{912}$.

VII. Drug Screening and Development

The proteins, antibodies and polynucleotide sequences of the present invention may also be used in the screening and development of chemical compounds or proteins which have utility as therapeutic drugs for the treatment of neurological disorders, such as those identified above.

As one example, a compound capable of binding to DRADA and either preventing or enhancing its biological activity may be a useful drug component for the treatment or prevention of neurological disorders characterized by defect in the ion channel expression, or diseases such as SSPE or measles inclusion body encephalitis. In the former case, the drug may work by correcting channel expression. In the latter case, the drug may work by preventing the DRADA enzyme from mutating the relatively harmless measles virus into its lethal form. Additionally, based on the similarities of the DRADA DRBM and sequences within the HIV TAR binding protein, HuTRBP, and other dsRNA proteins, a compound identified as binding to, and/or blocking the DRADA DRBM or catalytic domain, may be a useful drug component for the treatment of HIV [Sharmeen et al, cited above] or other disease agents which invade the mammalian cell via a similar sequence (See FIG. 5).

Presently, conventional assays and techniques exist for the screening and development of drugs capable of competitively binding to selected regions of DRADA, such as the DRBM or catalytic domains. These include the use of phage display system for expressing the DRADA proteins or portions thereof, e.g., DRBMs, and using a culture of transfected E. coli or other microorganism to produce the proteins for binding studies of potential binding compounds. See, for example, the techniques described in G. Cesarini, FEBS Letters, 307(1):66–70 (July 1992); H. Gram et al, J. Immunol. Meth., 161:169–176 (1993); C. Summer et al, Proc. Natl. Acad. Sci., USA, 89:3756–3760 (May 1992), incorporated by reference herein.

Other conventional drug screening techniques may be employed using the proteins, antibodies or polynucleotide sequences of this invention. As one example, a method for identifying compounds which specifically bind to DRADA DNA sequences can include simply the steps of contacting a selected DRADA DNA fragment, e.g., a DRBM fragment of SEQ ID NO: 1 or a genomic fragment at an exon/intron junction [FIG. 6B], with a test compound to permit binding of the test compound to the DNA fragment; and determining the amount of test compound, if any, which is bound to the DNA fragment. Such a method may involve the incubation of the test compound and the DRBM DNA fragment immobilized on a solid support.

Another method of identifying compounds which specifically bind to DRADA DNA binding sequences can include the steps of contacting a DRADA DRBM DNA fragment immobilized on a solid support with both a test compound and the protein sequence which is the normal binding partner of the DRADA DRBM to permit binding of the normal binding partner protein to the DRADA DNA fragment; and determining the amount of the normal binding partner protein which is bound to the DNA fragment. The inhibition of binding of the normal protein by the test compound thereby indicates binding of the test compound to the DRADA DRBM DNA sequences.

Still other conventional methods of drug screening can involve employing a suitable computer program to determine compounds having similar or complementary chemical structures to that of the DRADA DRBM, and screening those compounds either for competitive binding to DRADA DRBM and/or using the base modification assay described below to detect enhanced or decreased DRADA activity in the presence of the selected compound.

Thus, through use of such methods, the present invention is anticipated to provide compounds capable of interacting with DRADA or portions thereof, and either enhancing or decreasing its biological activity, as desired. Such compounds are believed to be encompassed by this invention.

It should be understood that one of skill in the art may readily select the type of conventional screening method most desirable, as well as the reagent of this invention, e.g., the DRADA protein, nucleotide sequence, or fragment thereof or an antibody developed by use of such DRADA proteins.

The following examples which disclose the cloning and expression of human DRADA as well as the characterization of the genomic sequences are for illustrative purposes only, and should not be construed as limiting this invention in any way.

EXAMPLE 1

Isolation of Bovine DRADA Protein

Using an assay for modified bases designed to detect inosine converted from adenosines described below and according to methods described by Wagner and Nishikura, (1988) and Wagner et al., (1989), both cited above, a DRADA homolog was isolated from bovine liver nuclear extracts as follows:

A. Preparation of Nuclear Extract

Nuclear extract was prepared from bovine liver by the method described by Dignam et al, *Nucleic Acids Res.*, 11:1475–1489 (1983) with the following modifications. All procedures were carried out at 4° C. Fresh bovine liver (1 Kg), obtained from a local slaughterhouse, was minced using a blender, and further homogenized by a motor-driven Potter-homogenizer in 3 times the packed cell volume of a buffer containing 10 mM Hepes (pH 7.6), 25 mM KCl 0.15 mM spermine, 0.5 mM spermidine, 1 mM EDTA, 2M sucrose, and 10% glycerol. After centrifugation at 30,000 rpm in a Type 45 Ti Beckman rotor for 30 minutes, the nuclear pellet was suspended in a hypertonic buffer containing 0.02M Hepes (pH 7.9), 0.42M NaCl, 1.5 mM MgCl$_2$, 0.2 mM EDTA, 25% glycerol, 0.5 mM dithiothreitol (DTT), and 0.5 mM PMSF.

After two strokes in a glass dounce-homogenizer, the protein extract was cleared of debris by centrifugation at 30,000 rpm for 30 minutes. The activity was precipitated by adding solid (NH$_4$)$_2$SO$_4$ to 55% saturation (0.33 g/ml) and stirring for 1 hour at 4° C. After centrifugation at 35,000 rpm for 1 hour, the pellet was resuspended in a small volume (~1/10 volumes of initial cell pellets) of buffer A [0.02M Hepes (pH 7.5), 5 mM EDTA, 1 mM DTT, 17% glycerol, and 0.25 mM PMSF] containing 0.15M KCl, and dialyzed against three changes of 2 L of the same buffer to remove (NH$_4$)$_2$SO$_4$. The final nuclear extract was cleared by centrifugation at 30,000 rpm for 30 minutes and frozen in liquid nitrogen in aliquots. Typically, 1 Kg of liver yielded approximately 5 g of nuclear extract proteins.

B. ssDNA Agarose Column and First Cycle of Poly(I)•Poly(C) Agarose Column

All column chromatography procedures were carried out at 4° C. Approximately 5 g of crude nuclear extract (after adjusting salt concentration to 0.35M KCl) was passed through 85 ml (2.6×16 cm) of ssDNA agarose column equilibrated with buffer A containing 0.35M KCl at a flow rate of 20 ml/hour. The enzyme did not bind to the ssDNA and was found in the flow-through fraction. The ssDNA column served to remove certain ssDNA binding proteins that would otherwise also bind to the dsRNA column.

The flow-through containing the activity, which was immediately loaded onto 50 ml (2.6×10 cm) of poly(I)•poly(C) dsRNA agarose column that has been equilibrated with buffer A containing 0.35M KCl. The poly(I)•poly(C) column was washed sequentially with 100 ml of buffer A containing 0.5M KCl and then 100 ml of buffer A with 1.0M KCl at a flow rate of 20 ml/hour. The enzyme bound to the poly(I)-poly(C) duplexes very tightly under the conditions used, allowing other dsRNA binding proteins to be washed from the column with high salt buffer (up to 1.0M KCl).

The enzyme was eluted by raising the salt concentration of the buffer. The activity was eluted with 100 ml of buffer A containing 3.0M KCl and 0.2% Nonidet-P40 (NP40) at a flow rate of 10 ml/hour. NP40 (0.1–0.2%) was added to buffers in all of the subsequent steps of purification in order to prevent the loss of the dilute enzyme. Fractions of 10 ml each were collected and assayed for base modification activity of Example 2 to identify the active fractions. The 3.0M KCl fraction contained two major polypeptides with apparent molecular weights of 93 and 88 kD as judged by SDS-PAGE stained with silver.

C. Second Cycle of Poly(I)•Poly(C) Agarose Column

To further purify the enzyme from minor contaminants, the 3.0M KCl fraction was rechromatographed through a second purification cycle on the poly(I)•poly(C) column. Active fractions from the first cycle of poly(I)•poly(C) agarose column were pooled, diluted to 0.35M KCl with buffer A containing 0.2% NP40, and passed through a second cycle of 50 ml poly(I)•poly(C) agarose column. The column was washed and eluted as for the first poly(I)•poly(C) column, except that all buffers contained 0.2% NP40. Active fractions purified by two cycles of dsRNA affinity column chromatography were then concentrated by DEAE CL-6B ion exchange column chromatography.

D. DEAE CL-6B Ion Exchange Column

The active fractions from the second poly(I)•poly(C) agarose column were pooled and dialyzed against two changes of 2 L of buffer B [0.02M Hepes (pH 7.9), 5 mM EDTA, 1.0 mM DTT, 17% glycerol, and 0.25 mM PMSF]

containing 0.05M KCl and 0.2% NP40 for 8 hours. The dialyzed fraction was passed through 1.0 ml (1.0×1.3 cm) DEAE CL-6B (Pharmacia), equilibrated with buffer B containing 0.05M KCl and 0.2% NP40 at a flow rate of 4 ml/hour. After washing the column with 4 ml of buffer B containing 0.05M KCl and 0.2% NP40, the activity was eluted with 10 ml of buffer A containing 3.0M KCl and 0.2% NP40. Active fractions were identified by base modification assay of Example 2.

The final purified fraction containing the 93 kD and 88 kD polypeptides was estimated to be enriched about 22,000-fold over the initial liver homogenate in DRADA activity with a yield of 0.16% and was fractionated by SDS-PAGE (7% gel), and visualized by silver staining. Molecular weight standards used were α2-macroglobulin (108 kD), β-galactosidase (116 kD), phosphorylase B (94 kD), bovine serum albumin (67 kD), pyruvate kinase (58 kD), fumarase (48.5 kD), lactic dehydrogenase (36.5 kD), and carbonic anhydrase (30 kD).

The gel revealed three major peptides with apparent molecular weights of 93, 88, and 83 kD. These three proteins behaved identically on a two-dimensional isoelectrofocusing gel and also produced nearly identical peptide cleavage patterns after digestion with trypsin.

EXAMPLE 2

DRADA Assay and Base Modification Assay

A. DRADA Assay

DRADA was assayed in vitro [Bass et al, Cell, 48:607–613 (1987); Wagner et al, Mol. Cell. Biol., 8:770–777 (1988)]. Unless specified otherwise, the reaction was carried out in 100 μl reaction, which contained 10 fmol of α-[$^{32}$P]ATP-labeled c-myc dsRNA or human α-globin dsRNA [Wagner et al, cited above; Nishikura et al, EMBO J., 10:3523–3532 (1991)], 0.05M Tris (pH 7.0), 0.2M NaCl, 5 mM EDTA, 1 mM DTT, and 20% glycerol, and various amounts of bovine liver nuclear extract proteins or 20 ng of purified DRADA proteins. After incubation for 1 hour at 37° C., the reaction products were deproteinized and then precipitated with ethanol, as described previously [Wagner et al, cited above; Wagner et al, Proc. Natl. Acad. Sci. USA, 86:2647–2651 (1989)]. The extracted RNAs were analyzed with the below-described base modification assay.

B. Base Modification Assay

The DRADA activity was followed by determining the amount of adenosine converted to inosine by a fixed volume of each fraction in an in vitro base modification assay as follows. After the DRADA reaction, the RNA samples, together with 10 μg of Escherichia coli tRNA, were digested with nuclease P$_1$, into 5'-mononucleotides. The digests were analyzed by one-dimensional thin layer chromatography (TLC). The solvent system used was 0.1M sodium phosphate (pH 6.8)/ammonium sulfate/1-propanol, 100:60:2 (v/w/v) as described in SilverKlang et al, Methods Enzymol., 59:58–109 (1979). The radioactivity of the adenosine and inosine spots on TLC plates was quantified by the Phosphor Imaging System (Molecular Dynamics, Sunnyvale, Calif.).

EXAMPLE 3

Obtaining Bovine Clones

Bovine cDNA clones coding for the NH$_2$-terminus of 93 and 88 kD proteins were obtained by the method of multiple oligo-primed PCR amplification of cDNA (Lee and Caskey, in PCR Protocols: A Guide to Methods and Application, M. A. Innis et al, Eds., (Academic Press, Inc., San Diego, Calif. 1990), pp. 47–53.

A. Reverse-Transcriptase Polymerase Chain Reaction

In brief, degenerate sets of oligonucleotides that represented the codons for NH$_2$-terminal peptide sequences were synthesized. For the 93 kD protein, the sense primer was SEQ ID NO: 27: 5'CC GGAATTCNGGNAAA/GGTNGA3', and the antisense primer was SEQ ID NO: 29: 5'C GGGATCCNGCT/CTCCTT/CTGGT/CTTNA, which correspond to amino acid residues SEQ ID NO: 28: PGKVE and SEQ ID NO: 30: AEQKL, respectively. For the 88 kD protein, the sense primer was SEQ ID NO: 31: 5'C GGAATTCAAA/GACNGGNTAC/TGTNGA3', and the antisense primer was SEQ ID NO: 33: 5'CG GGATCCG/ATCG/ATCNGGG/ T/AATG/ATCG/ATC3", which correspond to residues SEQ ID NO: 32: KTGYVD and SEQ ID NO: 34: DDPIDD, respectively.

Restriction sites for EcoRI for the sense primer and BamHI for the antisense primer were included at the 5' end and are underlined in the sequences above. In addition, internal probes representing the residues flanked by the sense and antisense primers were synthesized. The sequence of the internal probe for the 93 kD protein was SEQ ID NO: 35: 5'C/TTTG/CACG/CACG/T/ AGGCTCCTIG3', and for the 88 kD protein was SEQ ID NO: 36: 5'CGGGATCCAT/ CTGNCCA/GTTC/TTCT/GTT3'.

All possible degenerate codons were included for the sense and antisense primers. For the internal probes, only the codons preferred in bovine genomes were included.

The first-strand cDNA synthesis was carried out using total RNA prepared from the cultured bovine endothelial cell line, BFA-1C BPT [J. Grinspan et al, J. Cell Physiol., 114:328–338 (1983)] and a GeneAmp® RNA PCR kit (Perkin Elmer Cetus) in a 20 μl reaction containing 10mM Tris-Cl (pH 8.3), 5 mM MgCl$_2$, 50 mM KCl, 1 mM each dA/G/C/TTP, 1 unit RNase inhibitor, 400 ng antisense primer, 2.5 unit/μl reverse transcriptase and 1 μg total RNA at 42° C. for 1 hour. The reaction was terminated by incubating the tubes at 99° C. for 5 minutes.

B. Screening of the Recombinant Library

The PCR was done in a 100 μl reaction containing 10 mM Tris-Cl (pH 8.3), 50 mM KCl, 2 mM MgCl$_2$, 4 μM each of sense and antisense primers, 2.5 unit AmpliTaq DNA polymerase. Amplification was performed in a thermal cycler with 35 cycles of 95° C. for 30 s, 48° C. for 1 min, 70° C. for 1 minute. A portion of the amplified product was analyzed by Southern hybridization at 42° C. in 6×SSC, 0.1% sodium pyrophosphate, 0.1% SDS, 0.1% Denhardt's, 50 mM Tris-Cl (pH 7.5), and 100 μg single-stranded DNA, using the internal probe labeled with [gamma-$^{32}$P] ATP [see Example 6].

The 75 bp cDNA that hybridized to the internal probe was purified from an agarose gel, digested with EcoRI and BamHI, and ligated with pBluescript KS+ plasmid. Selected subclones were sequenced using the sense and antisense primers. Sets of nested deletion mutants of the cDNA clones were generated using exonuclease III and mungbean nuclease [Ansubel et al, Current Protocols in Molecular Biology, Current Protocols, New York, N.Y. (1993)]. The deleted clones were sequenced by either Sequenase (U.S. Biochemicals) or Taq Dye Deoxy Terminator Cycle Sequencing Kit, and analyzed by the 373A DNA Sequencing system (Applied Biosystems). The overlapping sequences of subclones were aligned and combined by the Fragment Assembly program of the University of Wisconsin Genetics Computer Group (GCG) sequence analysis software package, Version 7.0 [Devereux et al, cited above].

Two cDNA clones were chosen for subsequent experiments, and named BUC1 and BUC2, which coded for the NH$_2$-terminus of the bovine DRADA 93 kD and 88 kD proteins, respectively.

Amino acid sequence of the NH$_2$-terminus of both the bovine 93 and 88 kD proteins, which are not blocked by acylation, were determined by microsequencing.

EXAMPLE 4

Obtaining the Human DRADA cDNA

A recombinant cDNA library in the Lambda Zap®II vector was made from human natural killer (NK) cells isolated from human blood, which cells are known to contain a high level of DRADA activity. The library was screened by the method of Maniatis et al., cited above, using the BUC2 clone as a specific probe.

The purified positive lambda phage was converted to a pBluescript plasmid by the in vivo excision method described in Stratagene's manual. The resultant cDNA plasmid, HUC1, contained approximately 4-kb of insert DNA, which hybridized to both BUC1 and BUC2 by Southern blot analysis. The insert of HUC1 was then used to rescreen the original cDNA library, from which additional cDNA clones, HUC 2, 3 and 4, were obtained. The four cDNA clones were sequenced and found to be overlapping, as illustrated in FIGS. 1A and 1B. The structure of cDNA and human DRADA protein was deduced from these clones. Following restriction site mapping to align the multiple overlapping cDNA clones, the nucleotide sequence of 6671 base pairs (bp) [SEQ ID NO:1] was determined for human DRADA.

Human DRADA cDNA sequence of 6671 base pairs contains a short 5' untranslated region (154 bp), and a long 3' untranslated region (2839 bp), including a polyadenylate tract of 99 bases (GenBank Accession No. U10439). This cDNA may contain the 5' end and/or cap site of DRADA mRNA. As shown in FIG. 2A, DRADA contained a single ORF (thin open box) which encodes a 1226-amino acid protein [SEQ ID NO: 2] with a calculated molecular mass of 136 kD. The proposed initiation codon is in agreement with the mammalian translation initiation consensus sequence [M. Kozak, *J. Cell Biol.*, 108:229–241 (1989)] and is preceded by an in-frame stop codon. The deduced amino acid sequence of this ORF is shown in FIGS. 1A–1J [SEQ ID NO:2].

Figure 2B:
FIG. 2B illustrates a bar graph which represents the ORF for the 93 kD truncated form of human DRADA, with DRBM indicated by hatching.
Figure 2C:
FIG. 2C illustrates a bar graph which represents the ORF for the 88 kD truncated form of human DRADA, with the DRBM indicated by hatching.

The ORF contained the NH$_2$-terminal sequences of both p93 and p88 kD protein, which appear to be both truncated forms, lacking, respectively, 403 and 439 amino acid residues of the NH$_2$-terminus of the full length 136-kDa DRADA protein (see FIGS. 2A through 2C by thick open boxes and in FIGS. 1A–1J by arrows). A putative bipartite nuclear localization signal is indicated in FIG. 2A by NUC, and a filled box and by boxing in FIGS. 1A–1J. Three dsRNA binding motif (DRBM) repeats are indicated in FIGS. 1 and 2, as underlining or hatched boxes, respectively.

EXAMPLE 5

Expression of Human DRADA

Confirmation that the cDNA clone isolated does indeed code for DRADA was obtained by expressing this protein in *Spodoptera frugipedera* (Sf9) cells as a recombinant baculovirus protein. Two recombinant constructs that coded for a full-length DRADA protein (pVLDRADA140) or a mutant lacking the C-terminal 346 amino acids (pVLDRADAΔ) were made.

Figure 4A:
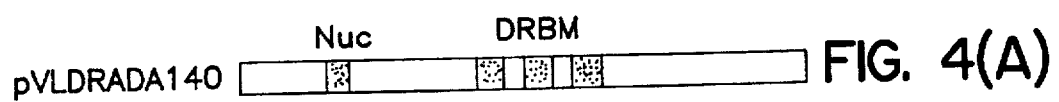
FIG. 4A illustrates a bar graph of plasmid pVLDRADA140, with the putative nuclear localization signal indicated by a black box (NUC), and the DRBM indicated by hatching.

For pVLDRADA140, XbaI to KpnI (the 5' end; 3.7 kb) of HUC1 and KpnI to XbaI (the 3' end; 1 kb) fragments of HUC2 were ligated into the commercially available baculovirus expression vector, pVL1393 (Invitrogen) at an XbaI site. The resulting recombinant expression vector pVLDRADA140 contained the endogenous translation initiation and termination codons as well as the 155 bp 5' untranslated sequence and 724 bp 3' untranslated sequence of full-length DRADA [SEQ ID NO: 1]. See FIG. 4A.

Figure 4B:
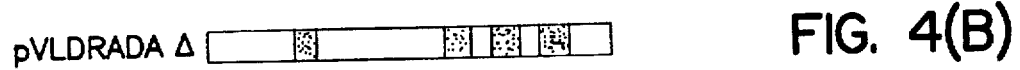
FIG. 4B illustrates a bar graph of plasmid pVLDRADAΔ with the putative nuclear localization signal indicated by a black box (NUC), and the dsRNA binding motifs (DRBM) indicated by hatching.

For pVLDRADA140Δ, a new termination codon was created at residue 880 by filling-in the over-hang of the XmaIII located downstream of the dsRNA binding motifs (DRBM). This procedure replaced the original sequence SEQ ID NO: 37: KILAAIIMKKDSE with a newly created C-terminal sequence, SEQ ID NO: 38: PQDSGHH-HYEKRL at residues 867 to 879. See FIG. 4B.

Sf9 insect cells were infected with the above-described recombinant baculoviruses. Cells were cultured by conventional means.

Protein production was assessed by labeling Sf9 cells with 50 μCi [$^{35}$S]methionine for 1 hour [O'Reilly et al, *Baculovirus Expression Vectors*, W. H. Freeman and Co., Oxford, England (1992)]. The labeled protein was analyzed by SDS-PAGE and fluorography. A unique band of 140 kD protein was detected in cells infected with the recombinant virus containing the entire coding sequence (DRADA140) indicating that a full length protein was expressed from the recombinant virus. A band of about 110 kD protein was detected in the cells infected with DRADAΔ.

The DRADA activity was analyzed in crude extracts made from 4×10$^7$ cells in an assay for detection of modified bases [described previously in Wagner et al, (1990) cited above] illustrating inosine 5'-monophosphate (pI) and adenosine 5'-monophosphate (pA) for DRADA 140 and DRADA delta, using 20 μg of protein at 37° C. for 2 hours. See Example 2. As a reference, crude extracts made from Sf9 cells, as well as HeLa cells, were assayed using increasing amounts (1, 10, 20 and 40 μg) of protein.

Only the extracts of the cells expressing DRADA140 showed adenosine to inosine conversion activity at a high level (5 times higher than that of HeLa nuclear extracts, which have previously been shown to contain a relatively high level of the DRADA activity [Wagner et al., (1990), cited above]). In contrast, the cells expressing a DRADAΔ, as well as uninfected Sf9 cells, displayed very little, if any, detectable base modification activity. These results confirm that the cloned cDNA indeed codes for a functional DRADA enzyme.

A separate assay tested in non-saturating, linear range (20 μg of protein at 37° C. for 30 min with excess of substrate dsRNA) indicated that Sf9 cells infected with DRADA 140 for 41 hours contained approximately 5 times more DRADA activity than HeLa cells.

Interestingly, the NH$_2$-terminally truncated forms of DRADA, p93 and p88, were not detected in Sf9 cells infected with recombinant virus carrying the entire DRADA ORF (FIG. 2A). Thus, these N-terminally truncated forms of DRADA appear to be produced by proteolysis during the protein purification.

EXAMPLE 6

Southern blot Analysis of the DRADA gene

The DRADA gene was detected in various species by Southern blot analysis. Briefly, twenty μg of chromosomal DNA was digested with either EcoRI and BamHI or EcoRI and HindIII, fractionated on an agarose gel (0.9%), and transferred to a Genescreen plus membrane. The membrane was hybridized with $^{32}$P-labeled probe (1.2 kb EcoRI/BamHI fragment of HUC1; $10^{16}$ cpm/mL) in solution containing 2×SSC, 1×Denhardt's solution, 40% formamide, 10% dextran sulfate, 1% SDS, and 0.05 mg/ml salmon sperm DNA, at 37° C. for 18 hours. The membrane was then washed with one change of 2×SSC at room temperature for 20 min followed by a wash with 2×SSC and 1% SDS at 37° C. for 30 minutes. The membrane was exposed at −70° C. for 68 hours.

The DNA was obtained from HeLa (human), BFA-1C BPT (bovine), MOPC111 (mouse), XTC-2 (Xenopus laevis; amphibian), and Sf9 (insect) cells. Two recently obtained overlapping human genomic clones were analyzed for restriction site mapping (see Example 10 below). These results suggest that all DNA bands including the faint ones arise from a single DRADA gene.

The Southern blot analysis indicated that the DRADA gene is well conserved in mammalian cells. The genomic DNA prepared from human, mouse, and bovine cells hybridized strongly with the human cDNA probe. However, this probe did not detect sequences in amphibian or insect genomes. Since the enzymatic activity of DRADA has been reported in these two species, additional cDNA probes including a DNA fragment encoding the C-terminal region predicted to contain the conserved catalytic domain were tested. All probes gave negative results. Thus, it is postulated that the DRADA sequence has not been well conserved during evolution, except in certain short stretches possibly involved in catalysis.

EXAMPLE 7

Expression of Transcripts Encoding DRADA

Expression of transcripts encoding DRADA was studied by Northern hybridization against mRNA from various human tissues. A Northern blot containing 2 µg of polyA$^+$ RNA (Clontech) was hybridized with a human cDNA probe according to the manufacturer's instructions. Briefly, the blot was prehybridized in 5×SSPE, 10× Denhardt's solution, 50% formamide, 2% SDS, and 0.1 mg/ml denatured salmon sperm DNA at 42° C. for 4 hours, followed by hybridization in a fresh solution containing the denatured probe at 42° C. for 18 hours. The blot was washed with several changes of 2×SSC and 0.05% SDS at room temperature for 30 minutes, then with one change of 0.1×SSC and 0.1% SDS at 50° C. for 1 hour. The blot was rehybridized with a glyceraldehyde 3-phosphate dehydrogenase (G3PDH) cDNA control probe.

The resulting Northern analysis blot located DRADA transcripts in all tissues tested, including the heart, brain, placenta, lung, liver, muscle, kidney and pancreas. The size of the DRADA mRNA (7 kb) indicates that the overlapping cDNAs (6,671 nucleotides) contain nearly the entire DRADA mRNA. As previously shown by the modified-base assay of crude extracts made from various tissues, the DRADA gene appeared to be expressed ubiquitously.

Brain tissue contains a high level of DRADA transcript, consistent with proposed involvement in the RNA editing of glutamate-gated ion-channel transcripts [Sommer et al., Cell, 67:11–19 (1991); Higuchi et al., Cell, 75:1361–1370 (1993)].

EXAMPLE 8

Structural Features of DRADA Protein

Computer-assisted inspection of the predicted primary structure revealed several features that illuminate the functional properties of DRADA. Alignments among different DRBM and deaminases were performed by the PILEUP, BESTFIT and GAP programs. Identification of various protein sequence motifs was performed by the MOTIFS program of the GCG sequence analysis package, version 7.0 [J. Devereux et al, Nucleic Acids Res., 12:387–395 (1984)].

A. DRADA and dsRNA Interaction

The central region of the DRADA protein contains three repeats of a dsRNA binding motif (DRBM; see FIGS. 1A–1J). The presence of dsRNA binding motifs in DRADA (aa500–700 of SEQ ID NO: 2) were first recognized as three internal repeats revealed during computer analysis of DRADA amino acid sequences.

The presence of these motifs explains the selectivity of DRADA for duplex RNA and identifies DRADA as a member of a growing family of DRBM containing proteins. This motif was recognized by several different groups in a number of proteins that are presumed to bind dsRNA and to carry out a diverse array of functions such as regulation of development, interaction with HIV, and cleavage of dsRNA. See, e.g., A. Gatignol et al, Mol. Cell. Biol., 13:2193 (1993); and D. St. Johnson et al, Proc. Natl. Acad. Sci. USA, 89:10979 (1992) among others. For example, the dissociation constant (Kd) of DRADA to a 575 bp dsRNA was 0.23 nM, comparable to other RNA binding proteins known to have very high affinity, such as TAT binding to TAR (Kd= 0.14 nM), and rev binding to RRE (Kd=0.3 nM) of HIV. Each motif is capable of binding independently to dsRNA allowing DRADA to make three contacts with dsRNA, and possibly increasing the affinity for dsRNA in a cooperative manner. It should be pointed out that multiple DRADA seem to bind to the long dsRNA, as binding studies and substrate requirement studies indicate [Nishikura et al, (1991), cited above].

These proteins carry out a diverse array of functions such as regulation and early development (Staufen) [St. Johnson et al, cited above] and interaction with human immunodeficiency virus RNA (TAR-binding protein) [Gatignol et al, cited above].

Note that there is an additional internal repeat at the position aa200–250 of SEQ ID NO: 2. This is not related to DRBM and appeared to be unique to human DRBM, since this repeat was not present in the bovine DRADA sequence.

There is a partial conservation of an RNP core consensus sequence just 62 residues upstream of DRBM-1 (GYVDF, residues 445–449 of SEQ ID NO: 2). The RNP consensus found in many SSRNA binding proteins, such as nucleolin and poly(A)-binding protein [S. R. Haynes, New Biol., 4:421–429 (1992)], consists of a 90-residue stretch of loosely conserved sequence within which reside highly conserved core sequences of eight (RNP-1) and five (RNP-2) residues. The short RNP-2-like stretch found in DRADA may participate in destabilizing A-U base pairs and in creating a local SSRNA region before adenosine deaminase.

In addition to DRBM, the computer analysis of the DRADA sequence by the MOTIFS program (GCG) revealed the presence of a bipartite nuclear localization signal comprising two basic residues followed by ten flanking residues and a basic cluster at residues 169 through 185 of DRADA SEQ ID NO: 2. This is consistent with the finding of the DRADA activity in the biochemically purified nuclear fraction of mammalian cells and tissues. The DRADA sequence contained numerous potential phosphorylation sites hinting that DRADA activity may be regulated by phosphorylation. Furthermore, although the enzyme was originally called "dsRNA unwindase," inspection of DRADA sequence did not show any significant homology to known helicase (DEAD or DEAH) proteins, confirming previous conclusions from biochemical analysis that DRADA does not have any classical helicase activity.

Since the biochemically purified 93 and 88 kD proteins, lacking the N-terminal region of the full length protein, exhibit the DRADA activity the amino acid residues directly involved in the catalytic mechanism are expected to reside at the C-terminal region, most likely the downstream of three repeats of DRBM. Note that the C-terminal truncated mutant (DRADAΔ) does not exhibit DRADA activity.

Mutagenic analysis of this substrate binding domain of DRADA has been carried out. The deletion of the first or third DRBM within the substrate binding domain consisting of three repeats of the motif, abolishes the enzyme activity, whereas the second motif seems to be dispensable. These results indicate that these three DRBM motifs are not equivalent in their roles in the DRADA activity.

B. Catalytic Mechanism of DRADA and Conservation of Residues Required for Deamination A set of evolutionarily conserved amino acid residues arranged and spaced in a specific sequence context has been reported in adenosine deaminase (ADA) and adenosine monophosphate (AMP) deaminases has been reported [Z. Chang et al, Biochem., 30:2273 (1991)], and also for cytidine deaminases and deoxycytidylate (dCMP).

The C-terminal region of DRADA contains the tripeptide sequences HAE and PCG, which are conserved in several cytidine and dCMP deaminases, including SEQ ID NO: 39: REPR [B. Teng et al, Science, 260:1816 (1993)]. (A database search revealed a nematode gene (T20H4.4) of unknown function [Wilson et al, Nature (London), 368:32–38 (1994)] with a considerable degree of sequence conservation to the C-terminal region of DRADA, particularly around the tripeptide HAE and PCG sequences. This nematode gene may encode a prototype of the vertebrate version of DRADA.) REPR is believed to be a subunit of a multicomponent enzyme containing a specific cytidine deaminase activity responsible for the RNA editing of apolipoprotein B mRNAs. These tripeptides contain histidine, glutamic acid, and cysteine, which are likely to be involved in the coordination of a zinc atom and formation of the catalytic center of DRADA.

Mutagenic analysis of this catalytic domain of DRADA was carried out. Mutation of the putative zinc-coordinating residues, $His^{910}$, $Cys^{966}$, and $Cys^{1036}$, abolished DRADA activity. Similarly, the $Glu^{912}$ residue, predicted to exert proton transfer functions of the enzyme, was confirmed to be indispensable. This data supports the conclusion that the hydrolytic deaminaltion mechanism of DRADA is similar to that of cytidine deaminases. This data also indicates sites of DRADA which may be modified to extinguish its activity, e.g., in circumstances where excessive DRADA activity is the cause of disease.

EXAMPLE 9

Isolation and Amplification of Genomic DRADA

One of the human DRADA cDNA clones, pHUC1, was used to isolate the DRADA gene from human genomic libraries. A recombinant phage (λHUG2), carrying 18 kb of genomic DNA corresponding to the central moiety of the DRADA gene, was isolated from a human genomic library constructed in λ Dash vector. The 5'and 3' regions of the gene from this library could not be isolated by using the probes corresponding to the 5' and 3' ends of the DRADA cDNA. Therefore, a genomic DNA library constructed in a yeast artificial chromosome (YAC) vector [Albertsen et al., Proc. Natl. Acad. Sci. USA, 87:4256–4260 (1990)] was screened by polymerase chain reaction (PCR) using a set of primers corresponding to the 5' end of the DRADA cDNA sequence [SEQ ID NO: 1] as follows.

A. Isolation of Genomic Clones

Figure 6A:
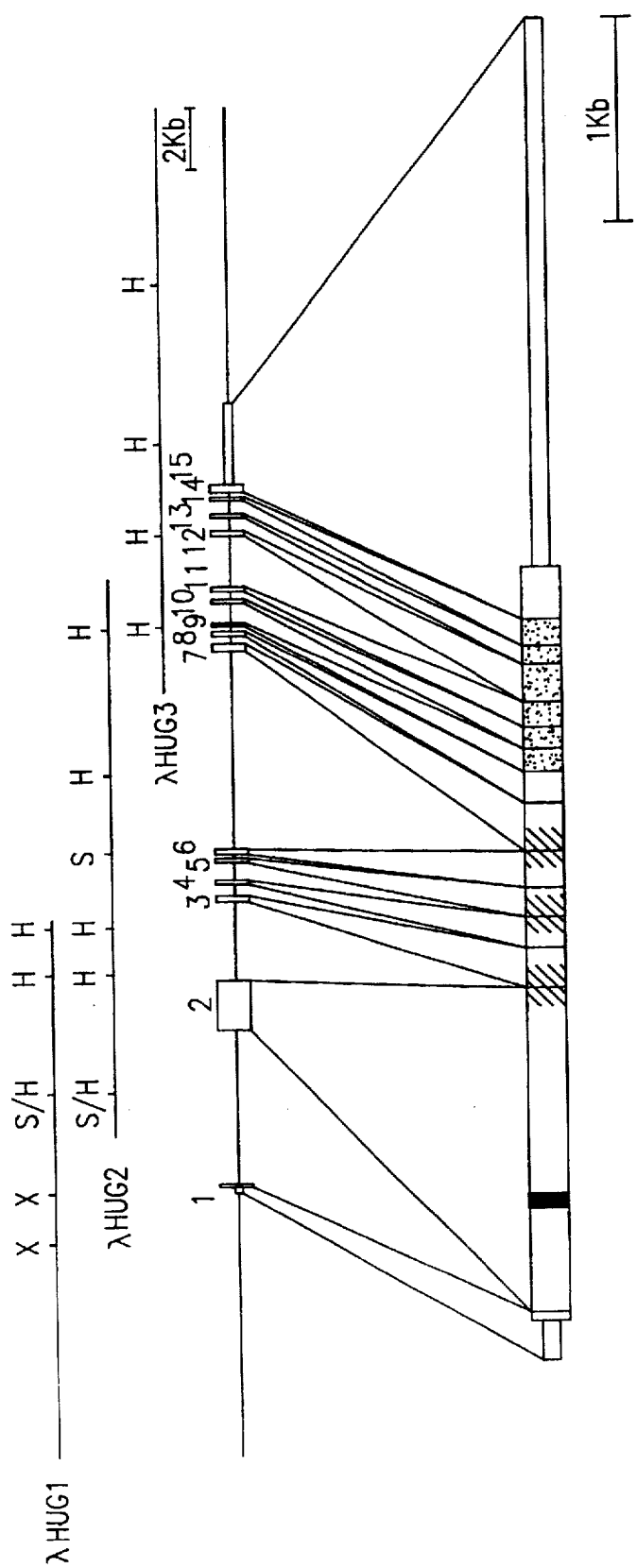
FIG. 6A provides the exon and intron organization of the human DRADA gene. The restriction sites used for alignment of three overlapping clones encompassing the DRADA gene, Hindm (H), XhoI (X), and SalI (S), are indicated. The exon-intron organization of the human DRADA gene together with their relation to the DRADA cDNA is also shown schematically. The gene consists of 15 exons (open boxes) and 14 introns. Untranslated regions within exons 1 and 15 are shown by thinner boxes. The putative bipartite nuclear localization signal (Nuc, filled box), three DRBM repeats (stippled boxes) spread over exons 2-7, and the putative deaminase domain (shaded boxes) encompassing exons 9-14, are indicated in the cDNA scheme.

Three overlapping clones encompassing the DRADA gene, λHUG1 (which contains the 5' end region of the DRADA gene including exon 1) and λHUG2 and 3 (which contain the region encompassing exons 2 to 15) were obtained as follows. Restriction maps and the relationship of overlapping λ clones are shown in FIG. 6A. A λ library constructed from genomic DNA of human lymphoid cells in λ Dash II vector was purchased from Stratagene (La Jolla, Calif.). The library was screened using a 1.1 kb BamHI-EcoRI restriction fragment of the human DRADA cDNA (position +804 to +1891, using the first nucleotide of Met as +1; 958–2046 of SEQ ID NO: 1) from plasmid pHUC1 [Kim et al., Proc. Natl. Acad. Sci. USA, 91:11457–11461 (1994)] as described [Sambrook et al., Molecular Cloning: A Laboratory Manual, 2d ed., Cold Spring Harbor Press (1989)], and a λ clone HUG2 containing exon (E) 2 to E11 was isolated. Since the clones containing exons besides E2 to E11 could not be isolated, a human YAC library with an average insert size of 100 kb (an original CEPH YAC library described by Albertsen et al., cited above) was screened using a set of PCR primers, YA3 [5' CTGGTATCTGAGCTGTCTG-3' (+84 to +66) SEQ ID NO: 57] and YS15 [nucleotides 5433–5452 of SEQ ID NO: 1, 5'-CAGTCAGCTAGACACACTCA-3' (+5279 to +5298)] corresponding to the intron region between E1 and E2 and the 5' end region of E2. A single positive YAC clone, HUY1 containing approximately 100 Kb of insert, was identified, and the yeast chromosome DNA from HUY1 was prepared as previously described [Albertsen et al., Proc. Natl. Acad. Sci. USA, 87:4256–4260 (1990)]. The yeast DNA was then used for PCR analysis using three sets of primers:

YS16 [SEQ ID NO: 43: 5'CCTCAGAACCT CTGTACTCC-3' (inside intron I1)] and YA4 [SEQ ID NO: 44: 5'-GTGGCAGTGACGGTGTCTGC3' (+196 to +177)];

YS1 [nucleotides 5–29 of SEQ ID NO: 1: 5'-GACCCGCGGAGTTTCCCGTGCCGAC-3' (−150 to −126)] and YA2 [SEQ ID NO: 46: 5'-CCTGCCGCGGATTCAT TGCGCCCG-3' (+16 to −8)];

YS15 [nucleotides 5433–5452 of SEQ ID NO: 1] and YA14 [SEQ ID NO: 45: 5'GTCACTGTTATCAAGGGACAC-3' (+6373 to +6353)].

The PCR results confirmed that HUY1 contained all of the DRADA exons because the 5'-end and 3'-end regions of DRADA cDNA were amplified from HUY1 DNA.

The HUY1 chromosomal DNA was partially digested by the restriction enzyme Sau3A1 to produce DNA fragments sized between 9 to about 20 kb. The digested DNA was then ligated into the XhoI site of a λ-phage vector GEM11 (Promega, Madison, Wis.) to construct a HUY1 sublibrary as recommended by the manufacturer (Promega). A 165 bp PCR product was amplified by YS1 [nucleotides 5–29 of SEQ ID NO: 1], and YA2 [SEQ ID NO: 46]. This PCR product and a 1.4 kb Hindm-EcoRI cDNA fragment (position +4673 to +6103) within DRADA E15 were used as probes, the HUY1 sublibrary was further screened and 2 λ clones were isolated (HUG1 and 3). DNAs from these λ clones and from the previously isolated HUG2 clone were prepared and analyzed by restriction digestion, followed by Southern blot hybridization or PCR analysis. The hybridization probe was prepared by the random primer labeling method (Feinberg & Vogelstein, 1983).

EXAMPLE 10

Characterization of DRADA Gene and Exon Mapping

The exon-intron structure of the human DRADA gene was determined from cloned DNA isolated from two separate genomic libraries. The exon-intron organization of the human DRADA gene together with their relation to the DRADA cDNA is shown schematically in FIG. 6A.

A. Characterization of DRADA Gene

The 5' end of the DRADA gene including the putative promoter region was characterized by sequencing the 1.6 kb insert of a subclone pHUG1.1 derived from λHUG1, containing a portion of exon 1 (E1) and approximately 1.4 kb 5' flanking sequence. All exon-intron boundary sequences were determined by sequencing the exon-intron junction present in relevant plasmid subclones using specific sequencing primers designed based on the DRADA cDNA sequence, SEQ ID NO:1.

The sequencing primers used were

YS3 (E2/I2), 5'CTACAGTCATGGCTTGCCAC-3' (+1446 to +1465) [nucleotides 1600 to 1619 of SEQ ID NO: 1];
YS4 (E3/I3), 5'GGTTGTCATCAATGGCCGAG-3' (+1614 to +1633) [nucleotides 1768 to 1787 of SEQ ID NO: 1];
YS5 (E4/I4), 5'CCTTCAGCCACATCCTTCTT-3' (+1810 to +1829) [nucleotides 1964 to 1983 of SEQ ID NO: 1];
YS6, 5'CCCAAGTTCCAATACTGTGTTG-3' (+1930 to +1951) (E5/I5 and I5/E6) [nucleotides 2084 to 2105 of SEQ ID NO: 1];
YS7, 5'CTATGCTCCTCCTCTCAAGGTC-3' (+2453 to +2474) (E7/I7 and I7/E8) [nucleotides 2607 to 2628 of SEQ ID NO: 1];
YS8, 5'ACCAGATAGCCATGCTGAGC-3' (+2525 to +2544) (E8/I8 and I8/E9) [nucleotides 2679 to 2698 of SEQ ID NO: 1];
YS9, 5'CTGTCAATGACTGCCATGCAG-3' (+2714 to +2734) (E9/I9) [nucleotides 2868 to 2888 of SEQ ID NO: 1];
YS10, 5'GAAATACAACTCCCAGACTGCG-3' (+2784 to 2805) (E10/I10 and I10/E1) [nucleotides 2938 to 2959 of SEQ ID NO: 1];
YS11, 5'GACAAGTCCTGCAGCGACC-3' (+2917 to +2935) (E11/I11) [nucleotides 3071 to 3089 of SEQ ID NO: 1];
YS12, 5'AGAGACTCCGTACCATGTCC-3' (+3086 to +3105) (E12/I12) [nucleotides 3240 to 3259 of SEQ ID NO: 1];
YS13, 5'GCTGTCGTGTGACAAGAGATG-3' (+3242 to +3262) (E13/I13) [nucleotides 3396 to 3416 of SEQ ID NO: 1];
YS14, 5'GGAGACAAGCGTCAACTGGTG-3' (+3366 to +3386) (E14/I14 and I14/E15) [nucleotides 3520 to 3540 of SEQ ID NO: 1];
YA1, SEQ ID NO: 47;
YA4, SEQ ID NO: 44;
YA5, SEQ ID NO: 48, 5'-CTCGTTGGAATAGTGGGATG-3' (+1770 to +1751) (I2–E3);
YA6, SEQ ID NO: 49, 5'AAGAAGGATGTGGCTGAAGG-3' (+1829 to +1810) (I3–E4);
YA7, SEQ ID NO: 50, 5'CAGAAGCCATGGAGTTGG-3' (+2071 to +2054) (I4–E5);
YA8, SEQ ID NO: 51, 5'GACCTTGAGAGGAGGAGCATAG-3 (+2474 to +2453) (I6/E7);
YA9, SEQ ID NO: 52, 5'GAATCTTGCGGCCGAGCAAGG-3' (+2605 to +2585) (I7/E8);
YA10, SEQ ID NO: 53, 5'TCTCCTCCCTTAGCAGGTTC-3' (+2840 to +2821) (I9/E10);
YA11, SEQ ID NO: 54, 5'GGACATGGTACGGAGTCTCT-3' (+3105 to +3086) (I11/E12);
YA12, SEQ ID NO: 55, 5'CATCTCTTGTCACACGACAGC-3' (+3262 to +3242) (I12/E13);
YA13, SEQ ID NO: 56, 5'CACCAGTTGACGCTTGTCTCC-3' (+3386 to +3366) (I13/E14).

From the exon-intron boundary sequencing data, the sizes of nine out of 14 introns were also determined because those introns were relatively small (I3, I4, I5, I7, I8, I10, I12, I13, and I14). The size of I2, I9, and I11 were determined by PCR amplification of plasmid subclone DNAs using the same primers used for exon-intron boundary sequencing (YS3/YA5 for I2, YS9/YA10 for I9, and YS11/YA11 for I11).

The relevant DRADA exons and introns were amplified by the PCR technique (Sambrook et al., cited above) using an automated DNA thermal cycler (Perkin-Elmer Cetus, Emeryville, Calif.). The intron size of I6 was determined separately after the localization of E6 and E7 as described below. According to the restriction analysis, exons E2–E6 were located within a 8 kb of SalI fragment of λHUG2. To further locate those exons, PCR was performed using primer YA4 and M13 reverse, which is a plasmid vector primer upstream of the 8 kb insert of the SalI-digested HUG2. The distance from the SalI site to E2 was determined according to the size of the amplified PCR product. E2 was located about 2 kb downstream of the second SalI site of HUG2. Since the intron sizes of I2 I5 had already been determined as mentioned above, the locations of E3 E6 were easily assigned by adding corresponding intron in between. Similarly, E10 was located by PCR using primer YS10 and M13 reverse, then the rest of exons (E7 E15) were located according to the corresponding intron size. Since the distance between E6 and E11 was known (based on restriction analysis), and the distance between E7 and E11 was also known (by adding intron and exon sizes) the intron size of I6 could be calculated by subtraction.

After restriction analysis, relevant genomic DNA fragments excised from λ clones were subcloned into pBluescript II KS+ (Stratagene). Subcloned genomic DNA fragments were sequenced using the Taq DyeDeoxy Terminator Cycle Sequencing Kit, and analyzed by the 373A DNA sequencing system (Applied Biosystems, Foster City, Calif.).

The DRADA gene is split into 15 exons (FIG. 6A). The nucleotide sequences of all intron--exon junctions and all exon sizes are summarized in FIG. 6B. The longest exon (exon 15) is 2975 bp, and the shortest exon (exon 9) is 94 bp (FIG. 6B). Based on the results in FIG. 6B, the bipartite nuclear localization signal [Laskey & Dingwall, Cells, 74:585–596 (1993)] was assigned to the second exon, which is also the second longest (1586 bp). The three DRBMs are spread over 6 exons (exons 2 to 7) and each DRBM repeat is encoded by two adjacent exons, splitting the motif into its N-terminus and C-terminus halves. As shown in FIG. 6A, the putative deaminase catalytic domain is spread over 6 exons (exons 9 to 14).

B. The transcription initiation site and 5' end of the DRADA gene

Using the genomic plasmid pHUG1.1 as a probe, S1 mapping analysis of RNA samples prepared from two different human cell lines, HeLa and Raji was carried out as follows. Total RNAs from human cell lines HeLa and Raji were isolated by the guanidinium-isothiocyanate procedure [Chirgwin et al., *Biochemistry*, 18:5294–5299 (1979)]. If necessary, the RNAs were further purified by an oligo(dT) cellulose selection procedure [Aviv & Leder, *Proc. Natl. Acad. Sci. USA*, 69:1408–1412 (1972)]. The isolated total RNA (20 µg) was analyzed by the S1 nuclease mapping procedure of Berk & Sharp, *Proc. Natl. Acad. Sci. USA*, 75:1274–1278 (1978). 5'-end-labeling of the probe DNA was carried out as described Sambrook et al., cited above. The $^{32}$P-labeled DNA probe was heat denatured, hybridized in 80% formamide to total RNAs at 57° C. for 10 hours, digested with 80 U of nuclease S1, and analyzed by electrophoresis on a 8M urea in 8% polyacrylamide gel. The sizes of S1 nuclease protected probe fragments indicated that DRADA gene transcription initiates at multiple sites approximately 120 to 160 nucleotides upstream of the translation initiation site (data not shown). The 5' terminal regions of the DRADA mRNA were further confirmed by cDNA cloning of inverse PCR products (FIG. 6) [Zeiner, *BioTechniques*, 17:1051–1053 (1994)] as described in Example 11 below.

The potential transcription factor binding sites within the 5' flanking region of the human DRADA gene were searched through the transcription factors database (TFB) [Ghosh, *Nucl. Acids Res.*, 21: 3117–3118 (1993)] using the FIND-PATTERNS program (GCG). The DRADA gene sequence upstream of the predicted transcription start site contained no typical TATA or CCAAT box-like sequences, which is common for housekeeping genes such as DRADA [Conaway & Conaway, *Annu. Rev. Biochem.*, 62:161–190 (1993)]. Computer-assisted inspection of the 600 bp region upstream of these promoter sequences revealed the presence of the cAMP responsive element binding (CREB) site [Fink et al., *Proc. Natl. Acad. Sci. USA*, 85:6662–6666 (1988)] (−618 position), two GC-rich Sp1 binding site-like elements (−581 and −410 positions) [Dynan et al., *Nature*, 319:246–248 (1986)], and Pu box [Klemsz et al., *Cell*, 61:113–124 (1990)] (−194 position). It is anticipated that there are sequence elements in this 5'-flanking region that act as regulators of DRADA gene expression.

C. The 3' untranslated region and 3' end of the DRADA gene

A small portion of the C-terminal and the 3' untranslated region was found to be included in exon 15. The comparison of the 3' end of the human DRADA cDNA and the 3' end region of exon 15 identified the exact polyadenylation site and also a canonical polyadenylation signal sequence, AATAAA [Proudfoot & Brownlee, *Nature*(London), 263:211–214 (1976)] 24 nucleotides upstream of the polyadenylation site (FIG. 8). This 3' untranslated region (2737 bp) is unusually long.

D. Genomic organization of the dsRNA binding domains

Figure 9:
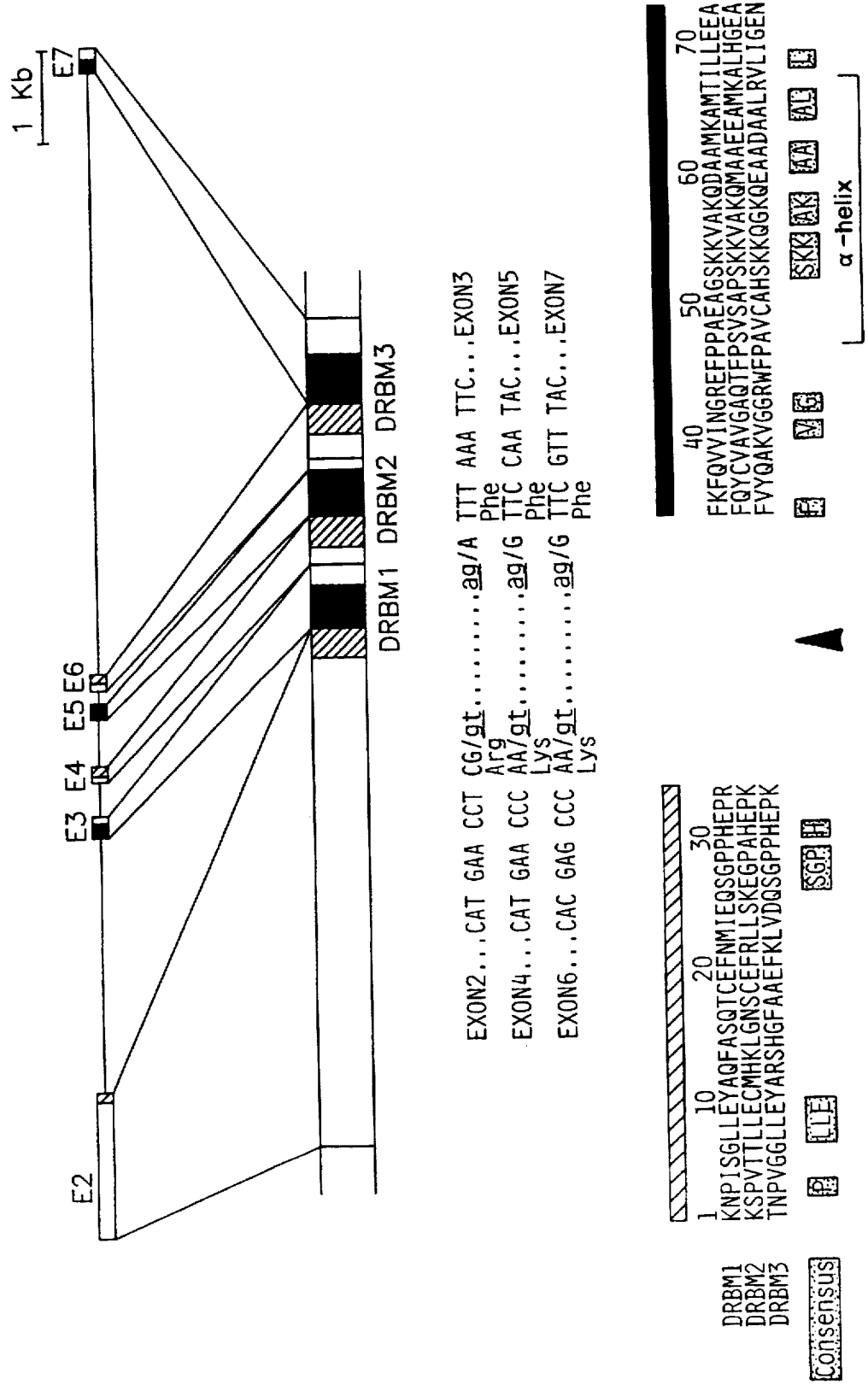
FIG. 9 provides the genomic organization of the dsRNA binding domains. The consensus sequence for DRBM [SEQ ID NO:26] is boxed and presented below the three repeats of the DRADA DRBM. The 20-residue core DRBM that is highly conserved among most of the dsRNA binding proteins and proposed to form an α-helix is also indicated. An arrowhead denotes the positions of introns that interrupt the N-terminal (stippled box) and the C-terminal (filled box) halves of each DRBM sequence at the identical position.

A remarkable aspect of the genomic organization of the DRADA gene is the fact that each of the three DRBMs is encoded separately by two adjacent exons (FIG. 9). In all three cases, the intron position is identical in that it interrupts the DRBM sequence at the same location (nucleotide and amino acid sequence), splitting each unit into identically sized NH2 and COOH regions.

The reading frame relationship of the three NH2 half exons and three COOH half exons of DRADA DRBM repeats is maintained identically. In other words, it would be possible to splice the NH2 half of DRBM1 located in the exon 2 to the COOH half of DRBM2 located in exon 5 without disrupting the reading frame, forming a protein with only two repeats of DRBM. In the DRADA gene, the two subdomains of the RNA binding motif are physically separated at the DNA level, and their respective functions as well as their gene arrangement seem to be highly conserved.

EXAMPLE 11

Cloning and Determination of 5' cDNA Regions by Inverse PCR

As described above in Example 4, the nucleotide sequence of 6671 bp of the human DRADA cDNA clones includes a short 5' untranslated region, a long 3' untranslated region, and a poly(A) tract of 99 nucleotides at the 3'-end. The size of the single DRADA mRNA (7.0 kb) revealed by Northern analysis in Example 7 suggested that a short additional extension of the 5' untranslated region may have been missing from the cDNA sequence [of SEQ ID NO:1]. One plasmid subclone derived from λHUG1 containing a 1.6 kb insert was found to hybridize to the DRADA cDNA probe corresponding to the 5' most end of DRADA mRNA by Southern blotting analysis. Sequencing of the insert revealed the region upstream of the 5' untranslated end previously determined by cDNA sequencing (FIG. 7). This is described in more detail below.

A cDNA synthesis kit (Boehringer Mannheim) was used for synthesis of doublestrand cDNA 1.5 µg of HeLa polyA+ RNA was reverse-transcribed by use of 40 units of AMV reverse transcriptase to synthesize the first-strand at 52° C. for 30 minutes with the presence of 20 picomole of YA3 primer [SEQ ID NO: 57]. This antisense primer corresponds to a sequence about 240 bp downstream of the 5' most end of the existing human DRADA cDNA clones. The second-strand synthesis with *E. coli* polymerase I and blunt-end treatment with T4 DNA polymerase were done as recommended by the manufacturer. The cDNA purification and ligation with T4 DNA ligase (Boehringer Mannheim) were performed as described [Zeiner, *BioTechniques*, 17:1051–1053 (1994)]. A portion (2 µl out of 100 µl) of the ligation products and 250 picomole of each primer YS2 [nucleotides 190 to 211 of SEQ ID NO: 1 5'CTACACCCATCCATTTCAAGGC-3' (+36 to +57)]; and YA1 [SEQ ID NO: 47, 5'-CGGCTACTCCGC ACTGGAAGTGGCC-3' (−95 to −118); (5'-end/E1)] were used for inverse PCR. Sense primer YS2 is about 30 bp upstream of the reverse transcription priming site, and antisense primer YA1 is about 130 bp upstream of YS2, which is very close to the 5'-end of the DRADA cDNA. The cycle conditions used were at: 95° C., 1 minute, and 35 cycles at 95° C., 1 minute; 60° C., 40 seconds; 72° C., 50 seconds; and finally 72° C., 5 minutes. The PCR products, approximately 120 bp in length, were cloned into the PCRII TA cloning vector (InVitrogen). The inserts of selected 5 cDNA clones were determined by DNA sequencing. All clones were found to contain the insert sequence, corresponding to the regions immediately upstream of the 5' end region of the human DRADA cDNA sequences [SEQ ID NO: 1].

EXAMPLE 12

Chromosomal Localization by Southern Hybridization

First, the localization of the DRADA gene was examined by Southern hybridization of human-rodent somatic cell hybrid DNAs. On Southern blots of BamHI-digested DNA from 18 different human Chinese hamster ovary hybrid cell lines, somatic cell hybrid DNA was scored for the presence or absence of human-specific hybridization with a DRADA cDNA fragment. The subchromosome location of the DRADA gene was then determined by fluorescent in situ hybridization.

A. Localization of DRADA Gene

Chromosome panels I and II containing human DNA, and a panel of 18 well-characterized human/hamster somatic cell hybrid DNA [Kouri et al., *Cytogenet. Cell Genet.*, 51:1025 (Abstract) (1989)] were purchased from BIOS Laboratories (New Haven, Conn.). Hybrids were characterized by karyotype analysis and the chromosome content of current passages of each cell line determined by Giemsa banding analysis of 20 metaphases (BIOS Laboratories). The two membranes contained BamHI digested DNA derived from somatic cell hybrid lines (8 µg) per lane. The human DRADA cDNA BstEII-EcoRI fragment (681 bp) encompassing exons 3, 4, and 5 [position +1210 to +1891, nucleotide 1364 to nucleotide 2045 of SEQ ID NO:1] was labeled by the random priming method [Feinberg & Vogelstein, *Anal. Biochem.*, 132:6–13 (1983)]. The nylon filters were prehybridized for 6 hours at 65° C. in solution containing 6×SSC, 5×Denhardt's, 10% dextran sulfate, 1% SDS and 100 g/ml salmon sperm DNA followed by hybridization for 16 hours at 65° C. in the same solution supplemented with 5×105 cpm/ml radio-labeled DRADA probe. Posthybridization washes were done for 10 minutes at 25° C. using 2×SSC twice, 15 minutes at 65° C. in 1×SSC/1.0% SDS once, and 15 minutes at 65° C. 0.1×SSC/1.0% SDS twice.

The DRADA cDNA probe identified a human DRADA specific band of approximately 7 kb molecular size in the human genomic DNA control lanes included in each blot. Of the 18 somatic cell hybrids examined, only 2 contained the DRADA specific band. These hybrids, #867 and #937, are the only ones which contain human chromosome 1. Complete correlation is therefore observed between the presence of the hybrid band and human chromosome 1.

B. Subchromosomal Localization—Fluorescent in situ hybridization

Fluorescence in situ hybridization was carried out under conditions which suppress signals from repetitive DNA sequences [Lichter et al., *Science*, 247: 64–69 (1990)]. λHUG2 containing a 14 kb fragment of the DRADA gene, plasmid pucl.77 [a probe specific for the heterochromatic region of chromosome 1, λRI-L1054 (specific for 1q21 31), plasmid 3021E (containing the human spectrin α1 gene [Shar et al, *J. Clin. Invest.*, 84:1243–1252 (1989); 1q21], or plasmid pAT5.0 containing the human antithrombin III gene [Prochownik et al., *J. Biol. Chem.*, 260, 9608–9612 (1985)], was purified using a Quiagen column following the protocol suggested by the manufacture (Quiagen Inc., Chatsworth, Calif.). Human metaphase chromosome spreads were prepared by standard methods from cultures of phytohemagglutinin-stimulated peripheral blood lymphocytes previously synchronized by treatment with 5-bromodeoxyuridine.

Briefly, approximately 1 µg of genomic DNA isolated from peripheral blood leukocytes of a normal male individual was added to a 50 µl reaction mixture consisting of 50 mM KCl, 10 mM Tris-HCl, pH 8.3, 1.5 mM MgCl2, 0.2 mM each of dATP, dCTP, dGTP, and dTTP. The reaction mixture was first heated at 98° C. for 10 minutes. After cooling to 80° C., 2.5 U of Taq polymerase (Perkin-Elmer Cetus) and 250 nmol of each oligonucleotide primer were added to each sample, and amplified for 30 cycles. Each cycle consisted of 1 minute at 94° C., 1 minute at 55° C., and 1 minute at 72° C. The last extension cycle at 72° C. was lengthened to 5 minutes. Southern blot analysis ruled out the possibility that major DNA rearrangements occurred during cloning of human genomic DNA derived from peripheral blood of a normal male individual using different probes distributed along the gene (data not shown).

Chromosome spreads were denatured in 70% formamide, 2×SSC at 70° C. for 2 minutes then dehydrated with a graded series of cold ethanol (70, 80, and 95%) for 1 minute each. A genomic phage clone, λHUG2, which corresponds to the DRADA locus was labeled with digoxigenin dUTP by nick translation (Sambrook et al., cited above) and used for hybridization at concentrations ranging from 150 to 300 ng per slide.

A second probe, pucl.77, used as a control was labeled with biotinylated dUTP. Before hybridization, the probes were preincubated with 45 fold excess of DNase I-digested human genomic DNA at 37° C. for 8 minutes. The labeled λHUG2 probe was combined with 50% formamide, 10% dextran sulfate, 2×SSC, and sheared human DNA and was hybridized in a 10 111 mixture of normal human metaphase chromosomes at 37° C. overnight. After hybridization, the slides were washed with 50% formamide in 2×SSC and then with 0.2×SSC, each at 37° C. for 15 minutes. They were then incubated with 3% bovine serum albumin in 4×SSC at 37° C. for 30 minutes and anti-digoxigenin conjugated with fluorescein isothiocyanate (Vector Laboratories, Burlingame, Calif.) at 37° C. for 30 minutes, followed by three washes for 10 minutes each at room temperature. The specific signal was detected with anti-digoxigenin conjugated with fluorescein isothiocyanate, and chromosomes were then counterstained with propidium iodide and analyzed. The specific signal on the long arm of chromosome 1 immediately distal to the heterochromatic region was identified. To conclusively prove the identity of the specifically labeled chromosome, probe pucl.77 which is specific for the heterochromatic region of chromosome 1 [Holger et al., *Advances in Neuroblastoma Research*, 3: 99–105 (1991)], and the λHUG2 clone was biotinylated. Detection of signal from pucl.77 was accomplished with avidin conjugated Texas red. Chromosomes were then counterstained with Dapi and mounted.

Analysis of the 80 metaphase chromosome spreads using a digoxigenin-labeled DRADA probe revealed 68 (85%) of the cells exhibited specific fluorescent signals (HUG2) on chromosome 1. The identity of the chromosome localization was confirmed by co-hybridizing with PUC1.77. Both PUC1.77 and the DRADA genomic probe hybridized to the same chromosome, and of importance as well is that the DRADA genomic probe gave a specific hybridization signal distal to the heterochromatic DNA of the long arm of chromosome 1. In addition, similar cohybridization experiments with three additional control probes already mapped in this region were carried out. These three probes, RI-L1054 (1q21 31), α1 spectrin gene (1q21), and antithrombin III gene (1q23 25), all gave a specific hybridization signal distal to DRADA, confirming the localization of the DRADA gene to 1q21 (data not shown).

C. DRADA localization to chromosome 1q21 region and human hereditary diseases

Thus, the human DRADA gene has been mapped to the long arm of the chromosome 1 in the 1q21 region. DRADA appears to be involved in RNA editing of certain subtypes of α-amino-3-hydroxy-5-methylisoxazole-4-propionic acid (AMPA) and kainate GluR subunits. The RNA editing of these subunits, mediated by DRADA, results in profound alterations in GluR channel properties such as gating, conductance, and ion permeability [Hollmann et al., *Science*, 252: 851–853 (1991); Burnashev et al., *Neuron*, 8:189–198 (1992); Köhler et al., *Neuron*, 10:491–500 (1993); Verdeorn et al., *Science*, 252:1715–1718 (1991)]. For instance, the AMPA channel consisting of the GluR-B subunit, which contains an editing-introduced positively charged arginine residue at the Q/R site within the TM2 domain, is impermeable to $Ca^{2+}$ while the AMPA channel made from GluR-A, -C, and -D subunits, containing a gene-encoded glutamine at the same Q/R site, allows a rapid influx of Ca2+ upon glutamate binding [Seeburg, *Trends Neurosci.*, 16: 359–365 (1993); Hollmann et al., cited above; Burnashev et al., cited above]. This implies that DRADA may regulate the critical physiological characteristics of certain AMPA and kainate channels. Dysfunction of these channels in the central nervous system has been implicated in conditions involving injury and neurotoxicity, and in the pathological states of certain neurodegenerative disorders such as epilepsy, Parkinson, Huntington, and Alzheimer's (Seeburg, cited above; Choi & Rothman, *Annu. Rev. Neurosci.*, 13:171–182 (1990)]. The availability of the human DRADA gene probe and sequence information provided herein may permit diagnosis of such diseases and injuries.

EXAMPLE 13

Oligonucleotides

A short synthetic GluR-B transcript was designed as a substrate RNA to examine editing abilities of DRADA. This fragment of GluR-B RNA (745 nucleotides) contains all of the sequences necessary for the formation of a short dsRNA structure (17 bp), encompassing the Q/R site within exon 11, and part of intron 11 as well as an additional intronic dsRNA region, which are required for efficient editing in vivo.

GluR-B oligonucleotides were designed to correspond to the murine sequence. The nucleotide positions indicated in parentheses are relative to the Q/R site, which was assigned as position 0 [Higuchi et al, cited above]. The following oligonucleotides used for reverse transcription, PCR, primer extension assay, in vitro mutagenesis, and DNA sequencing as described in the Examples below, were synthesized by an Applied Biosystems 380A DNA synthesizer and purified in 20% acrylamide—7M urea gels.

RTBin, 5'-AATTAACCCTCACTAAAGGGGTAAAATGAGAA TATGCAGCAA-3' [SEQ ID NO: 58] contains the sequence corresponding to the T3 RNA polymerase promoter sequence (underlined) followed by the antisense strand of the GluR-B gene intronic sequence (+315 to +337) [see, Higuchi, et al, cited above];

RTMBT3, CGCAATTAACCCTCACTAAAGGATGAACACACAG ATAAC-3' (+338 to +353) [SEQ ID NO: 59];
PCBex, 5'-TGAGATCTGGATGTGCATTG-3' (−193 to −178) [SEQ ID NO: 60];
PCT3, 5'-AATTAACCCTCACTAAAGGG-3' [SEQ ID NO: 61];
EXBex, 5'-CAACCTTGGCGAAATATCGCATCCTTG-3' (+2 to +28) [SEQ ID NO: 62];
EXBin, 5'-GAATTCATAGACACCATGAATATCCA CTTG-3' [SEQ ID NO: 63];
PCBamHI, CGTTACTAGTGAATCCGAGCTCG [SEQ ID NO: 64], corresponds to the polylinker sequence region of pCRII vector (Invitrogen);

PCBM1, 5'-GGGTGCCTTTATCCAGCAAGGATGC-3' (−14 to +10) [SEQ ID NO: 65];
PCBM2, 5'-TGCCTTTATGCACCAAGGATGCGAT-3' (−11 to +13) [SEQ ID NO: 66] (The underlined cytidine in PCBM1 and PCBM2 was introduced to replace a guanosine); and
SE1, 5'-GCAGCTGCTGACATCT-3' (+103 to +118) [SEQ ID NO: 67].

For the primer extension experiments of Example 15 below oligonucleotides were labeled with $[\gamma\text{-}^{32}P]ATP$ (6000 Ci/mmol, Amersham) and T4 polynucleotide kinase (Pharmacia) to a specific activity of $>1\times10^8$ dpm/μg as described [Sambrook et al, cited above].

EXAMPLE 14

Production of Recombinant DRADA Protein
A. Plasmids

For production of recombinant DRADA protein, a new construct, pVL-F-WT was prepared in which the 5' untranslated region of the GC rich DRADA sequence was removed and the sequence surrounding the initiation codon [Kozak, cited above] was altered to the one most preferred by baculovirus [O'Reilly et al, cited above]. In this construct, an epitope-tag FLAG [Hopp et al. *Biotech.*, 6:1205–1210 (1988)] was introduced at the $NH_2$-terminal of the protein. The expression level of F-WT in Sf9 cells was found to be increased at least 10-fold as compared to the original DRADA140 construct of Example 5 [Kim et al, (1994) cited above; Lai et al, *J. Biol. Chem.*, 270:17098–17105 (1995)]. pVL-F-Glu$^{912}$→Ala was used for synthesis of a mutant DRADA, which completely lacks the A to I conversion activity. Details of the construction of pVL-F-WT and pVL-F-Glu$^{912}$→Ala were described in Lai et al, (1995), incorporated herein by reference.

Plasmid pTA-Bmini contains a 745 bp BglII-XbaI fragment of the murine GluR-B genomic DNA sequence, encompassing the region in exon 11 and intron 11 that is essential for editing as described previously [Higuchi et al, cited above]. The BglII-XbaI fragment was excised from an expression plasmid B1 (a kind gift from Dr. P. H. Seeberg) and cloned into the BamHI-XbaI site of pCRII vector (Invitrogen).

B. Mutagenesis of pTA-Bmini

Using the Transformers™ Site-Directed Mutagenesis Kit (Clontech) with a selection primer PCBamHI and two mutagenesis primers PCBM1 and PCBM2, two mutant constructs, BM1 and BM2, were made, respectively.

Each construct had a single base change interrupting the 17 bp RNA duplex structure that is predicted to form. The mutation sites were directly confirmed by sequencing.

C. RNA Synthesis pTA-Bmini, pTA-BM1, or pTA-BM2 plasmids, linearized with the restriction enzyme SpeI, were each transcribed at 37° C. by 20 U of T7 RNA polymerase (Promega) for 60 min in 40 mM Tris-HCl (pH 7.5), 6 mM MgCl$_2$, 2 mM spermidine, 200 μg/ml BSA, 10 mM DTT. For [$^{32}$P]-labeled GluR-B RNA preparation, 500 μM each of GTP, CTP, UTP and 250 μM ATP with either 4 μCi or 200 μCi of [α-$^{32}$P]ATP (400 Ci/mmol, Amersham) were included in the reaction respectively. The warm $^{32}$P-RNA (4 μCi) was used in the in vitro editing assays and the hot RNA (200 μCi) was used for the DRADA base modification experiments (see Example 2). The template DNAs were eliminated by treatment with RNase-free DNaseI (Boehringer Mannheim) in the presence of RNasin (Promega) as described [Sambrook et al, cited above]. After extraction with phenol-chloroform (1:1), RNA was ethanol precipitated twice in 2M $NH_4OAc$, pH 4.

The recombinant plasmids and the wild-type baculovirus were co-transfected into Sf9 cells and crude cell extracts made as substantially described in Example 5 above.

D. Protein Assay

Recombinant FLAG-DRADA fusion proteins (WT or Glu921→Ala, 10 ng each) were analyzed by SDS-PAGE and silver staining. Protein concentrations were determined using either the Bio-Rad protein assay reagent or the Integrated Separation Systems Protein-Gold assay system with BSA as the standard. Protein analysis by one-dimensional SDS-PAGE (4% acrylamide stacking gel, 8% acrylamide resolving gel) was carried out as described by Laemmli, *Nature*, 277:680–685 (1970). Protein bands were visualized by silver staining [Burk et al, *Meth. Enzymol.*, 91: 247–254 (1983)].

E. Purification of Recombinant DRADA Proteins

The recombinant DRADA proteins F-WT and F-Glu$^{912}$→Ala, containing the FLAG epitope tag, were purified on anti-FLAG M2 immunoaffinity gel columns. Approximately 20 mg of crude extract protein, made from Sf9 cells infected with various recombinant baculoviruses, was applied to 1 ml of anti-FLAG M2 affinity gel equilibrated with Buffer A containing 0.05 M Tris (pH 7.0), 0.15M NaCl, 0.05% NP-40, 20% (v/v) glycerol, and 1 mM β-mercaptoethanol. The flow through fraction was applied twice to the same column to increase the binding efficacy of the recombinant protein. The column was washed with 30 ml of Buffer A containing 0.75M NaCl and then with 30 ml of Buffer A containing 0.15M NaCl. The recombinant DRADA proteins were extracted with 5 ml of Buffer A containing 0.15M NaCl and 75 µg/ml of the FLAG peptide. The eluted proteins were pooled and concentrated by Centricon 30 (Amicon) and stored at −70° C.

F. Immunoblotting

Ten ng of purified recombinant DRADA proteins were mixed in an SDS-polyacrylamide gel electrophoresis sample buffer, boiled for 5 min, chilled on ice, and separated on an 8% SDS-acrylamide gel. The gel was electrotransferred to nitrocellulose filters using standard methods [Sambrook et al, cited above]. The filters were washed once in Tris-buffered saline (TBS) (20 mM Tris and 500 mM NaCl, pH 7.5) and blocked with 3% non-fat dry milk at room temperature for 2 hr. The filters were washed three times with TTBS (0.3% Tween-20 in TBS) and then subjected to binding with an anti-FLAG antibody M2 (Kodak) at 1:2000 dilution in antibody buffer (1% non-fat milk containing TBS) at 4° C. overnight. After three washes in TTBS buffer followed by one in TBS, the filters were hybridized with a horseradish peroxidase-conjugated goat anti-mouse antibody (dilution 1:2000) in antibody buffer for 2 hr and washed with TTBS and TBS. The immunoblots were developed using the ECL system (Amersham).

Example 15

Cell Culture and Preparation of Mammalian Cell Nuclear Extracts

HeLa, 293, Saos-2, F9, and Balb/c 3T3 cells were grown in Dulbecco's modified essential medium containing penicillin and streptomycin supplemented with 2 mM glutamine and 10% fetal calf serum. Nuclear extracts were prepared by a modification of the Dignam et al procedure described in Example 1. Briefly, 1×10$^7$ cells were incubated for 10 min at 4° C. in a hypotonic buffer containing 10 mM Hepes pH 7.9, 1.5 mM MgCl$_2$, 10 mM KCl, 1 mM DTT, and protease inhibitors (0.4 mM PMSF, 3 µM pepstatin, 8 µM leupeptin, and 0.6 µM aprotinin). The swollen cells were homogenized using a Dounce homogenizer with a B pestle. Nuclei were pelleted at 4° C. by centrifugation for 10 min at 12,000 g and then extracted gently with a hypertonic buffer containing 20 mM Hepes pH 7.9, 0.42M NaCl, 1.5 mM MgCl$_2$, 0.2 mM EDTA, 25% glycerol, 1 mM DTT, and proteinase inhibitors. After centrifugation at 12,000 g for 30 min, the nuclear extract supernatant was dialyzed against a lower salt (0.1M NaCl) version of the same buffer. The extracts were aliquoted and stored at −70° C.

Example 16

Assays

A. Base Modification Assay

The A to I conversion activity of the purified recombinant DRADA proteins and the cell extracts was determined by a base modification assay as described in Example 2. Following incubation for 1 hr at 37° C., the reaction products were deproteinized, digested with P1 nuclease and analyzed by one-dimensional TLC.

B. In Vitro RNA Editing Assay

Editing of a synthetic GluR-B RNA labeled with a trace amount of [α$^{32}$P]-ATP, was assayed in vitro either by purified recombinant DRADA proteins of Example 13 alone or supplemented with nuclear extract proteins of Example 15. (Mutated GluR-B RNA substrates and a mutated DRADA were also tested in this assay.) RNAs with 293 cell extracts alone were also analyzed.

The standard editing reaction contained 20 fmol of a synthetic Bmini RNA substrate, 10 ng of recombinant DRADA proteins or 100 µg of nuclear proteins (from HeLa, 293, Saos-2, F9 or 3T3 cells), 0.02M Hepes pH 7.0, 0.1M NaCl, 10% glycerol, 5 mM EDTA, 1 mM DTT, and 250 U/ml of RNasin (Promega). Two of the three components (GluR-B RNA, DRADA and nuclear extracts) were preincubated at 37° C. for 1 hour prior to addition of the third component, which was followed by a 4 hr reaction at 30° C. The RNA was recovered by Proteinase K digestion, phenolchloroform extraction, and ethanol precipitation. The final RNA pellet was dissolved in DEPC treated ddH$_2$O and stored at −70° C. The RNAs were analyzed by RT-primer extension analysis.

C. Dideoxyoligonucleotide/Primer Extension Assay

1. Mouse Brain RNA Extraction and RT-PCR

The brain of a 2-month-old adult Balb/c mouse was freshly dissected and homogenized in RNA Stat-60™ (Tel-Test "B", Inc.) for extraction of total RNA following the manufacturer's instructions. Two µg of total RNA was reverse transcribed at 42° C. using the RTMBT3 antisense primer of Example 13. The first round of PCR was at 94° C., 5 min followed by 35 cycles at 94° C., 20 sec; 53° C., 1 min; 72° C., 30 sec, and 1 cycle at 72° C., 10 min for extension. In order to detect a reasonable band on a gel, a second round of PCR was required using the PCT3 and PCBex primers of Example 13.

2. The Assay

The primer extension assay was used to detect Q/R site or +60 site editing. Approximately 10 fmol of $^{32}$P-labeled extension oligonucleotide EXBex or EXBin of Example 13, that are complementary to mouse GluR-B sequences downstream of the Q/R or +60 sites, respectively, was mixed with 5 fmol of in vitro-edited GluR-B RNA, heated to 70° C. for 10 min, and annealed at 55° C. for 3–4 hr in 1× reverse transcription buffer (Boehringer Mannheim) including 10 µM each of dATP, dCTP, dGTP, and 250 µM dideoxy-TTP in a 9 µl volume. The primer-annealed RNA was then reverse transcribed with 1 U of AMV-RT (Boehringer Mannheim) at 42° C. for 45 min. The reactions were stopped by the addition of 4 µl of a formamide loading buffer.

For primer extension of the mouse brain GluR-B RNA, the RT-PCR product was first extracted with phenol-chloroform and then ethanol precipitated with 2M NH$_4$OAc, pH 4 to remove the residual nucleotides. Approximately 20 ng of DNA was then used for primer extension using $^{32}$P-labeled EXBex or EXBin primers. Briefly, the DNA was heated at 95° C. for 2 min, chilled on ice and annealed with 10 fmol of the primer in 1× Sequenase® buffer at 25° C. for 30 min. Extension was carried out for 5 min at 37° C. in the presence of 15 μM each of dATP, dGTP, dCTP, and ddTTP, 1 mM DTT, and the Sequenase® enzyme. All primer-extended DNAs were fractionated on a 15% polyacrylamide 8M urea gel. The ratio of the edited and unedited GluR-B RNAs was estimated by quantifying the radioactivity of the primer-extended product with a Phosphor Imaging System (Molecular Dynamics).

3. The Results

Editing of the in vitro reaction products examined by the dideoxynucleotide/primer extension assay using the recombinantly expressed DRADA proteins shows that DRADA is indeed involved in editing (i.e., the deamination of the adenosine to inosine) of the AMPA receptor subunit GluR-B RNA. There is a difference between the in vitro editing of two sites in the channel forming domain of GluR-B, namely the exonic Q/R site and the intronic +60 site, which has also been reported to be one of the "hot spots" for editing in vivo.

The purified recombinantly expressed DRADA protein synthesized in Sf9 insect cells was tested in the assay in two forms: a full-length 140 kD human DRADA protein carrying an epitope-tag peptide FLAG at the NH$_2$-terminal and F-Glu$^{912}$→Ala, which contains a site-directed point mutation substituting an alanine for the glutamic acid at aa 912 that normally participates in a critical proton transfer function in the DRADA catalytic mechanism.

The purified F-WT DRADA protein efficiently converted adenosine residues of a synthetic c-myc dsRNA (575 bp) to inosines, suggesting that the presence of the FLAG epitope tag at the NH$_2$-terminal of the recombinant DRADA protein did not interfere with its enzymatic activity. DRADA by itself is indeed the enzyme capable of converting multiple adenosine residues in dsRNA. DRADA alone in free form does efficiently modify the intronic "hot spot" adenosine (+60) with a high frequency up to 79%. It is possible that some of the eight exonic RNA editing sites which have been reported for the different AMPA and kainate GluR subunits [Seeburg et al, cited above] may be located in structurally favored sites more similar to the introic +60 site and can be edited by the free form of DRADA.

However, for certain sites, wild-type recombinant F-WT DRADA is necessary, but not sufficient, in an in vitro reconstitution assay for the site specific editing. It could not carry out the site-selective RNA editing of GluR-B RNA at the Q/R site in vitro, even at saturating enzyme levels (10-20 ng). When $^{32}$P-labeled GluR-B RNA was incubated with purified recombinant DRADA protein and examined for base modification by TLC analysis, a significant fraction of adenosine residues were found to be converted to inosines.

Purified recombinant DRADA cannot carry out the site-specific editing at the Q/R site, but it does modify adenosines at other sites, indicating that the editing of the exonic Q/R and the intronic sites may have different requirements. The site-selective Q/R site editing might require a different form of DRADA or a cofactor in addition to DRADA.

When the synthetic GluR-B RNA was incubated with HeLa nuclear extracts, using conditions similar to those previously used for the in vitro DRADA base modification assay, it was found that up to 45% of the Q/R site and 29% of the +60 site of the GluR-B RNA is edited. Cell extracts made from a variety of cell lines derived from different tissues were found to contain levels of the GluR-B RNA editing activity that correlate well with their levels of DRADA A and I conversion when using a long synthetic dsRNA substrate. However, the entire GluR-B RNA treated with 293 cell extracts in vitro remained unedited at all sites including the Q/R and +60 sites, the +4 site, and intronic spots at positions +262 to +264.

To test the possibility that the site-selective editing of GluR-B RNA requires an additional factor(s) other than DRADA, the recombinant F-WT DRADA protein was mixed with 293 nuclear extract (293 is a human embryonic kidney cell line, which contains very little editing activity by itself). Correct physiological pattern of editing of GluR-B RNA was reconstituted in vitro by mixing DRADA with a nuclear extract that by itself has no editing activity. An increase in Q/R site editing (14% from 4%) was observed. Editing events additionally occur on an individual RNA substrate at exonic site (+4) and intronic sites (+262~264).

At the same time the supplementation of the cofactor appears to suppress the editing at the intronic +60 site by DRADA (8% down from 60%). These results suggest that the recombinantly expressed DRADA is indeed capable of carrying out GluR-B RNA editing at the Q/R site but only in the presence of a cofactor(s).

Thus, in addition to the formation of an RNA duplex structure involving exon and intron sequences, Q/R site-selective editing by DRADA also requires a co-factor protein(s) commonly present even in non-neuronal cells and a mechanism other than the intrinsic sequence preference of DRADA.

Heating of 293 cell extracts at 70° C. prior to mixing with DRADA abolished the Q/R site editing. This inactivation by heat suggests that the cofactor is likely to be a protein(s). In addition, the yield of correct specific Q/R site editing by DRADA could be further increased when DRADA was preincubated with 293 extracts at 37° C. for 1 hr prior to the addition of the substrate GluR-B RNA. In contrast, the preincubation of DRADA with GluR-B RNA or 293 extract proteins with GluR-B RNA did not increase the Q/R site editing. The increase of Q/R editing, which is enhanced by incubating the cofactor with DRADA, but not with the substrate, suggests an interaction of the cofactor with DRADA. The apparent molecular weight of the DRADA protein is not altered by the preincubation, ruling out any post-translational modification or proteolysis of the DRADA protein by the nuclear extract. Similar mixing experiments with the recombinant DRADA protein and HeLa cell extracts showed an increased editing of the Q/R site after preincubation, but the enhancement effect (63% from 52%) was less obvious because the HeLa extract itself already contains high levels of the Q/R site editing activity.

The second effect of the cofactor, suppression of intronic +60 site editing, is unaffected by preincubation, suggesting that the two effects are independent. This is supported by the widely different ratios of Q/R site to intronic +60 site editing with cofactor derived from 293 and HeLa cell types.

Neither adenosine triphosphate 5l'-O-(3-thiophosphate) (ATPγS) nor the non-hydrolysable ATP analog adenylyl-imidodiphosphate (AMP-PNP) decreased the editing efficiency, suggesting that ATP is not required for the effect of the cofactor. The factor is not inhibited by non-hydrolysable ATP analogs.

The cofactor appears to restrict access of DRADA to the intronic editing site and to increase the site-specific editing at the Q/R site. The accuracy and efficiency of the Q/R site editing appear to be closely related to the quantitative balance or ratio between DRADA, cofactor, and substrate GluR-B RNA, as seen in a set of experiments using varying ratios of each component. The highest level of Q/R site editing observed in this reconstituted in vitro system, made from DRADA and 293 extracts, was 34%. Furthermore, the extract does not alter the mobility of the DRADA protein on denaturing protein gels.

The results of editing at the "Q/R" site, is a profound alteration of the $Ca^{+2}$ permeability of the GluR channel. The mutant DRADA protein (F-Glu$^{912}$→Ala) was tested for in vitro editing as well. As expected, the mutant DRADA did not edit GluR-B RNAs at the Q/R site or the +60 site even after supplementation and preincubation with 293 cell extracts. Similar results were achieved with mutated forms of Bmini RNA, BM1 and Bm2, which are not edited at either the Q/R or the +60 sites.

Analysis of mouse brain total RNA served as a control to compare the level of in vitro editing to that of in vivo. As compared to the mouse brain, the overall editing efficiency was lower for the RNA edited in vitro by DRADA and 293 extracts or by HeLa extracts; 100% versus 34 and 43%, respectively, at the Q/R site, but the relative editing efficiency observed at all sites was very similar. Overall, supplementation of 293 cell extracts to the purified recombinant DRADA protein significantly modified the efficiency and specificity of editing at the Q/R site and the intronic +60 site, achieving a pattern similar to the in vivo editing in the brain. Sequence analysis also revealed that the cofactor activates editing at the +263 intronic site, which is one of the sites that is actively edited in the mouse brain.

EXAMPLE 17

RT-PCR Amplification and cDNA Sequencing of the In Vitro Edited RNAs

The in vitro-edited RNA or the mouse brain RNA was first amplified by the RNA template-specific PCR as described [Sambrook et al, cited above]. Ten fmol of RNA were dissolved in $H_2O$ containing a specific RT primer, RTBin, and incubated at 70° C. for 10 min. Reverse transcription was carried out in a total reaction volume of 20 μl containing 50 mM Tris-HCl, pH 8.3, 75 mM KCl, 3 mM $MgCl_2$, 10 mM dithiothreitol, 40 U of RNasin, and 50 μM of each dNTP, and incubated with 2.5 U of AMV reverse transcriptase (Boehringer Mannheim) for 1 hr at 42° C., followed by heating at 95° C. for 5 min. Amplification of cDNA was achieved in 50 ul of 10 mM Tris-HCl, pH 8.3, 50 mM KCl, 200 μM of each dNTP, 2 mM $MgCl_2$, 150 nM each of PCBex and PCT3 primers, and 1 U of Taq DNA polymerase (Perkins-Elmer Cetus). The cycle conditions used were at 94° C., 2 min, and 35 cycles at 94° C., 20 sec; 55° C., 1 min; 72° C., 30 sec, and finally, 72° C., 10 min. The sequence designed for the antisense primer, PCT3, corresponds to the "extension" sequence that hybridizes solely to RNA-derived cDNAs, but not to any contaminating template DNA remaining from the in vitro transcription reaction. The amplified DNA fragment (545 bp) was digested with Bgl II and KpnI and cloned into the BamHI and KpnI sites of thepCRII vector (Invitrogen). The sequence of the entire Bmini gene region (545 bp) of cDNA inserts of randomly selected clones (16 to 35) was determined using Sequenase®, version 7.0 (United States Biochemical Corp.) with two sequencing primers, SE1 and the M13 reverse (present within the plasmid).

The sequence analysis for the RNA incubated with the purified F-WT DRADA protein confirmed the primer extension data that there was no Q/R site editing while the modification frequency at the +60 site was very high (up to 79%). Under these conditions, however, the cDNA sequence analysis also revealed that the exonic +4 site (18%) and several intronic adenosine residues other than the known hot spots (+3, +151, +186, +196, +237, +242, +269, +271, and +272 sites, 4 to 32%) were altered as well. This "inaccuracy" of editing site selection, observed in the RNA treated with the purified recombinant DRADA alone, once again suggests that site-selective editing may require a cofactor(s) in addition to DRADA.

All above-recited documents are incorporated by reference herein. While certain embodiments of the invention have been particularly described, it will be apparent to those skilled in the art that many modifications and variations may be made. Therefore, the present invention is not to be construed as limited by any of the particular embodiments shown, rather its scope will be defined only by the claims which follow.

What is claimed is:

1. A method for diagnosing a disorder characterized by inappropriate double stranded ribonucleic acid adenosine deaminase enzyme (DRADA) expression comprising the steps of:

contacting a sample of tissue from a patient with a diagnostic reagent comprising an antibody selected from the group consisting of a polyclonal antibody to DRADA and a monoclonal antibody to DRADA and a detectable label associated with said antibody, and measuring the amount of DRADA in said tissue by the association between said reagent and DRADA in said tissue.

2. The method according to claim 1 wherein the polyclonal or monoclonal antibody raised aganist a human double stranded ribonucleic acid adenosine deaminase enzyme (DRADA) protein SEQ ID NO:2.

3. The method according to claim 1 wherein the polyclonal or monoclonal antibody is rasied aganist a fragment of double stranded ribonucleic acid adenosine deaminase enzyme (DRADA) selected from the group consisting of:
   (a) double-stranded ribonucleic acid binding motif (DRBM) 1;
   (b) DRBM2;
   (c) DRBM3;
   (d) amino acids 404 to 1226 of SEQ ID NO:2;
   (e) amino acids 440 to 1226 of SEQ ID NO:2;
   (f) amino acids 797 to 1226 of SEQ ID NO:2;
   (g) amino acids 1 to about 796 of SEQ ID NO:2; and
   (h) amino acids about 186 to 1226 of SEQ ID NO:2.

4. The method according to claim 1, wherein the polyclonal or monoclonal antibody is raised against a DRADA fragment which retains the biological activity of DRADA.

5. A method for diagnosing a disorder characterized by inappropriate double stranded ribonucleic acid adenosine deaminase enzyme (DRADA) expression comprising the steps of:

contacting a sample of tissue from a patient with a diagnostic reagent comprising an oligonucleotide sequence complementary to a DNA sequence encoding DRADA and a detectable label associated with said sequence, and measuring the amount of DRADA in said tissue by the association between said reagent and DRADA in said tissue.

6. The method according to claim 5, wherein the oligonucleotide sequence is at least 15 basepairs and the DNA sequence encoding DRADA is SEQ ID NO:1.

7. A method for diagnosing a disorder characterized by inappropriate double stranded ribonucleic acid adenosine deaminase enzyme (DRADA) expression comprising the steps of:

contacting a sample of tissue from a patient with a diagnostic reagent comprising a protein sequence of DRADA and a detectable label associated with said protein sequence; and measuring the amount of DRADA in said tissue by the association between said reagent and DRADA in said tişsue.

8. The method according to claim 7, wherein the protein sequence is selected from SEQ ID NO:2 and fragments thereof which retains the biological activity of DRADA.

9. The method according to claim 7, wherein the protein sequence of DRADA is selected from the group consisting of:
   (a) double-stranded ribonucleic acid binding motif (DRBM) 1;
   (b) DRMB2;
   (c) DRMB3;
   (d) amino acids 404 to 1226 of SEQ ID NO:2;
   (e) amino acids 440 to 1226 of SEQ ID NO:2;
   (f) amino acids 797 to 1226 of SEQ ID NO:2;
   (g) amino acids 1 to about 796 of SEQ ID NO:2; and
   (h) amino acids about 186 to 1226 of SEQ ID NO:2.

* * * * *

UNITED STATES PATENT AND TRADEMARK OFFICE
CERTIFICATE OF CORRECTION

PATENT NO. : 5,763,174
DATED : June 9, 1998
INVENTOR(S) : Kazuko Nishikura

It is certified that error appears in the above-indentified patent and that said Letters Patent is hereby corrected as shown below:

Col. 5, line 3, replace "DRMBs," with -- DRBMs, --.

Col. 15, line 64, replace "(pVLDRADAA)" with -- (pVLDRADA$\Delta$) --.

Col. 17, line 11, replace "MOPC111" with -- MOPC11 --.

Col. 21, line 43, replace "(E10/I10 and I10/E1)" with -- (E10/I10 and I10/E11) --.

Col. 28, line 3, replace "5'-TGCCTTTATGCACCAAGGATGCGAT-3'" with
-- 5'-TGCCTTTATGCA$\underline{C}$CAAGGATGCGAT-3' --.

Col. 30, line 41, replace "Dideoxvoligonucleotide/Primer" with
-- Dideoxyoligonucleotide/Primer --.

Col. 32, line 60, replace "51'-O-(3-thiophosphate)" with -- 5'-O-(3-thiophosphate) --.

Signed and Sealed this

Twenty-ninth Day of February, 2000

Attest:

Q. TODD DICKINSON

Attesting Officer

Commissioner of Patents and Trademarks